(12) United States Patent
Kozelj et al.

(10) Patent No.: US 9,969,757 B2
(45) Date of Patent: May 15, 2018

(54) IONIC COMPOUNDS HAVING A SILYLOXY GROUP

(71) Applicant: HYDRO-QUÉBEC, Montréal (CA)

(72) Inventors: Matjaz Kozelj, Krka (SI); Abdelbast Guerfi, Brossard (CA); Julie Trottier, Mirabel (CA); Karim Zaghib, Longueuil (CA)

(73) Assignee: HYDRO-QUEBEC, Montreal (CA)

( * ) Notice: Subject to any disclaimer, the term of this patent is extended or adjusted under 35 U.S.C. 154(b) by 126 days.

(21) Appl. No.: 14/390,638

(22) PCT Filed: Apr. 5, 2013

(86) PCT No.: PCT/CA2013/050277
§ 371 (c)(1),
(2) Date: Oct. 3, 2014

(87) PCT Pub. No.: WO2013/149349
PCT Pub. Date: Oct. 10, 2013

(65) Prior Publication Data
US 2015/0093655 A1     Apr. 2, 2015

(30) Foreign Application Priority Data
Apr. 5, 2012   (CA) ...................... 2776178

(51) Int. Cl.
*H01M 10/056* (2010.01)
*H01M 10/0566* (2010.01)
(Continued)

(52) U.S. Cl.
CPC .......... *C07F 7/1896* (2013.01); *C07C 307/00* (2013.01); *C07C 311/48* (2013.01); *C07F 7/1852* (2013.01); *H01G 9/145* (2013.01); *H01G 11/62* (2013.01); *H01M 10/052* (2013.01); *H01M 10/056* (2013.01);
(Continued)

(58) Field of Classification Search
CPC ........... H01M 10/056; H01M 10/0566; H01M 10/052; H01G 11/62; H01G 9/145; C07C 307/00; C07C 311/48; C07F 7/1896
USPC ................. 429/345; 252/62.2; 548/110, 406; 556/482; 361/505
See application file for complete search history.

(56) References Cited

U.S. PATENT DOCUMENTS 2,637,623 A    5/1953   Janes
4,473,695 A    9/1984   Wrighton et al.
(Continued)

FOREIGN PATENT DOCUMENTS

CA    1 271 742 A     7/1990
CA    1333397 C       12/1994
(Continued)

OTHER PUBLICATIONS

Hao Luo, Machine translation of CN 102372732 A, Mar. 2012.*
(Continued)

*Primary Examiner* — Sean P Cullen
(74) *Attorney, Agent, or Firm* — Buchanan Ingersoll & Rooney P.C.

(57) ABSTRACT

There is provided an ionic compound having attached thereto a silyloxy group. There is also provided methods of making this ionic compound as well as electrolytes, electrochemical cells and capacitors comprising this ionic compound.

20 Claims, 14 Drawing Sheets

(51) Int. Cl.

| | |
|---|---|
| H01M 10/0569 | (2010.01) |
| H01G 9/145 | (2006.01) |
| H01G 11/60 | (2013.01) |
| C07C 307/00 | (2006.01) |
| C07C 311/48 | (2006.01) |
| C07F 7/18 | (2006.01) |
| H01M 10/052 | (2010.01) |
| H01G 11/62 | (2013.01) |
| G02F 1/15 | (2006.01) |
| H01G 9/022 | (2006.01) |

(52) U.S. Cl.
CPC ........... *H01M 10/0566* (2013.01); *G02F 1/15* (2013.01); *H01G 9/022* (2013.01); *H01M 2300/0045* (2013.01); *Y02E 60/13* (2013.01)

(56) References Cited

U.S. PATENT DOCUMENTS

| | | | |
|---|---|---|---|
| 4,713,378 | A | 12/1987 | Perrone et al. |
| 4,883,917 | A | 11/1989 | Smith et al. |
| 5,145,861 | A | 9/1992 | Ducep et al. |
| 5,202,217 | A | 4/1993 | Todoko et al. |
| 5,220,043 | A | 6/1993 | Dong et al. |
| 6,365,068 | B1 | 4/2002 | Michot et al. |
| 6,365,301 | B1 | 4/2002 | Michot et al. |
| 7,173,139 | B2 | 2/2007 | MacMillan et al. |
| 2007/0076349 | A1* | 4/2007 | Dementiev ............ H01G 9/038 361/502 |
| 2008/0191170 | A1 | 8/2008 | Walker et al. |
| 2008/0266642 | A1 | 10/2008 | Burrell et al. |
| 2008/0318767 | A1 | 12/2008 | Yoshimura et al. |
| 2009/0045373 | A1 | 2/2009 | Hammami et al. |
| 2009/0088583 | A1 | 4/2009 | West et al. |
| 2010/0304225 | A1 | 12/2010 | Pascaly et al. |
| 2012/0082903 | A1 | 4/2012 | Zhang et al. |
| 2015/0303511 | A1 | 10/2015 | Zhang et al. |

FOREIGN PATENT DOCUMENTS

| | | | |
|---|---|---|---|
| CN | 1032935 | A | 5/1989 |
| CN | 102372732 | A * | 3/2012 |
| CN | 103113242 | A | 5/2013 |
| DE | 36 17 269 | A1 | 11/1987 |
| EP | 0 315 166 | B1 | 2/1995 |
| JP | S61-018785 | A | 1/1986 |
| JP | H01-151535 | A | 6/1989 |
| JP | H03-273252 | A | 12/1991 |
| JP | 07-053331 | A | 2/1995 |
| JP | H07-053331 | A | 2/1995 |
| JP | 2004-002215 | A | 1/2004 |
| JP | 2006-510743 | A | 3/2006 |
| JP | 2007-091597 | A | 4/2007 |
| JP | 2008-515619 | A | 5/2008 |
| JP | 2009-149582 | A | 7/2009 |
| JP | 2010-059093 | | 3/2010 |
| JP | 2010-095473 | A | 4/2010 |
| JP | 2010-518113 | A | 5/2010 |
| WO | 2004/043954 | A2 | 5/2004 |
| WO | 2006/003902 | A1 | 1/2006 |
| WO | 2006/038013 | A1 | 4/2006 |
| WO | 2008/098151 | A2 | 8/2008 |
| WO | 2009/013046 | A2 | 1/2009 |
| WO | 2009/020038 | A1 | 2/2009 |
| WO | 2011/079804 | A1 | 7/2011 |
| WO | 2011/130114 | A1 | 10/2011 |

OTHER PUBLICATIONS

Arnold et al., "Magnesium and zinc complexes of functionalised, saturated N-heterocyclic carbene ligans: carbene ability and functionalisation, and lactide polymerisation catalysis," Dalton Transactions, (2009), No. 35, pp. 7236-7247. (Year: 2009).*

Bulut et al., "Preparation of [Al(hfip)4]—Based Ionic Liquids with Siloxane-Functionalized Cations and Their Physical Properties in Comparasion with Their [Tf2N]—Analogoues," ChemPhysChem, (2012), vol. 13, Issue 7, pp. 1802-1805. (Year: 2012).*

Kobayashi et al., "Catalytic Silicon-Mediated Carbon-Carbon Bond-Forming Reactions of Unactivated Amides," Journal of the American Chemical Society, (2011), vol. 133, No. 4, pp. 708-711. (Year: 2011).*

Segal et al., "Synthesis, physico-chemical and biological study of trialkylsiloxyalkyl amine coated iron oxide/oleic acid magnetic nanoparticles for the treatment of cancer," Applied Organometallic Chemistry, (2008), vol. 22, No. 22, pp. 82-88. (Year: 2008).*

Yabusaki et al., "1-Hydroxy-2-Tert-Butyldimethylsilyl-Sn-Glycero-3-Phophorylcholine. A Useful Intermediate in the Synthesis of Short Acyl Chain 1-Acyl-Sn-Glycero-3-Phosphorylcholines," Chemsitry and Physics of Lipids, (1976), vol. 17, Issue 2-3, pp. 120-127. (Year: 1976).*

Notification of Transmittal of the International Search Report (Forms PCT/ISA/220 and PCT/ISA/210) and the Written Opinion of the International Searching Authority (Form PCT/ISA/237) dated Jul. 2, 2013, by the International Bureau of WIPO in corresponding International Application No. PCT/CA2013/050277. (17 pages).

Extended European Search Report dated Oct. 6, 2015, issued by the European Patent Office in the corresponding European Application No. 13772854.9. (8 pages).

English language translation of Office Action dated Nov. 30, 2015, by the State Intellectual Property Office of China in corresponding Chinese Patent Application No. 201380018807.1. (12 pages).

Gharagheizi et al., "A group contribution method for estimation of glass transition temperature ionic liquids", Chemical Engineering Science, Oct. 22, 2012, vol. 81, pp. 91-105.

Ghosh et al., "Asymmetric Michael reactions catalyzed by a highly efficient and recyclable quaternary ammonium ionic liquid-supported organocatalyst in aqueous media", Organic & Biomolecular Chemistry, 2013, No. 11, pp. 1801-1804.

Guerfi et al., "LiFePO4 and graphite electrodes with ionic liquids based on bis(fluorosulfonyl)imide (FSI)—for Li-ion potteries", Journal of Power Sources, Jan. 10, 2008, vol. 175, No. 2, pp. 866-873.

Holzapfel et al., "Stable cycling of graphite in an ionic liquid based electrolyte", Chemical Communications, 2004, No. 18, pp. 2098-2099.

Holzapfel et al., "Stabilisation of lithiated graphite in an electrolyte based on ionic liquids: an electrochemical and scanning electron microscopy study", Carbon, Jun. 2005, vol. 43, No. 7, pp. 1488-1498.

Huang et al., "A novel and efficient ionic liquid supported synthesis of oligosaccharides", Tetrahedron Letters, May 1, 2006, vol. 47, No. 18, pp 3047-3050.

Huang et al., "An efficient approach for the synthesis of oligosaccharides using ionic liquid supported glycosylation", Carbohydrate Polymers, Jan. 1, 2011, vol. 83, No. 1, pp. 297-302.

Ishikawa et al., "Pure ionic liquid electrolytes compatible with a graphitized carbon negative electrode in rechargeable lithium-ion batteries", Journal of Power Sources, Nov. 8, 2006, vol. 162, No. 1, pp. 658-662.

Jaeger et al., "Preparation and Characterization of Cleavable Surfactants Based on a Silicon-Oxygen Bond", J.Org. Chem., 1988, vol. 53, No. 7, pp. 1577-1580, XP-002371545.

Koura et al., "Electrochemical Behavior of Graphite-Lithium Intercalation Electrode in AlCl3—EMIC—LiCl—SOCl2 Room-Temperature Molten Salt", Chemistry Letters, 2001, vol. 30, No. 12, pp. 1320-1321.

Lukevics et al., "Organosilicon Derivatives of Aminoalcohols", Russian Chemical Reviews, 1970, vol. 39, No. 11, pp. 953-963.

Lukevits et al., "Silyl Modification of Biologically Active Compounds. 3. Organosilicon Derivatives of Aminoalcohols in the Series of Tetrahydroquinoline, Tetrahydroisoquinoline, and Tetrahydrosilaisoquinoline", Chemistry of Heterocyclic Compounds, Jun. 1996, vol. 32, No. 6, pp. 682-688.

(56) References Cited

OTHER PUBLICATIONS

Maltsev et al., "O-TMS-α,α-diphenyl-(S)-prolinol Modified with an Ionic Liquid Moiety: A Recoverable Organocatalyst or the Asymmetric Michael Reaction between α,β-Enals and Dialkyl Malonates", European Journal of Organic Chemistry, Sep. 2009, vol. 30, pp. 5134-5137.

Maltsev et al., "Chiral Ionic Liquids Bearing O-Silylated α,α-Diphenyl (S)- or (R)-Prolinol Units: Recoverable Organocatalysts for Asymmetric Michael Addition of Nitroalkanes to α,β-Enals", European Journal of Organic Chemistry, May 2010, vol. 2010, No. 15, pp. 2927-2933.

Maltsev et al, "α,α-Diarylprolinol-derived chiral ionic liquids: recoverable organocatalysts for the domino reaction between α,β-enals and N-protected hydroxylamines", Tetrahedron: Asymmetry, 2010, vol. 21, pp. 2659-2670.

Matsumoto et al., "Fast cycling of Li/LiCoO2 cell with low-viscosity ionic liquids based on bis(fluorosulfonyl)imide [FSI]-", Journal of Power Sources, Oct. 6, 2006, vol. 160, No. 2, pp. 1308-1313.

Matsumoto et al., "Low Melting and Electrochemically Stable Ionic Liquids Based on Asymmetric Fluorosulfonyl (trifluoromethylsulfonyl)amide", Chemistry Letters, 2008, vol. 37, No. 10, pp. 1020-1021.

Niedermeyer et al., "Understanding siloxane functionalised ionic liquids", Physical Chemistry Chemical Physics, 2010, vol. 12, No. 8, pp. 2018-2029.

Omotowa et al., "Triazine-Based Polyfluorinated Triquaternary Liquid Salts: Synthesis, Characterization, and Application as Solvents in Rhodium(I)-Catalyzed Hydroformylation of 1-Octene", Organometallics, 2004, vol. 23, No. 4, pp. 783-791.

Pan et al, "SN2' Additions of Cuprates to Sulfone and Ester-Polarized Cyclopentenylic Systems", Tetrahedron, 1989, vol. 45, No. 2, pp. 467-478.

Paras et al., "The Enantioselective Organocatalytic 1,4-Addition of Electron-Rich Benzenes to α,β-Unsaturated Aldehydes", J. Am. Chem. Soc., 2002, vol. 124, No. 27, pp. 7894-7895.

Perrone et al., "2-(Quaternary Ammonio)-Methyl Penems", The Journal of Antibiotics, Sep. 1986, vol. 39, No. 9, pp. 1351-1355.

Shanmuganatnan et al., "Nickel and palladium complexes of enolatefunctionalised N-heterocyclic carbenes", Central European Journal of Chemistry, Oct. 2010, vol. 8, No. 5, pp. 992-998.

Tran et al., "Ionic catch and release oligosaccharide synthesis (ICROS)", Chemical Communications, 2011, vol. 47, No. 15, pp. 4526-4528.

Ue et al., "On the Anodic Stability of Organic Liquid Electrolytes", pp. 292-293.

Ui et al., "Development of non-flammable lithium secondary battery with ambient-temperature molten salt electrolyte Performance of binder-free carbon-negative electrode", Journal of Power Sources, Aug. 26, 2005, vol. 146, No. 1-2, pp. 698-702.

Holbrey et al., "Physicochemical Properties of Ionic Liquids: Melting Points and Phase Diagrams", Ionic Liquids in Synthesis, Second Edition. pp. 57-174.

Zhang et al., "Oligo(ethylene glycol)-functionalized disiloxanes as electrolytes for lithium-ion batteries" Journal of Power Sources, Sep. 15, 2010, vol. 195, No. 18, pp. 6062-6068.

Matsumoto, H., Kubota, K., Tsuxuki, S., & Sakaebe, H. (2011). "Charge and Discharge Property of Carbon Negative Electrode in Fluorosulfonyl(trifluoromethylsulfonyl) amide ionic liquids," Paper presented at the 52nd Japan Battery Symposia, Funabori, Tokyo.

Elzbieta Frackowiak et al, "Room-temperature Phosphonium Ionic Liquids for Supercapacitor Application", Appl. Phys. Lett. (86), 164104 (2005), AIP Publishing LLC.

A. Balducci et al, "The Use of Ionic Liquids as Solvent-free Green Electrolytes for Hybrid Supercapacitors" Appl. Phys. A (82), 627-632 (2006), Springer-Verlag 2005.

Beier et al., "Post-Synthesis Functionatization of (Meth)acrylate Based Monoliths via Electron Beam Triggered Graft Polymerization," Macromolecular Rapid Communication, (2008), vol. 29, Issue 11, pp. 904-909.

Crossland et al., "The Michael Reaction. Mechanism, Stereochemistry and a Synthetically Useful Modification," Acta Chemica Scandinavica, Series B. Organic Chemistry and Biochemistry, (1983), B 37, No. 1, pp. 21-25.

De Figueiredo et al., "Synthesis and Biological Evaluation of Potential Bisubstrate Inhibitors of Protein Farnesyltransferase. Design and Synthesis of Functionalized Imidazoles," Organic & Biomolecular Chmeistry, (2007), vol. 5, No. 20, pp. 3299-3309.

Kuksis et al., "Gas-Liquid Chromatographic Profiling of Plasma Lipids Using High-Temperature-Polarizable Capillary Columns," Journal of Chromatography, (1990), vol. 500, pp. 427-441.

Mathies et al., "Intermolecular Cross-Acyloin Reactions by Fluoride-Promoted Additions of O-Silyl Thiazolium Carbinols," Synlett, (2009), vol. 2009, No. 3, pp. 377-383.

Weng et al., "A Disiloxane-Functionalized Phosphonium-Based Ionic as Electrolyte for Lithium-ion Batteries," Chemical Communications, (2011), vol. 47, No. 43, pp. 11969-11971.

Zhang et al., "[2-(Hydroxyethoxy)ethyl]trimethylammonium iodide," Acta Crystallogtaphica Section E, (2007)vol. E63, pp. o2284-o2285.

Zhou et al., "Stereoselective Synthesis of 1-Aminocydopropanecarboxylic Acid Derivatives via Ylide Cyclopropanation of Dehydroamino Acid Derivatives," Chinese Journal of Chemistry, (2011), vol. 29, Issue 5, pp. 995-1000.

Office Action (Notification of Reason for Rejection) dated Sep. 9, 2016, by the Japanese Patent Office in corresponding Japanese Patent Application No. 2015-503720 and an English Translation of the Office Action. (16 pages).

* cited by examiner

IONIC COMPOUNDS HAVING A SILYLOXY GROUP

CROSS REFERENCE TO RELATED APPLICATIONS

This application claims benefit, under 35 U.S.C. § 119(e), of Canadian patent application CA 2 776 178, filed on Apr. 5, 2012. All documents above are incorporated herein in their entirety by reference.

FIELD OF THE INVENTION

The present invention relates generally to ionic compounds and ionic liquids. More particularly, the present invention relates to ionic liquids bearing a silyloxy group that can be used in electrochemical cells.

BACKGROUND OF THE INVENTION

Electrolytes in modern electrochemical appliances like lithium ion batteries, electrochromic devices and capacitors are made from various organic solvents containing conductive lithium salts like lithium tetrafluoroborate, lithium hexafluorophosphate, lithium bisoxalatoborate, lithium triflate, lithium bistriflylamide, etc. Such organic solvents (like alkyl carbonates, acetonitrile, N-methyl-2-pyrrolidone, γ-butyrolactone and many others) have a serious disadvantage. They can indeed ignite and, in the worst cases, cause an overheated appliance to explode and start a fire.

Attempts have been made to circumvent this disadvantage of organic solvents by using ionic liquids (IL) as solvents, as described for example in U.S. Pat. Nos. 6,365,301 and 6,365,068, U.S. Patent Application Nos 2008/0266642 and 2009/0045373, and PCT publication No. WO 2009/013046.

Existing ionic liquids however do not solve all the problems associated with the manufacturing of electrochemical appliances, especially high power lithium or lithium ion batteries. In batteries, several electrode materials are used, so solvents or electrolytes for use with these materials should exhibit high thermal, electrochemical and chemical stabilities.

Tetraalkylammonium salts, including cyclic analogs like piperidinium, morpholinium, pyrrolidinium and azepanium, have the widest electrochemical window.[1] The most used IL for electronic applications are those containing bis(trifluoromethanesulfonyl)amide anions (TFSA or TFSI), which have oxidation stability close to that of $BF_4^-$ and $PF_6^{-2}$ and exhibit the widest liquid range.

Electrochemical intercalation of lithium into graphite anodes in 1-ethyl-3-methylimidazolium (EMI) based ionic liquids has aroused interest because these ionic liquids have low viscosities and high conductivities. However, these ionic liquids have narrow electrochemical windows (ca 4.2 V). Imidazolium cations are prone to being reduced at the electrode/electrolyte interface when the carbon electrode is polarized to 0.7 V vs. Li/Li+. The strong decomposition reaction of the cations prevents the formation of $LiC_6$ compounds. The addition of a solvent may however stabilize and protect the interface between a carbon negative electrode and the ionic liquid phase against an undesirable irreversible reaction with the ionic liquid component. N. Koura, and coworkers demonstrated the formation $LiC_6$ compound in LiCl-EMICl—$AlCl_3$ ionic electrolyte containing $SOCl_2$.[3] Satisfactory results were obtained for various carbonaceous materials. Holzapfel et al. presented the lithium intercalation into an artificial graphite in 1 M solution of LiPF6 in 1-ethyl-3-methyl imidazolium bis(trifluoromethylsulfonyl)imide (EMI-TFSI) containing 5 wt % of vinylene carbonate (VC) as an additive.[4]

However, despite many attempts, no pure ionic liquid providing reversible charging-discharging of a graphitized negative electrode at ambient temperature without any additives has been reported yet. The practical application of the imidazolium derivatives into lithium ion batteries is difficult. Lithium ion batteries using these ionic liquids suffer from relatively small voltage. Graphite material, which is used as a low potential anode material in lithium ion batteries, can cause reduction of unsaturated IL and consequent decomposition, especially of imidazolium and pyridinium based IL. In some cases, the intercalation of cations of IL has caused the exfoliation of graphite layer.

Recently there have been some reports on ionic liquid electrolytes based on bis(fluorosulfonyl)imide (FSI) for rechargeable Li batteries. In particular, FSI-based electrolytes containing Li-ion exhibited practical ionic conductivity, and a natural graphite/Li cell with FSI-based electrolytes containing Li bis(trifluoromethanesulfonyl)imide (LiTFSI) showed cycle performance without any solvent, using 1-ethyl-3-methylimidazolium (EMIm)-FSI and EMIm-TFSI[5] and using IL based on bis(fluorosulfonyl)imide (FSI)[6] as anion and 1-ethyl-3-methylimidazolium (EMI) and N-methyl-N-propylpyrrolidinium (Py13) as cations. It has further been observed that IL with TFSI anion cannot be used alone with graphite electrodes, because only very low capacities could be reached. The use of stabilizing agents like lithium bis(fluorosulfonyl)amide (FSI) in electrolyte and the preparation of IL containing fluorosulfonyl trifluoromethanesulfonylamide (FTFSI) was proposed[7], but these solutions are economically not viable due to the high cost of LiFSI salt and complicated synthesis method.

Choline-like compounds, possessing 2-hydroxyethyl group, are able to form deep eutectic mixtures, but are not suitable for use in electrochemical appliances with high operating voltage because of the presence of labile acidic hydroxyl groups. The methylation of hydroxyl groups in choline like compound may however improve their stability.

Improvement of stability of various oligoethylene glycols was achieved by the protection of terminal hydroxyl group by various siloxy groups, such as trimethylsilyl group.[8] The preparation of silylated choline compounds has also been disclosed.[9]

JP 2010-095473A discloses ionic compounds containing trialkylsilyl moieties and their use as antistatic agents for low surface energy polymers (PTFE). The prepared antistatic agents were mostly solid at room temperature.

There is thus a need for novel ionic compounds or ionic liquids for use in electrolytes and electrochemical cells.

SUMMARY OF THE INVENTION

In accordance with the present invention, there is provided:

1. An ionic compound comprising an anion and a cation, the ionic compound having attached thereto at least one silyloxy group.
2. The ionic compound of item 1 being an ionic liquid.
3. The ionic compound of item 1 or 2 having attached thereto one silyloxy group.

4. The ionic compound of item 3 being of formula (I):

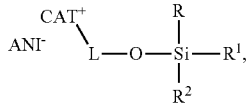

wherein:
CAT$^+$ represents said cation, the cation containing a positively singled charged atom, which is nitrogen, phosphorus or sulfur;
R, R$^1$ and R$^2$ are independently C$_1$-C$_8$ alkyl, alkenyl or alkynyl groups,
L represents a linker, and
ANI$^-$ represents said anion.

5. The ionic compound of item 4, wherein the positively charged atom is nitrogen.
6. The ionic compound of item 4 or 5, wherein R, R$^1$ and R$^2$ are independently C$_1$-C$_8$ alkyl or alkenyl groups.
7. The ionic compound of item 6, wherein R, R$^1$ and R$^2$ are independently C$_1$-C$_4$ alkyl or alkenyl groups.
8. The ionic compound of item 7, wherein R, R$^1$ and R$^2$ are independently C$_1$-C$_4$ alkyl groups.
9. The ionic compound of item 8, wherein R, R$^1$ and R$^2$ are independently C$_1$-C$_2$ alkyl groups.
10. The ionic compound of item 9, wherein R, R$^1$ and R$^2$ each represent methyl.
11. The ionic compound of any one of items 1 to 10, wherein L is a C$_1$-C$_{12}$ alkylene, alkenylene, or alkynylene group, optionally comprising one or more ether function, and optionally substituted with one or more halogen atoms.
12. The ionic compound of item 11, wherein L together with the oxygen atom to which it is attached form one or more alkyleneoxy, alkenyleneoxy, or alkynyleneoxy group.
13. The ionic compound of item 12, wherein L together with the oxygen atom to which it is attached form one or more alkyleneoxy group.
14. The ionic compound of item 13, wherein L together with the oxygen atom to which it is attached form one or more ethyleneoxy group.
15. The ionic compound of item 14, wherein L together with the oxygen atom to which it is attached form one or two ethyleneoxy group.
16. The ionic compound of item 11, wherein L is a C$_1$-C$_{12}$ alkylene group.
17. The ionic compound of item 16, wherein L is a C$_2$-C$_6$ alkylene group.
18. The ionic compound of item 17, wherein L is a C$_2$ alkylene group.
19. The ionic compound of item 18, wherein L is —CH$_2$—CH$_2$—.
20. The ionic compound of any one of items 1 to 19, wherein the cation is of formula (IIa), (IIb) or (IIc):

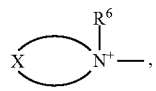

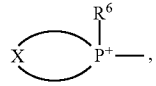

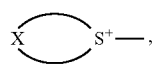

wherein R$^3$, R$^4$ and R$^5$ are independently C$_1$-C$_{16}$ alkyl, alkenyl, or alkynyl groups.

21. The ionic compound of item 20, wherein the cation is of formula (IIa).
22. The ionic compound of item 20 or 21, wherein R$^3$, R$^4$ and R$^5$ are independently C$_1$-C$_6$ alkyl or alkenyl groups.
23. The ionic compound of item 22, wherein R$^3$, R$^4$ and R$^5$ are independently C$_1$-C$_4$ alkyl groups.
24. The ionic compound of item 23, wherein R$^3$, R$^4$ and R$^5$ are independently C$_1$-C$_3$ alkyl groups.
25. The ionic compound of item 24, wherein R$^3$, R$^4$ and R$^5$ each represent —CH$_3$.
26. The ionic compound of item 24, wherein R$^3$, R$^4$ and R$^5$ each represent —CH$_2$CH$_3$.
27. The ionic compound of item 24, wherein R$^3$ and R$^4$ each represent —CH$_3$ and R$^5$ represent —CH$_2$CH$_3$.
28. The ionic compound of item 24, wherein R$^3$ represent —CH$_3$ and R$^4$ and R$^5$ each represent —CH$_2$CH$_3$.
29. The ionic compound of any one of items 1 to 19, wherein the cation is of formula (IIIa), (IIIb), or (IIIc):

(IIIa)

(IIIb)

(IIIc)

wherein:
X is a combination of one or more of —CH$_2$—, —O—, and —N(CH$_3$)— so that CAT$^+$ is a cation of the azetidinium, pyrrolidinium, pyrazolidinium, imidazolidinium, piperidinium, azepanium, morpholinium, isomorpholinium, piperazinium, hexahydropyrimidinium, or hexahydropyridazinium type; and
R$^6$ is a C$_1$-C$_{16}$ alkyl, alkenyl, or alkynyl group.

30. The ionic compound of item 29, wherein CAT$^+$ is of formula (IIIa).
31. The ionic compound of item 29 or 30, wherein X is —CH$_2$CH$_2$CH$_2$CH$_2$—.
32. The ionic compound of any one of items 29 to 31, wherein R$^6$ is a C$_1$-C$_8$ alkyl or alkenyl group.
33. The ionic compound of item 32, wherein R$^6$ is a C$_1$-C$_4$ alkyl group.
34. The ionic compound of item 33, wherein R$^6$ is —CH$_3$.
35. The ionic compound of any one of items 1 to 19, wherein the cation is of formula (IVa), (IVb), or (IVc):

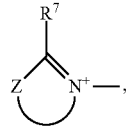

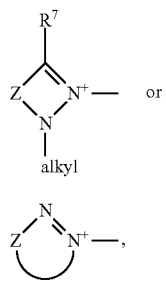

wherein:
Z is a combination of one or more of —CH$_2$—, —CH=, —O—, —N(alkyl)- and —N= so that CAT$^+$ is a cation of the azetinium, 3,4-dihydro-2H-pyrolium, pyridinium, azepinium, pyrimidinium, piperazinium, imidazolium, pyrazolium type, oxazinium, or triazolium, and
R$^7$ is hydrogen or alkyl.

36. The ionic compound of item 35, wherein Z is —N(alkyl)-CH=CH—.
37. The ionic compound of item 36, wherein Z is —N(CH$_3$)—CH=CH—.
38. The ionic compound of any one of items 35 to 37, wherein R$^7$ is hydrogen.
39. The ionic compound of any one of items 35 to 37, wherein R$^7$ is —CH$_3$.
40. The ionic compound of any one of items 1 to 39, wherein the anion is:
a halide,
perchlorate,
hexafluorophosphate,
tris(pentafluoroethyl)trifluorophosphate,
tetrafluoroborate,
trifluoromethyltrifluoroborate,
pentafluoroethyltrifluoroborate,
heptafluoropropyltrifluoroborate,
nonafluorobutyltrifluoroborate,
trifluoromethanesulfonate,
trifluoroacetate,
bis(fluorosulfonyl)amide,
or a sulfonylamide of formula (V):

wherein A is F—SO$_2$—CF$_3$—SO$_2$—, C$_2$F$_5$—SO$_2$—, C$_3$F$_7$—SO$_2$—, C$_4$F$_9$—SO$_2$—, or CF$_3$—C(=O)—; and B is —F, —CF$_3$, —C$_2$F$_5$, —C$_3$F$_7$, —C$_4$F$_9$.

41. The ionic compound of item 43, wherein the sulfonylamide of formula (V) is:
bis(trifluoromethanesulfonyl)amide,
bis(pentafluoroethylsulfonyl)amide,
bis(heptafluoropropylsulfonyl)amide,
bis(nonafluorobutylsulfonyl)amide,
N-trifluoroacetyl-fluorosulfonylamide,
N-trifluoroacetyl-trifluoromethanesulfonylamide,
N-trifluoroacetyl-pentafluoroethylsulfonyl amide,
N-trifluoroacetyl-heptafluoropropylsulfonylamide,
N-trifluoroacetyl-nonafluorobutylsulfonylamide,
N-fluorosulfonyl-trifluoromethanesulfonylamide,
N-fluorosulfonyl-pentafluoroethylsulfonylamide,
N-fluorosulfonyl-heptafluoropropylsulfonylamide,
N-fluorosulfonyl-nonafluorobutylsulfonylamide,
N-trifluoromethanesulfonyl-pentafluoroethylsulfonyl amide,
N-trifluoromethanesulfonyl-heptafluoropropylsulfonylamide, or
N-trifluoromethanesulfonyl-nonafluorobutylsulfonylamide.

42. The ionic compound of item 40 or 41, wherein the anion is chloride, bis(fluorosulfonyl)amide, bis(trifluoromethanesulfonyl)amide, or N-fluorosulfonyl-trifluoromethanesulfonylamide.
43. The ionic compound of item 42, wherein the anion is bis(fluorosulfonyl)amide, bis(trifluoromethanesulfonyl)amide, or N-fluorosulfonyl-trifluoromethanesulfonylamide.
44. The ionic compound of item 43, wherein the anion is bis(trifluoromethanesulfonyl)amide.
45. The ionic compound of item 1 comprising one single charged cation and one singled anion, the ionic compound being an ionic liquid and being of formula:

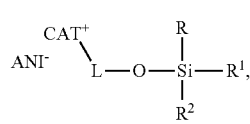

wherein:
CAT$^+$ represents said cation, the cation containing a positively singled charged nitrogen atom, the cation being of formula (IIa):

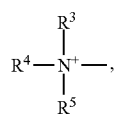

wherein R$^3$, R$^4$ and R$^5$ are independently C$_1$-C$_6$ alkyl groups;
R, R$^1$ and R$^2$ are independently C$_1$-C$_4$ alkyl groups;
L represents a linker and together with the oxygen atom to which it is attached form one or two ethyleneoxy groups; and
ANI$^-$ represents said anion, which is a sulfonylamide of formula (V):

wherein A is F—SO$_2$—CF$_3$—SO$_2$—, C$_2$F$_5$—SO$_2$—, C$_3$F$_7$—SO$_2$—, C$_4$F$_9$—SO$_2$—; and B is —F, —CF$_3$, —C$_2$F$_5$, —C$_3$F$_7$, —C$_4$F$_9$.

46. The ionic compound of item 45, wherein R$^3$, R$^4$ and R$^5$ are independently C$_1$-C$_3$ alkyl groups.
47. The ionic compound of item 45 or 46, wherein R, R$^1$ and R$^2$ are independently C$_1$-C$_2$ alkyl groups.
48. The ionic compound of any one of items 48 to 47, wherein the anion is bis(fluorosulfonyl)amide, bis(trifluoromethanesulfonyl)amide, or N-fluorosulfonyl-trifluoromethanesulfonylamide
49. The ionic compound of item 1 being:

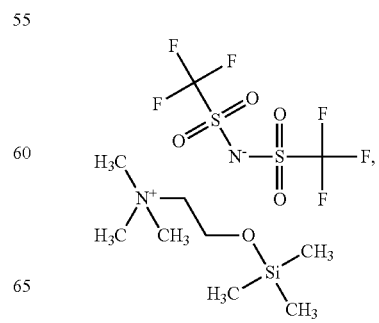

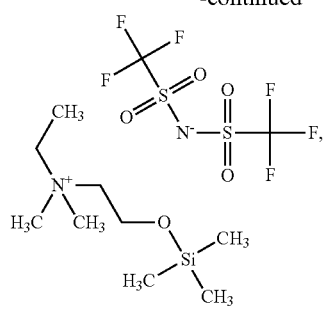
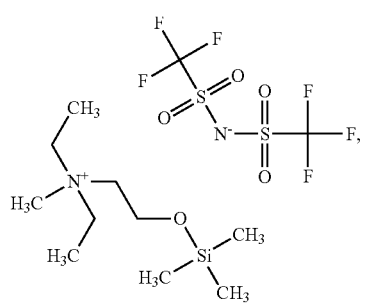
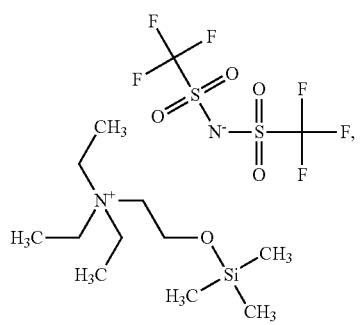
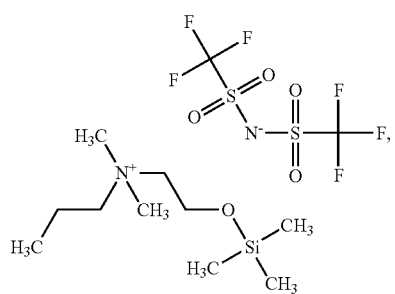
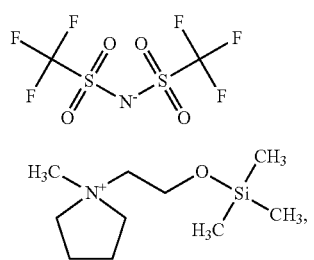
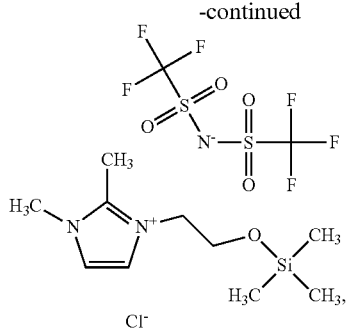
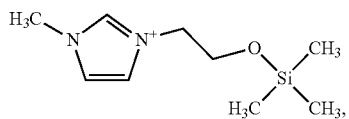
Cl⁻
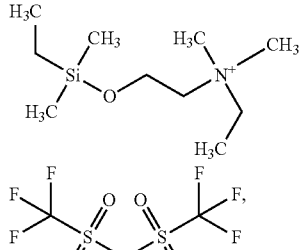
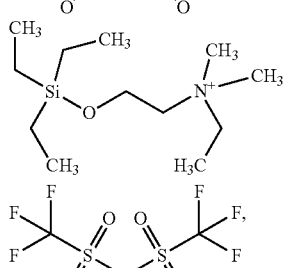
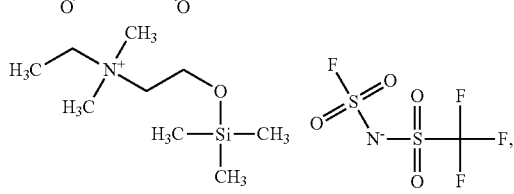
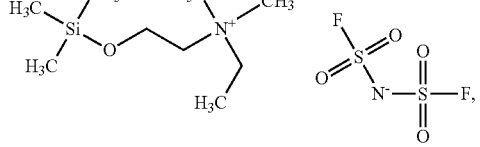
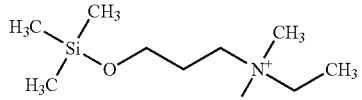
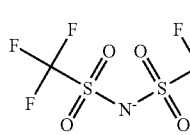
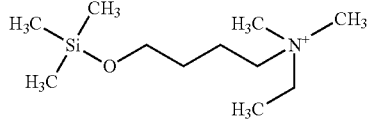

-continued
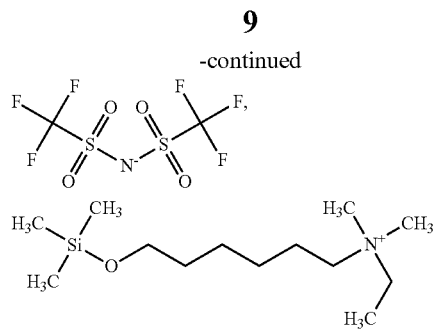
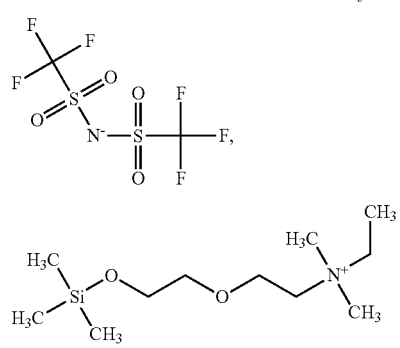
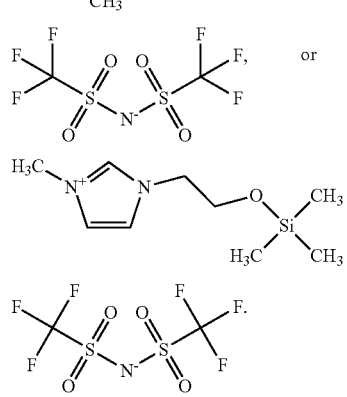
or
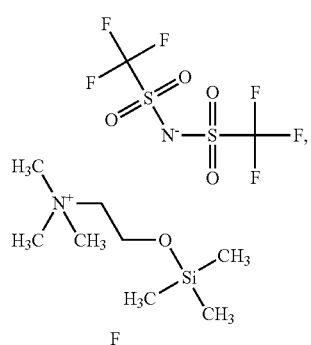
50. The ionic compound of item 1 being:
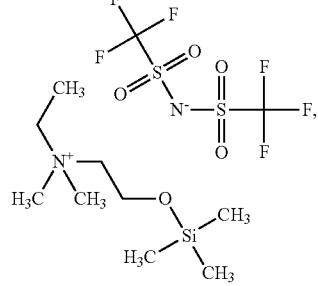
-continued
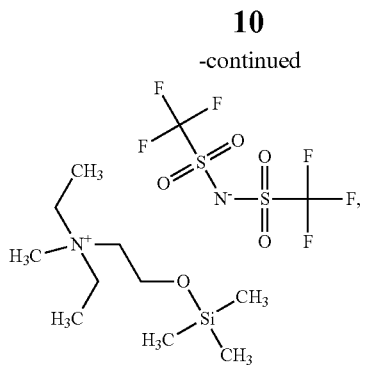
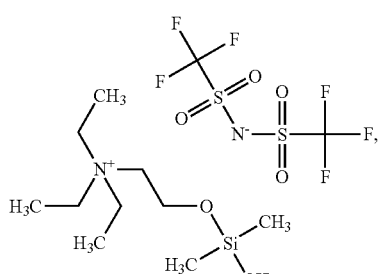
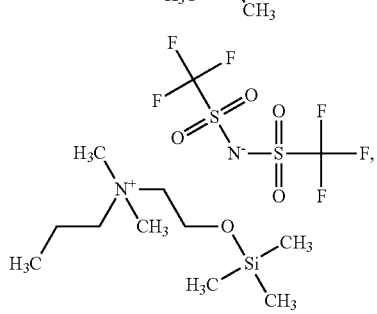
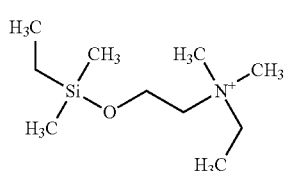
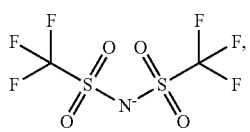
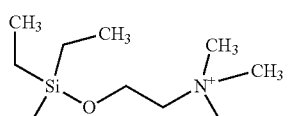
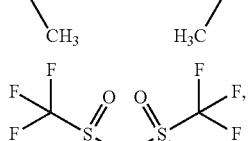
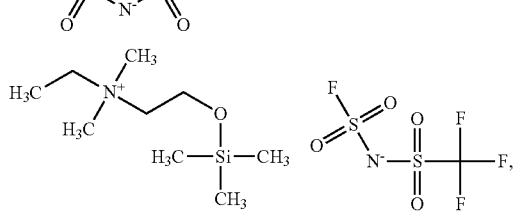

-continued

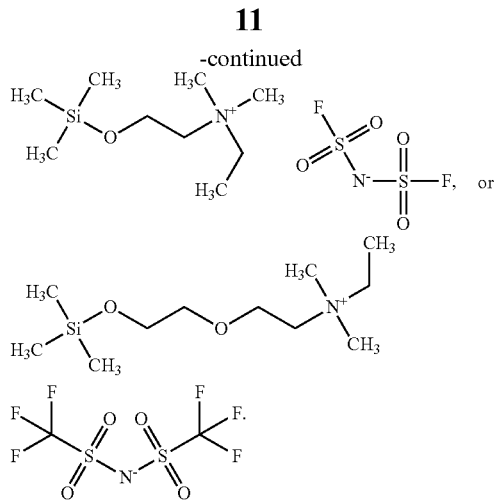

51. An electrolyte comprising at least one ionic compound as defined in any one of items 1 to 50 and a conducting salt.
52. The electrolyte of item 51 further comprising an organic solvent.
53. The electrolyte of item 52, wherein the organic solvent is a polar organic solvent.
54. The electrolyte of any one of items 51 to 53, further comprising an unsaturated carbonate.
55. An electrochemical cell comprising an anode, a cathode, and an electrolyte as defined in any one of items 51 to 54.
56. The electrochemical cell of item 55 being part of electrochemical system, such as a battery, a capacitor or an electrochromic device.

BRIEF DESCRIPTION OF THE DRAWINGS

In the appended drawings.

DETAILED DESCRIPTION OF THE INVENTION

Ionic Compounds

Figure 1:
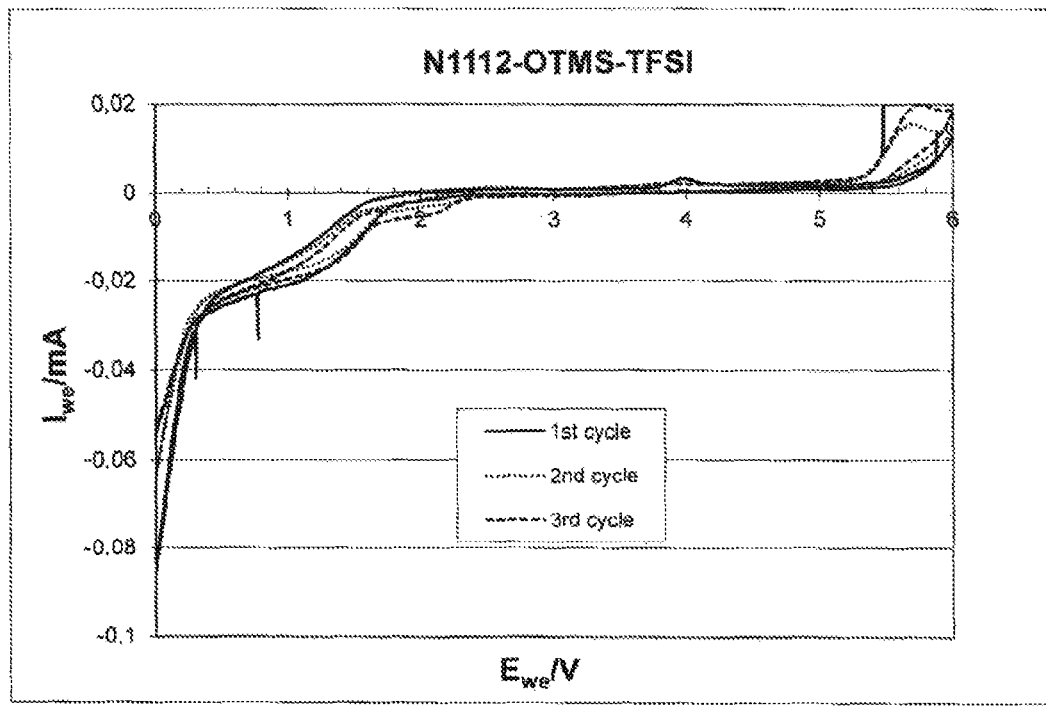
FIG. 1 shows the cyclic voltametry of N1112-OTMS-TFSI.

Turning now to the invention in more details, there is provided an ionic compound having attached thereto at least one silyloxy group. In embodiment, the ionic compound comprises one such silyloxy group.

Herein, "ionic compound" refer to a chemical compound consisting of at least two separated molecules or atoms which bear opposite electrostatic charge and are, in the solid state, held together by ionic bonds, i.e. a type of chemical bond formed through an electrostatic attraction between oppositely charged ions. In ionic compounds the sum of all electrostatic charges is equal to zero. In these ionic compounds, the positively charged molecule or atom is referred to as a cation and the negatively charged molecule or atom is referred to as an anion. Each cation and anion bears at least one electrostatical charge, but can also be multiple charged. As a result, an ionic compound can comprise one or more cations and/or one or more anions. When dissolved or melted, the ionic compound dissociates into freely movable cations and anions, the consequence is electrical conductivity of such solutions or melts.

Herein, a "silyloxy" group is any univalent radical of general formula (R')(R'')(R''')Si—O—. In embodiments, the silyloxy group is a trialkylsilyloxy group (i.e. a compound of the above formula in which R', R'' and R''' are all alkyl groups).

The ionic compounds of the invention are ionic liquids (IL). Herein, "ionic liquid" refers to an ionic compound that is in a molten state at low temperature. Thus, the ionic liquid should have a low melting point, for example a melting point below 100° C., preferably below 75° C., more preferably below 50° C., yet more preferably below 25° C. and most preferably below room temperature. Thus, in embodiments, the ionic compound of the invention is molten at a temperature below 100° C., for example at room temperature.

There are many known classes of ionic liquids. The ionic compound of the invention can be any ionic liquid known in the art to which at least one silyloxy group has been attached. It may also be any derivative of these ionic liquids. Non-limiting examples of derivatives of ionic liquids include cations where substituents or side chains have been added. Side chains can include alkyl, alkoxy, and alkoxyalkyl chains.

The insertion of a silyloxy group allows producing ionic liquids with advantageous thermal, electrochemical and/or chemical stabilities. This makes them suitable for use in many applications, such as batteries, including lithium ions batteries, electrochromic devices, and capacitors. Further, as shown in the Examples below, many ionic compounds of the invention have fairly large electrochemical windows and/or have good oxidation stability and/or good reduction stability and/or have good compatibility with electrodes, including graphite electrodes. In embodiments, especially those containing a TFSI or FSI anion, electrolytes containing the ionic compound of the invention have good compatibility with graphite electrodes, such as those used in lithium ion batteries. These can, in embodiments, provide reversible charging-discharging of a graphitized negative electrode at ambient temperature without or with reduced decomposition of the ionic compound, and with the formation of an adequate passivation layer around the graphite particles of the electrode.

In embodiments, the ionic compounds comprise only one anion and one anion. In more specific embodiments, the ionic compound comprises only one single charged anion and one single charged anion.

In embodiments of the ionic compounds or ionic liquid of the invention, the silyloxy group is attached to the cation of the ionic liquid via covalent bonds. More specifically, the silyloxy group can be attached through a linker.

In embodiments, the ionic compound is of formula (I):

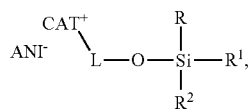

wherein:
CAT$^+$ is a cation containing a positively single charged atom which is nitrogen, phosphorus or sulfur, preferably nitrogen;
R, R$^1$ and R$^2$ are independently C$_1$-C$_8$ alkyl, alkenyl or alkynyl groups, preferably C$_1$-C$_8$ alkyl or alkenyl groups, more preferably C$_1$-C$_4$ alkyl or alkenyl groups, even more preferably C$_1$-C$_4$ alkyl groups, yet more preferably C$_1$-C$_2$ alkyl groups, and most preferably methyl;
L represents a linker, and
ANI$^-$ represents a single charged anion.

In embodiments, L is a C$_1$-C$_{12}$ alkylene, alkenylene, or alkynylene group, optionally comprising one or more ether function, and optionally substituted with one or more halogen atoms. In further embodiments, L is a C$_1$-C$_{12}$ alkylene group, preferably a C$_2$-C$_6$ alkylene group, more preferably a C$_2$-C$_4$ alkylene group, even more preferably C$_2$ or C$_6$ alkylene group, and most preferably —CH$_2$—CH$_2$—.

In embodiments, L forms together with the oxygen atom to which it is attached (i.e. the oxygen atom of the silyloxy group) one or more alkyleneoxy, alkenyleneoxy, or alkynyleneoxy group, preferably one or more alkyleneoxy group, more preferably one or more ethyleneoxy group (such as 1, 2, 3, 4, 5, or 6 such groups) and yet more preferably one or two ethyleneoxy groups. For certainty, where there are more than one such groups, these groups are to be understood as attached to one another in a chain. For example, "two propyleneoxy groups" is a moiety of formula —CH$_2$CH$_2$CH$_2$—O—CH$_2$CH$_2$CH$_2$—O—, the underlined oxygen atom being that belonging to the silyloxy group.

It should be noted that some of the above embodiments overlap. For example, an ionic compound where L being a —CH$_2$—CH$_2$— is the same compound as that where L together with the oxygen atom to which it is attached forms one ethylenoxy group.

In embodiments, the cation of the ionic compound (identified as CAT$^+$ in formula (I) above) is of formula (IIa), (IIb), or (IIc):

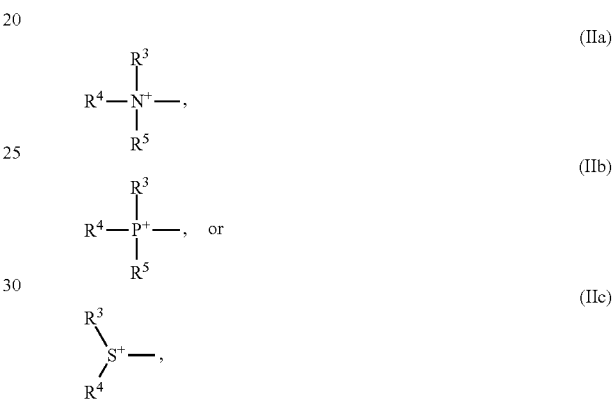

preferably of formula (IIa),
wherein R$^3$, R$^4$ and R$^5$ are independently C$_1$-C$_{16}$ alkyl, alkenyl, or alkynyl groups, preferably C$_1$-C$_8$ alkyl or alkenyl groups, and more preferably C$_1$-C$_4$ alkyl groups, and even more preferably C$_1$-C$_3$ alkyl groups. Most preferably, 0, 1, 2 or all 3 of R$^3$, R$^4$ and R$^5$ is/are methyl (—CH$_3$), while the rest of them is/are ethyl (—CH$_2$CH$_3$).

In embodiments, the cation is of formula (IIIa), (IIIb), or (IIIc):

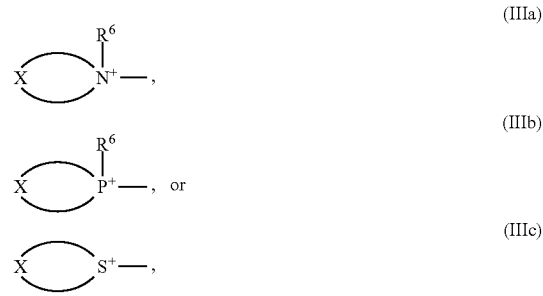

preferably of formula (IIIa),
wherein R$^6$ is a C$_1$-C$_{16}$ alkyl, alkenyl, or alkynyl group, preferably a C$_1$-C$_8$ alkyl or alkenyl group, more preferably a C$_1$-C$_4$ alkyl group, and most preferably a methyl group; and
wherein X is a combination of one or more of —CH$_2$—, —O—, and —N(alkyl)- so that CAT$^+$ is a cation of the azetidinium, pyrrolidinium, pyrazolidinium, imidazolidinium, piperidinium, azepanium, morpholinium, isomorpholinium, piperazinium, hexahydropyrimidinium, and hexahydropyridazinium type.

In embodiments, the alkyl in —N(alkyl)- is a $C_{1-6}$ alkyl, preferably $C_{1-6}$ alkyl, more preferably methyl. Embodiments where —N(CH$_3$)— is —N(CH$_3$)— are usually advantageous in regard of their melting points and viscosities.

Herein, a cation of the azetidinium type is a cation of formula (IIIa) above wherein X is —CH$_2$—CH$_2$—CH$_2$—, or in other words, a cation of formula:

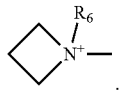

It also refers, by analogy, to cations of formula (IIIb) and (IIIc) wherein X is —CH$_2$—CH$_2$—CH$_2$—.

Herein, a cation of the pyrrolidonium type is a cation of formula (IIIa) above wherein X is —CH$_2$—C(=O)—CH$_2$—CH$_2$— or the equivalent —CH$_2$—CH$_2$—C(=O)—CH$_2$—, or in other words, a cation of formula:

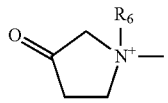

It also refers, by analogy, to cations of formula (IIIb) and (IIIc) wherein X is —CH$_2$—C(=O)—CH$_2$—CH$_2$—.

Herein, a cation of the pyrazolidinium type is a cation of formula (IIIa) above wherein X is —N(alkyl)-CH$_2$—CH$_2$—CH$_2$— (or the equivalent —CH$_2$—CH$_2$—CH$_2$—N(alkyl)-), or in other words, when alkyl is methyl, a cation of formula:

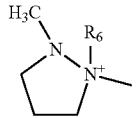

It also refers, by analogy, to cations of formula (IIIb) and (IIIc) wherein X is —N(alkyl)-CH$_2$—CH$_2$—CH$_2$—.

Herein, a cation of the imidazolidinium type is a cation of formula (IIIa) above wherein X is —CH$_2$—N(alkyl)-CH$_2$—CH$_2$— (or the equivalent —CH$_2$—CH$_2$—N(alkyl)-CH$_2$—), or in other words, when alkyl is methyl, a cation of formula:

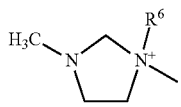

It also refers, by analogy, to cations of formula (IIIb) and (IIIc) wherein X is —CH$_2$—N(alkyl)-CH$_2$—CH$_2$.

Herein, a cation of the piperidinium type is a cation of formula (IIIa) above wherein X is —CH$_2$—CH$_2$—CH$_2$—CH$_2$—, or in other words, a cation of formula:

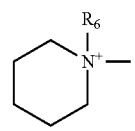

It also refers, by analogy, to cations of formula (IIIb) and (IIIc) wherein X is —CH$_2$—CH$_2$—CH$_2$—CH$_2$—CH$_2$—.

Herein, a cation of the azepanium type is a cation of formula (IIIa) above wherein X is —CH$_2$—CH$_2$—CH$_2$—CH$_2$—CH$_2$—CH$_2$—, or in other words, a cation of formula:

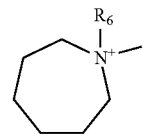

It also refers, by analogy, to cations of formula (IIIb) and (IIIc) wherein X is —CH$_2$—CH$_2$—CH$_2$—CH$_2$—CH$_2$—CH$_2$—.

Herein, cations of the morpholinium or isomorpholinium types are cations of formula (IIIa) above wherein X is —CH$_2$—CH$_2$—O—CH$_2$—CH$_2$ or —CH$_2$—O—CH$_2$—CH$_2$—CH$_2$ (or the equivalent —CH$_2$—CH$_2$—CH$_2$—O—CH$_2$—), or in other words, cations of formula:

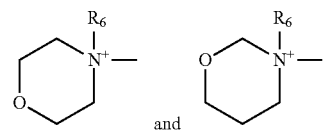

and

It also refers, by analogy, to cations of formula (IIIb) and (IIIc) wherein X is —CH$_2$—CH$_2$—O—CH$_2$—CH$_2$— or —CH$_2$—O—CH$_2$—CH$_2$—CH$_2$—.

Herein, cations of the piperazinium, hexahydropyrimidinium and hexahydropyridazinium types are cations of formula (IIIa) above wherein X is —CH$_2$—CH$_2$—N(alkyl)-CH$_2$—CH$_2$—, —CH$_2$—N(alkyl)-CH$_2$—CH$_2$—CH$_2$— (or the equivalent —CH$_2$—CH$_2$—CH$_2$—N(alkyl)-CH$_2$), and N(alkyl)-CH$_2$—CH$_2$—CH$_2$—CH$_2$— (or the equivalent CH$_2$—CH$_2$—CH$_2$—CH$_2$—N(alkyl)-), respectively, or in other words, when alkyl is methyl, cations of formula:

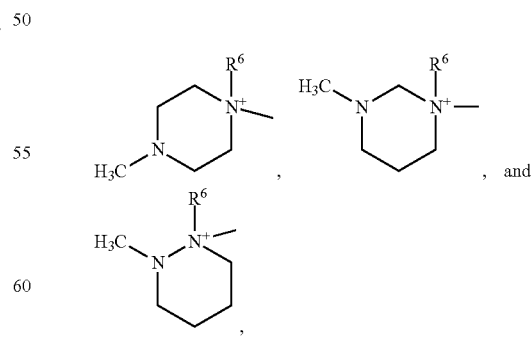

respectively. It also refers, by analogy, to cations of formula (IIIb) and (IIIc) wherein X is —CH$_2$—CH$_2$—N(alkyl)-CH$_2$—CH$_2$—, —CH$_2$—N(alkyl)-CH$_2$—CH$_2$—CH$_2$—, or N(alkyl)-CH$_2$—CH$_2$—CH$_2$—CH$_2$—.

In more specific embodiments, the cation is of formula (IIIa) and X is —CH$_2$—CH$_2$—CH$_2$CH$_2$—. In other words, the cation is of formula:

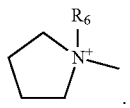

In more specific embodiments, R$_6$ in this last formula is methyl.

In embodiments, the cation of the ionic compound is of formula (IVa), (IVb), or (IVc):

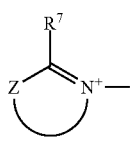
(IVa)

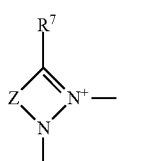
(IVb)

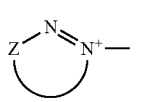
(IVc)

wherein Z is a combination of one or more of —CH$_2$—, —CH=, —O—, —N(alkyl)- and —N= so that CAT$^+$ is a cation of the azetinium, 3,4-dihydro-2H-pyrolium, pyridinium, azepinium, pyrimidinium, pirazinium, imidazolium, pyrazolium, oxazinium, or triazolium (1,2,3 or 1,2,4) type, and R$^7$ is hydrogen or alkyl, preferably hydrogen or C$_{1-6}$ alkyl, more preferably hydrogen or methyl, most preferably hydrogen.

In embodiments, in Z and/or in formula (IVb), the alkyl group is C$_{1-6}$ alkyl, preferably C$_{1-6}$ alkyl, more preferably methyl.

Herein, a cation of the azetinium type is a cation of formula (IVa) above wherein Z is —CH=CH—, or in other words, a cation of formula:

It also refers, by analogy, to similar cations wherein R$^7$ is alkyl.

Herein, a cation of the 3,4-dihydro-2H-pyrolium type is a cation of formula (IVa) above wherein Z is —CH$_2$—CH$_2$—CH$_2$— or in other words, a cation of formula:

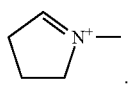

It also refers, by analogy, to similar cations wherein R$^7$ is alkyl.

Herein, a cation of the pyridinium type is a cation of formula (IVa) above wherein Z is —CH=CH—CH=CH—, or in other words, a cation of formula:

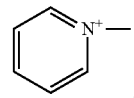

It also refers, by analogy, to similar cations wherein R$^7$ is alkyl.

Herein, a cation of the azepinium type is a cation of formula (IVa) above wherein Z is —CH=CH—CH=CH—CH$_2$—, or in other words, a cation of formula:

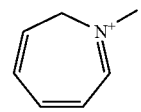

It also refers, by analogy, to similar cations wherein R$^7$ is alkyl.

Herein, a cation of the pyrimidinium type is a cation of formula (IVa) above wherein Z is —N=CH—CH=CH—, or in other words, a cation of formula:

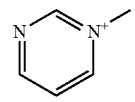

It also refers, by analogy, to similar cations wherein R$^7$ is alkyl.

Herein, a cation of the pirazinium type is a cation of formula (IVa) above wherein Z is —CH=N—CH=CH—, or in other words, a cation of formula:

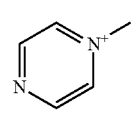

It also refers, by analogy, to similar cations wherein R$^7$ is alkyl.

Herein, a cation of the imidazolium type is a cation of formula (IVa) above wherein Z is —N(alkyl)-CH=CH—, or in other words, a cation of formula:

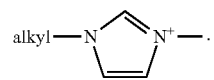

It also refers, by analogy, to similar cations wherein R$^7$ is alkyl.

Herein, a cation of the pyrazolium type is a cation of formula (IVb) above wherein Z is —CH=CH—, or in other words, a cation of formula:

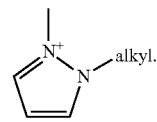

It also refers, by analogy, to similar cations wherein R$^7$ is alkyl.

Herein, cations of the oxazinium type are cations based on any one of the 14 known oxazine isomers. This include cations of formula (IVa) above wherein Z is —CH=CH—

CH$_2$—O—, —CH$_2$—CH=CH—O—, =CH—CH$_2$—CH$_2$—O—, —O—CH$_2$—CH=CH—, —O—CH=CH—CH$_2$—, —CH=CH—O—CH$_2$—, =CH—CH$_2$—O—CH$_2$—, —CH$_2$—O—CH=CH—, and =CH—O—CH$_2$—CH$_2$—. It also refers, by analogy, to similar cations wherein R$^7$ is alkyl.

Herein, a cation of the 1,2,4-triazolium type is a cation of formula (IVa) above wherein Z is —N(alkyl)-N=CH—, or in other words, a cation of formula:

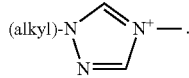

It also refers, by analogy, to similar cations wherein R$^7$ is alkyl.

Herein, a cation of the 1,2,3-triazolium type is a cation of formula (IVc) above wherein Z is —N(alkyl)-CH=CH—, or in other words, a cation of formula:

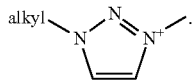

In specific embodiment, Z in general formula (IVa) is —N(alkyl)-CH=CH— and more specifically —N(CH$_3$)—CH=CH—, while R$^7$ is H or CH$_3$. In other words, the cation is of formula

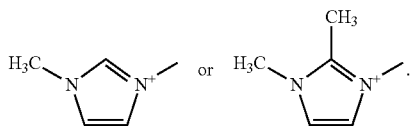

In embodiments, the anion of the ionic compound (identified as ANI$^-$ in formula (I) above) is a halide, perchlorate, hexafluorophosphate, tris(pentafluoroethyl)trifluorophosphate, tetrafluoroborate, trifluoromethyltrifluoroborate, pentafluoroethyltrifluoroborate, heptafluoropropyltrifluoroborate, nonafluorobutyltrifluoroborate, trifluoromethanesulfonate, trifluoroacetate, or a sulfonylamide of formula (V):

 (V), wherein A is F—SO$_2$—CF$_3$—SO$_2$—, C$_2$F$_5$—SO$_2$—, C$_3$F$_7$—SO$_2$—, C$_4$F$_9$—SO$_2$—, or CF$_3$—C(=O)—; and B is —F, —CF$_3$, —C$_2$F$_5$, —C$_3$F$_7$, —C$_4$F$_9$.

Examples of sulfonylamide of formula (V) include bis(fluorosulfonyl)amide, bis(trifluoromethanesulfonyl)amide, bis(pentafluoroethylsulfonyl)amide, bis(heptafluoropropylsulfonyl)amide, bis(nonafluorobutylsulfonyl)amide, N-trifluoroacetyl-fluorosulfonylamide, N-trifluoroacetyl-trifluoromethanesulfonylamide, N-trifluoroacetyl-pentafluoroethylsulfonyl amide, N-trifluoroacetyl-heptafluoropropylsulfonylamide, N-trifluoroacetyl-nonafluorobutylsulfonylamide, N-fluorosulfonyl-trifluoromethanesulfonylamide, N-fluorosulfonyl-pentafluoroethylsulfonyl amide, N-fluorosulfonyl-heptafluoropropylsulfonylamide, N-fluorosulfonyl-nonafluorobutylsulfonylamide, N-trifluoromethanesulfonyl-pentafluoroethylsulfonyl amide, N-trifluoromethanesulfonyl-heptafluoropropylsulfonylamide or N-trifluoromethanesulfonyl-nonafluorobutylsulfonylamide.

In preferred embodiments, the anion is a halide or a sulfonylamide of formula (V). In more preferred embodiments, the anion is chloride, bis(fluorosulfonyl)amide, bis(trifluoromethanesulfonyl)amide, or N-fluorosulfonyl-trifluoromethanesulfonylamide. In even more preferred embodiments, the anion is fluorosulfonyl)amide, bis(trifluoromethanesulfonyl)amide, or N-fluorosulfonyl-trifluoromethanesulfonylamide. In most preferred embodiments, the anion is bis(trifluoromethanesulfonyl)amide. This last anion is also called bis(trifluoromethane)sulfonimide, bis-triflimide, TFSI, or TFSA. It is of formula CF$_2$—SO$_2$—N—SO$_2$—CF$_3$.

Ionic compounds where L is a linear alkylene linker can be represented by the following general formula (VI):

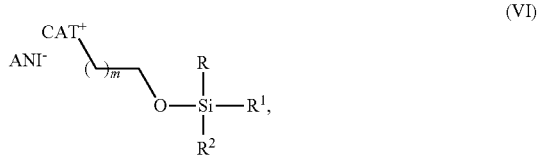 (VI)

wherein CAT$^+$, ANI$^-$, R, R$^1$ and R$^2$ are as defined above and wherein m is an integer varying from 0 to 10, preferably from 1 to 5, and more preferably from 1 to 3.

Uses of the Ionic Compounds

The ionic compounds, and ionic liquids, of the invention can, in embodiments, be used as electrolytes in electrochemical cells like batteries, electrochromic devices and capacitors. Such electrochemical cells comprise an anode, a cathode, and an electrolyte. It is preferable that the ionic compounds be liquid at the temperature of operation of the specific electrochemical appliance they are destined to. It is possible to prepare such electrolytes from pure ionic compounds of the invention or from a mixture of at least two ionic compounds of the invention.

To prepare electrolytes from these ionic compounds, it would be apparent to the skilled person that an appropriate conducting salt should be dissolved in them. For use in lithium and lithium ion batteries, lithium salts can be dissolved in an appropriate concentration, for example between 0.05 and 3 mol/liter. Non-limiting examples of lithium salts include perchlorate, tetrafluoroborate, hexafluorophosphate, bis(fluorosulfonyl)amide, bis(trifluoromethanesulfonyl)amide and their derivatives. When the electrolyte is to be used in a different type of electrochemical device, other salts can be dissolved in the ionic liquid(s), for example sodium and potassium salts.

Various additives can be added to the electrolyte to improve its properties. For example, to diminish viscosity and increase conductivity, one or more organic solvents, especially polar solvents like alkyl carbonates, can be added, for example in a quantity varying from about 1 to about 80% of the total mass of electrolyte.

To improve stability at high and low voltages, unsaturated carbonates, like vinylene carbonate and derivatives of ethane (that is vinyl compounds) can be added, for example at a concentration of from about 0.1 to about 15 percent of weight based on the total weight of the electrolyte.

Methods of Making the Ionic Compounds of the Invention

Ionic compounds with trialkylsiloxy group can be prepared in three steps:
i) preparation of an onium salt with a simple anion (like halogenide or sulphate),
ii) anion metathesis, where the simple anion is exchanged by a more complex anions like triflate, tetrafluoroborate, hexafluorophosphate, bis(fluorosulfonyl)amide, bis(trifluoromethanesulfonyl)amide, or tris(pentafluoroethyl)trifluorophosphate, and iii) introduction of the trialkylsilyl group into the molecule.

In some cases, direct preparation of salts with more complex anions can be realized in one step, without anion metathesis.

The tetraalkylammonium salts can be prepared using various procedures:

Step i)

Quaternisation of N,N-Dialkyl-2-Aminoethanol, or its Longer Chain Analogues

Choline analogues can be prepared by quaternisation of N,N-dialkyl-2-aminoethanol, or its longer chain analogues, like N,N-dialkyl-3-aminopropanol, with appropriate alkylating agents.

Alkyl halogenides can be used as starting materials. The chlorides are not very reactive. Therefore, when they are used high reaction temperatures are needed and may result in the deterioration of the product and contamination with coloured impurities that may be hard to remove. Alkyl iodides are very reactive, but the resulting iodide anion can easily be oxidized to iodine, which causes undesired coloration and contamination of the product. Alkyl bromides represent a good compromise between their reactivity and the stability of the final product. For introduction of methyl or ethyl group into the molecule, dimethyl sulphate and diethyl sulphate are also reagents of choice. For special alkyl groups, alkyl mesylates or tosylates can be used.

N,N-dialkyl-2-aminoethanol, or its longer chain analogues, like N,N-dialkyl-3-aminopropanol, is dissolved in an inert solvent like acetonitrile, toluene, THF, or an ether, and a alkylating agent is added at such rate that a certain reaction temperature is maintained. The quaternization reaction is in many cases very exothermic so great care must be paid during the addition. The reaction temperature should be as low as possible to suppress impurity formation, but if chlorides are used as alkylating agents, the reaction will be slow even in boiling toluene. After the reaction is complete, the resulting salt is isolated. In most cases, this can be done by addition of ethyl acetate to facilitate the precipitation of the solid product and its filtration. If the product is liquid, the solvent is removed by evaporation and the remaining liquid washed with a solvent that dissolves the starting compounds but does not dissolve products. The most appropriate solvents for this type of purification are generally ethers or ethyl acetate. The product can be purified by recrystallization from a suitable solvent like water, acetonitrile, acetone or an alcohol or a mixture thereof.

The scheme for this reaction is:

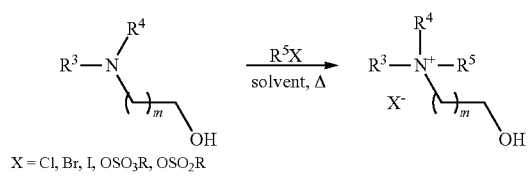

X = Cl, Br, I, OSO₃R, OSO₂R wherein $R_3$, $R_4$, $R_5$ and m are as defined above.

Quaternisation of Trialkylamines with a Derivative of Ethanol or Other Aliphatic Alcohol The quaternisation of trialkylamines can be effected with a derivative of ethanol or other aliphatic alcohol; especially with 2-chloro or 2-bromoethanol and 3-halopropanol. Bromo derivatives are more reactive so lower temperatures are needed and the reaction usually proceeds smoothly without formation of impurities. This method is especially suitable for preparation of cyclic analogues like imidazolium, piperidinium, morpholinium, pyrrolidinium and azepanium salts.

Trialkyl amine and ω-haloalcohol are reacted at elevated temperature, for example at the boiling point of reaction mixture, in suitable solvent like acetonitrile, toluene, THF, or an ether. The scheme of this reaction is as follows:

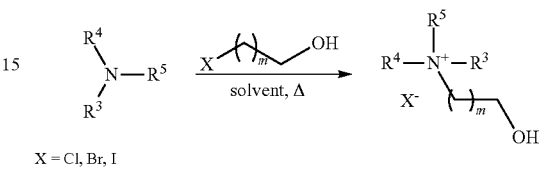

X = Cl, Br, I wherein $R_3$, $R_4$, $R_5$ and m are as defined above.

Reaction Between Trialkylammonium Salts and Ethylene Oxide

A third option is to react a trialkylammonium salt with ethylene oxide in a pressure reactor. The scheme of this reaction is as follows:

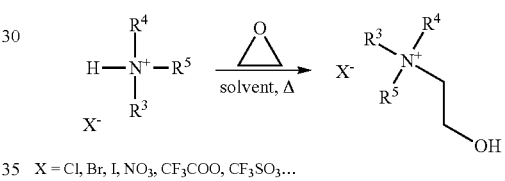

X = Cl, Br, I, NO₃, CF₃COO, CF₃SO₃...

wherein $R_3$, $R_4$, and $R_5$ are as defined above.

In cases where the trialkylammonium salt comprises a complex anion, a desired room temperature IL can be prepared in a single step without anion metathesis.

Step ii) Anion Metathesis

In this step, the anion of an onium salt, produced by quaternisation, is exchanged for a desired usually more complex, more stable and less associative anion. This procedure usually makes the onium salt liquid. Usually, highly fluorinated anions like tetrafluoroborate, hexafluorophosphate, triflate, bis(fluorosulfonyl)amide (FSI), bis(trifluoromethanesulfonyl)amide (TFSA), tris(pentafluoroethyl)trifluorophosphate (FAP) are introduced into the structure of ionic compound or ionic liquid. Sources of these anions can be free acids or their salts, preferably salts of alkali metals.

The onium salt and the source of the desired anion are mixed in an appropriate solvent, which can be for example water or an organic solvent. The driving force of metathesis is a rapid ionic reaction, that is the formation of a poorly dissociated compound (precipitate, gas) or the separation of a reaction mixture in two layers (that is the precipitation of an insoluble liquid).

FSI, TFSI and FAP are very hydrophobic, so anion metathesis can be performed in water where the resulting ionic liquid separates as denser layer. To remove the impurities, a simple wash with water is required. In some cases, anion metathesis can be performed in organic solvents, especially when the desired ionic compound is soluble in water and performing anion exchange in water could result in loss of part of the ionic compound.

Step iii) Introduction of the Silyl Group

The introduction of the silyl group could be considered as similar to the protection of an aliphatic OH group in a cation molecule. Such aliphatic OH is a sensitive part of an ionic compound and is not compatible with use in electrolytes. The result of the protection is a silyloxy group, which can be sensitive to interactions with protic compounds and can be hydrolyzed. The hydrolytic stability of the silyloxy groups is improved by increasing the size or branching of alkyl groups attached to the silicon atom. Various silyl groups can be introduced, but it is of advantage to use the smallest alkyl groups possible, as larger groups can increase the melting point of the ionic compounds and/or the viscosity of the ionic liquids.

Trialkyl silyl groups are introduced into the cation by a silylating agent, which is capable to react with an aliphatic OH group. Not all silylating agents are however equally suitable. Trialkylsilyl halides, triflate, sulfonates generate acid during silylation and their removal from the reaction mixture can be very difficult. With ionic liquids, the most acceptable method for purification is evaporation, so the best silylating agents are those which generate only gaseous by-products. In this context, silazanes are the most suitable reagents for introduction of silyl group because their only by-products are ammonia or amines. Other reagents can however be used.

For example, there are many silylating agents that can be used to introduce a trimethylsilyl (TMS) group. TMS is commonly used as a protecting group in general organic synthesis. Use of hexamethyldisilazane (HMDS) is most advantageous because it is inexpensive. Also N,N-Bis(trimethylsilyl)methylamine, N-trimethylsilyldimethylamine can be used as their by-products are methylamine and dimethyl amine, which are gases at room temperature.

For other silyl groups, silylating agents may not as readily available, but one can prepare silazanes from chlorosilanes, purify them by distillation, and then use them in the preparation of silylated ionic liquids. For example, N-triethylsilyl-dimethylamine and N-triethylsilyl-diethylamine can be used to introduce a triethylsilyl group. Similarly, N-ethyldimethylsilyl-dimethylamine and N-ethyldimethylsilyl-diethylamine can be used to introduce a ethyldimethylsilyl group.

The silylation of hydroxyl-ionic compounds can be accomplished by mixing the silylating agent with the ionic compound in an inert solvent, heating this mixture to elevated temperature and after completion the reaction, removing the by-product. The ionic compound is obtained after vigorous vacuum drying and is generally pure enough for most purposes. Sometimes additional purification, such as decolourizing charcoal and filtration, may be needed.

A solvent is not always needed for the silylation reaction. If the ionic compound is liquid at room temperature, the reaction can be carried out without a solvent, but, in this case, vigorous stirring is generally required as the silazane and the hydroxy ionic compound are generally not miscible. The induction period for this reaction may be a bit longer than otherwise, but when the reaction starts, it generally continues until complete transformation.

If HMDS is used for silylation, dichloromethane can be used as a solvent, because it will generally dissolve both HMDS and the ionic compound.

In most cases, heating at a temperature around 50-60° C. is sufficient to start vigorous reaction. To obtaining a complete transformation, the mixture may need to be heated for several hours. After that, the volatile compounds are removed and the silylated ionic compound is obtained in generally pure form.

Definitions

Herein, the use of the terms "a" and "an" and "the" and similar referents in the context of describing the invention (especially in the context of the following claims) are to be construed to cover both the singular and the plural, unless otherwise indicated herein or clearly contradicted by context.

Also, the terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combinations of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Unless otherwise defined, all technical and scientific terms used herein have the same meaning as commonly understood by one of ordinary skill in the art to which this invention belongs.

In particular, herein, the terms "alkyl", "alkylene", "alkenyl", "alkenylene", "alkynyl", "alkynylene" and their derivatives (such as alkoxy, alkyleneoxy, etc.) have their ordinary meaning in the art. It is to be noted that, unless otherwise specified, the hydrocarbon chains of these groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2 carbon atoms. For more certainty, an alkyl is a monovalent saturated aliphatic hydrocarbon radical of general formula —$C_nH_{2n+1}$. An alkylene is a bivalent saturated aliphatic hydrocarbon radical of general formula —$C_nH_{2n}$— (also called alkanediyl). An alkenyl is a monovalent aliphatic hydrocarbon radical comprising at least one double bond. An alkenylene is a bivalent aliphatic hydrocarbon radical comprising at least one double bond. An alkynyl is a monovalent aliphatic hydrocarbon radical comprising at least one triple bond. An alkynylene is a bivalent aliphatic hydrocarbon radical comprising at least one triple bond. An alkyloxy or alkoxy is a monovalent radical of formula —O-alkyl. An alkyleneoxy is a bivalent radical of formula —O-alkylene-. An example of alkyleneoxy is —O—CH$_2$—CH$_2$—, which is called ethyleneoxy. A linear chain comprising two or more ethyleneoxy groups attached together (i.e. —[—O—CH$_2$—CH$_2$—]$_n$—) can be referred to as a polyethylene glycol (PEG), polyethylene oxide (PEO), or polyoxyethylene (POE) chain. An alkenyloxy is a monovalent radical of formula —O-alkenyl. An alkenyleneoxy is a bivalent radical of formula —O-alkenylene-. An alkynyloxy is a monovalent radical of formula —O-alkynyl-. An alkynyleneoxy is a bivalent radical of formula —O-alkynylene.

Herein, the term "about" has its ordinary meaning. In embodiments, it may mean plus or minus 10% or plus or minus 5% of the numerical value qualified.

Other objects, advantages and features of the present invention will become more apparent upon reading of the following non-restrictive description of specific embodiments thereof, given by way of example only with reference to the accompanying drawings.

Description of Illustrative Embodiment

The present invention is illustrated in further details by the following non-limiting examples.

More specifically, we report below the synthesis and testing of several ionic compound of the invention. These compounds were all liquids at room temperature or were solids with a low melting point.

We also report cyclic voltametry results for several of these compounds. These results show the range of stability of the ionic compounds and thus indicate the range of voltage of the device in which they are to be used. For example, graphite has a working voltage of 0.1 or 0.2 V, lithium has a working voltage 0V, while lithium titanate has a working voltage of 1.5V.

Finally, we also report on the compatibility of some of these ionic compounds with various electrodes.

Example 1—Preparation of N-(2-trimethylsiloxyethyl)-N,N,N-trimethylammonium bis(trifluoromethane sulfonyl)amide (N1112-OTMS-TFSI)

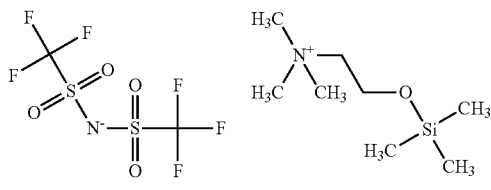

a) Choline bis(trifluoromethanesulfonyl)amide 55.85 g (0.4 mol) of choline chloride (Sigma-Aldrich) were dissolved in 150 ml of MQ water. Under vigorous stirring, the resulting choline chloride solution was mixed with a solution of 120 g (0.41 mol) of lithium bis(trifluoromethanesulfonyl)amide (LiTFSI) in 200 ml of MQ water. Phase separation occurred at once, but the stirring was continued for another 5 hours at room temperature. Then, 100 ml of CH$_2$Cl$_2$ were added and the phases were separated. The water phase was extracted with 50 ml of CH$_2$Cl$_2$ and the combined organic phases were washed 6 times with 50 ml of MQ water. A clear colourless solution was obtained. This was poured into a round bottom flask; the solvent was removed using a rotary evaporator and then under high vacuum at 60° C. In this manner, 127 g (83%) of pure choline bis(trifluoromethanesulfonyl)amide (choline TFSI) were obtained.

$^1$H NMR (300 MHz, DMSO-d$_6$) δ/ppm: 3.11 (s, 9H), 3.31-3.47 (m, 2H), 3.84 (tt, J=5.03, 2.29 Hz, 2H), 5.26 (t, J=4.94 Hz, 1H).

$^{13}$C NMR (75 MHz, DMSO-d$_6$) δ/ppm: 53.30 (br. t, J=3.50, 3.50 Hz), 55.31 (s), 67.18 (br. t, J=3.20, 3.20 Hz), 119.63 (q, J=321.70 Hz).

b) N-(2-trimethylsiloxyethyl)-N,N,N-trimethylammonium bis(trifluoromethanesulfonyl)amide To a 500 ml round bottom flask containing 127 g (0.33 mol) of neat choline TFSI, 53 g (0.33 mol) of hexamethyldisilazane (HMDS) were added at room temperature as a gentle stream of nitrogen was passed through the apparatus to facilitate removal of forming ammonia. The mixture was slowly heated to 60-70° C. and stirred so that a fine emulsion of HMDS in choline TFSI was formed. A vigorous evolution of gaseous ammonia started as the temperature reached 60° C. and ended after a few minutes. The mixture was heated and stirred for additional 4 hours after the end of this vigorous reaction. Then, the remaining HMDS, which was in a separate layer on top of desired product, was evaporated under high vacuum. The round bottom flask was then refilled 6 times with argon and again evacuated. The product was heated to 70° C. during this manipulation. Finally the apparatus was cooled down under vacuum and refilled with argon. In this manner, 150.5 g (100%) of the title compound in the form of a colourless liquid were obtained.

$^1$H NMR (300 MHz, CHLOROFORM-d) δ/ppm: 0.10 (s, 9H), 3.14 (s, 9H), 3.38-3.49 (m, 2H), 3.87-4.03 (m, 2H).

$^{13}$C NMR (75 MHz, CHLOROFORM-d) δ/ppm: −1.28 (s), 54.22 (t, J=3.50 Hz), 56.67 (s), 67.56 (t, J=3.20 Hz), 119.63 (q, J=320.70 Hz).

Example 2—Preparation of N-ethyl-N-(2-trimethylsiloxyethyl)-N,N-dimethylammonium bis(trifluoromethane sulfonyl)amide (N1122-OTMS-TFSI)

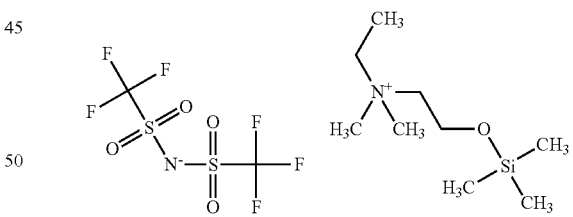

a) N-ethyl-N-2-hydroxyethyl-N,N-dimethylammonium bromide

In a 500 ml round bottom flask equipped with a magnetic stirrer were placed 45.3 g (0.508 mol) of 2-dimethylaminoethanol dissolved in 150 ml of MeCN. To this solution, a mixture of 61.5 g (0.550 mol) ethyl bromide and 60 ml of MeCN was added dropwise over a period of 1.5 h using a water bath (at 20° C.) for cooling during the addition. After half of the EtBr was added, a snow white crystalline product started to precipitate from the solution. The mixture was stirred over a weekend (57 h), and then vacuum filtered, washed with a small amount of acetone, and dried in a vacuum oven at 60° C. The filtrate was evaporated to dryness and additional product was isolated. Altogether, 98.13 g (72%) of N-ethyl-N-2-hydroxyethyl-N,N-dimethylammonium bromide were obtained.

$^1$H NMR (300 MHz, DEUTERIUM OXIDE) δ/ppm: 1.35 (tt, J=7.28, 1.88 Hz, 3H), 3.11 (s, 6H), 3.38-3.52 (m, 4H), 3.95-4.07 (m, 2H).

$^{13}$C NMR (75 MHz, DEUTERIUM OXIDE) δ/ppm: 7.24 (s), 50.38 (t, J=3.90 Hz), 54.92 (s), 60.57 (t, J=2.70 Hz), 63.94 (t, J=3.30 Hz)

b)
N-ethyl-N-2-hydroxyethyl-N,N-dimethylammonium bis(trifluoromethanesulfonyl)amide In a 250 ml round bottom flask, solutions of 52 g (0.263 mol) of N-ethyl-N-2-hydroxyethyl-N,N-dimethylammonium bromide in 70 ml MQ water and 78 g (0.274 mol) of LiTFSI in 80 ml MQ water were mixed together under vigorous stirring. Phase separation occurred at once, but stirring was continued for another 4 hours at room temperature. Then, 100 ml of CH$_2$Cl$_2$ were added and the phases separated. The water phase was extracted with 50 ml of CH$_2$Cl$_2$ and the combined organic phases were washed 6 times with 100 ml of MQ water. A clear colourless solution was obtained and poured into a round bottom flask. The solvent was removed using a rotary evaporator and then under high vacuum at 60° C. In this manner, 70 g (67%) of pure N-ethyl-N-2-hydroxyethyl-N,N-dimethylammonium bis(trifluoromethanesulfonyl)amide as a colourless liquid were obtained.

$^1$H NMR (300 MHz, DMSO-d$_6$) δ/ppm: 1.25 (br. t, J=7.30, 7.30 Hz, 3H), 3.03 (s, 39H), 3.28-3.46 (m, 26H), 3.56 (s, 12H), 3.75-3.91 (m, 13H), 5.29 (t, J=4.94 Hz, 6H).

$^{13}$C NMR (75 MHz, DMSO-d$_6$) δ/ppm: 7.63 (s), 50.23 (t, J=3.50 Hz), 54.96 (s), 59.50-60.18 (m), 64.19 (t, J=2.49 Hz), 119.50 (q, J=321.20 Hz).

c) N-ethyl-N-(2-trimethylsiloxyethyl)-N,N-dimethylammonium bis(trifluoromethanesulfonyl)amide To a 250 ml round bottom flask containing 80 g (0.20 mol) of neat N-ethyl-N-2-hydroxyethyl-N,N-dimethylammonium TFSI, 31 g (0.20 mol) of hexamethyldisilazane (HMDS) were added at room temperature as a gentle stream of nitrogen was passed through the apparatus to facilitate removal of forming ammonia. The mixture was slowly heated to 60-70° C. and stirred so that a fine emulsion of HMDS in IL formed. A vigorous evolution of gaseous ammonia started as the temperature reached 60° C. and ended after a few minutes. The mixture was heated and stirred for an additional 4 hours after the end of the vigorous reaction. Then, the remaining HMDS, which was in a separate layer on top of the desired product, was evaporated under high vacuum. The round bottom flask was then refilled 6 times with argon and again evacuated. The product was heated to 70° C. during this manipulation. Finally, the apparatus was cooled down under vacuum and refilled with argon. In this manner, 94 g (100%) of the title compound in the form of a colourless liquid were obtained.

$^1$H NMR (300 MHz, CHLOROFORM-d) δ/ppm: 0.10 (s, 9H), 1.34 (br. t, J=7.10, 7.10 Hz, 3H), 3.06 (s, 6H), 3.32-3.51 (m, 4H), 3.86-4.04 (m, 2H).

$^{13}$C NMR (75 MHz, CHLOROFORM-d) δ/ppm: −1.25 (s), 7.94 (s), 50.96 (t, J=3.59 Hz), 56.43 (br. s.), 64.54 (br. s.), 119.67 (q, J=321.20 Hz).

$^{19}$F NMR (470 MHz, CHLOROFORM-d) δ/ppm: −78.89 (s).

Example 3—Preparation of N,N-diethyl-N-(2-trimethylsiloxyethyl)-N-methylammonium bis(trifluoromethanesulfonyl)amide (N1222-OTM-TFSI)

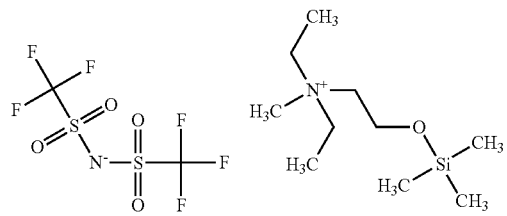

a)
N,N-diethyl-N-2-hydroxyethyl-N-methylammonium methylsulfate

In a 1 L round bottom flask equipped with a magnetic stirrer were placed 117.10 g (1 mol) of 2-diethylaminoethanol dissolved in 250 ml of MeCN. The solution was cooled below 20° C. with the help of an ice water bath. To the cooled solution, a mixture of 130 g (1.03 mol) dimethyl sulfate and 100 ml of MeCN was added dropwise over a period of 0.5 h, not allowing the temperature to rise above 40° C. The mixture was stirred over a weekend (60 h) and MeCN was then removed using a rotary evaporator. 242 g (100%) of N,N-diethyl-N-2-hydroxyethyl-N-methylammonium methylsulfate were obtained in the form of a slightly pink coloured oil.

$^1$H NMR (300 MHz, DMSO-d$_6$) δ/ppm: 1.20 (t, J=7.14 Hz, 6H), 2.96 (s, 3H), 3.28-3.40 (m, 6H), 3.40 (s, 3H), 3.74-3.85 (m, 2H), 5.09 (br. s., 1H).ž

$^{13}$C NMR (75 MHz, DMSO-d$_6$) δ/ppm: 7.64 (s), 47.22 (br. s), 53.16 (s), 54.91 (s), 56.50 (br. s), 61.26 (br. s).

b)
N,N-diethyl-N-2-hydroxyethyl-N-methylammonium bis(trifluoromethanesulfonyl)amide In a 250 ml round bottom flask, solutions of 68.58 g (0.282 mol) of N,N-diethyl-N-2-hydroxyethyl-N-methylammonium methylsulfate dissolved in 70 ml MQ water and 83.23 g (0.290 mol) of LiTFSI dissolved in 80 ml MQ water were mixed under vigorous stirring. Phase separation occurred at once, but the stirring was continued for another 6 hours at room temperature. Then, 100 ml of CH$_2$Cl$_2$ were added and the phases separated. The water phase was extracted with 20 ml of CH$_2$Cl$_2$ and the combined organic phases were washed 6 times with 80 ml of MQ water. To this solution, 5 g of activated charcoal were added. The resulting mixture was heated to its boiling point, allowed to cool down and stirred overnight (16 h). The next morning, the solution was filtered through a PTFE filter of 0.22 μm porosity. A clear solution was obtained and poured into a round bottom flask. The solvent was removed using a rotary evaporator and then under high vacuum at 60° C. In this manner, 65.65 g (56%) of pure N,N-diethyl-N-2-hydroxyethyl-N-methylammonium bis(trifluoromethanesulfonyl) amide as a colourless liquid were obtained.

$^1$H NMR (300 MHz, DMSO-d$_6$) δ/ppm: 1.20 (t, J=7.14 Hz, 6H), 2.96 (s, 3H), 3.28-3.40 (m, 6H), 3.40 (s, 3H), 3.74-3.85 (m, 2H), 5.09 (br. s., 1H).
$^{13}$C NMR (75 MHz, DMSO-d$_6$) δ/ppm: 7.48 (s), 47.28 (br. s.), 54.87 (s), 56.60 (br. s.), 61.48 (br. s.), 119.65 (q, J=321.20 Hz).

c)
N,N-diethyl-N-2-hydroxyethyl-N-methylammonium bis(trifluoromethanesulfonyl)amide To a 250 ml round bottom flask containing 65 g (0.159 mol) of neat N,N-diethyl-N-2-hydroxyethyl-N-methylammonium bis(trifluoromethanesulfonyl)amide, 25.69 g (0.160 mol) of hexamethyldisilazane (HMDS) were added at room temperature as a gentle stream of nitrogen was passed through the apparatus to facilitate removal of forming ammonia. The mixture was slowly heated to 60-70° C. and stirred so that a fine emulsion of HMDS in IL formed. A vigorous evolution of gaseous ammonia started as the temperature reached 60° C. and ended after a few minutes. The mixture was heated and stirred overnight (16 hours after the end of the vigorous reaction). Then, the remaining HMDS, which was in separate layer on top of the desired product, was evaporated under high vacuum. A slightly coloured oil was obtained and diluted with 100 ml of CH$_2$Cl$_2$. 5 g of activated charcoal were added. The mixture was heated to its boiling point, cooled to room temperature and filtered after 1 h through a 0.22 μm PTFE filter. The solvent was removed using a rotary evaporator and then 5 ml of fresh HMDS were added to the clear product. This mixture was vigorously stirred and heated to 70° C. for one hour. Then, the volatile compounds were removed in vacuo and the flask was refilled 6 times with argon and again evacuated. The product was heated to 70° C. during this manipulation. Finally, the apparatus was cooled down under vacuum and refilled with argon. In this manner, 72 g (93%) of the title compound in the form of a colourless liquid were obtained.
$^1$H NMR (300 MHz, CHLOROFORM-d) δ/ppm: 0.07 (s, 9H), 1.27 (t, J=7.14 Hz, 6H), 2.94 (s, 3H), 3.25-3.43 (m, 6H), 3.81-3.98 (m, 2H).
$^{13}$C NMR (75 MHz, CHLOROFORM-d) δ/ppm: −1.37 (s), 7.47 (s), 47.74 (br. s.), 56.10 (s), 57.56 (br. s), 61.60 (br. s.), 119.62 (q, J=321.20 Hz).

Example 4—Preparation of N,N,N-triethyl-N-(2-trimethylsiloxyethyl)ammonium bis(trifluoromethanesulfonyl)amide (N2222-OTM-TFSI)

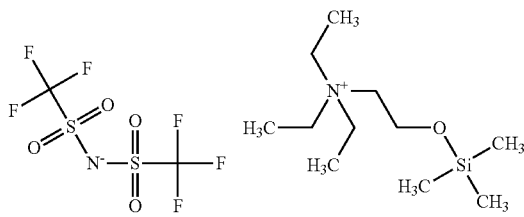

a) N,N,N-triethyl-N-(2-hydroxyethyl)ammonium bromide

In a 500 ml round bottom flask equipped with a magnetic stirrer were placed 58.6 g (0.50 mol) of 2-diethylaminoethanol dissolved in 80 ml of MeCN. To this solution, a mixture of 60 g (0.550 mol) ethyl bromide and 40 ml of MeCN was added dropwise over a period of 0.75 h. The mixture was stirred over a weekend (57 h) during which a white crystalline precipitate separated. This precipitate was vacuum-filtered, washed with a small amount of acetone and dried in a vacuum oven at 60° C. The filtrate was evaporated to small volume and additional product was precipitated using ethyl acetate. Altogether, 87.51 g (77%) of N,N,N-triethyl-N-(2-hydroxyethyl)ammonium bromide were obtained.
$^1$H NMR (300 MHz, DMSO-d$_6$) δ/ppm: 1.17 (t, J=7.14 Hz, 9H), 3.26-3.31 (m, 2H), 3.32 (q, J=7.00 Hz, 6H), 3.76 (br. d, J=4.80 Hz, 2H), 5.26 (t, J=5.49 Hz, 1H)
$^{13}$C NMR (75 MHz, DMSO-d$_6$) δ/ppm: 7.31 (s), 52.72 (br. s), 54.37 (s), 57.67 (br. s).

b) N,N,N-triethyl-N-(2-hydroxyethyl)ammonium bis(trifluoromethanesulfonyl)amide

In a 250 ml round bottom flask, solutions of 40 g (0.177 mol) of N,N,N-triethyl-N-(2-hydroxyethyl)ammonium bromide in 70 ml MQ water and 53 g (0.185 mol) of LiTFSI in 80 ml MQ water were mixed under vigorous stirring. Phase separation occurred at once, but the stirring was continued overnight (16 hours) at room temperature. Then, 100 ml of CH$_2$Cl$_2$ were added and the phases separated. The water phase was extracted with 20 ml of CH$_2$Cl$_2$ and the combined organic phases were washed 6 times with 80 ml of MQ water. A clear solution was obtained and poured into a round bottom flask. The solvent was first removed using a rotary evaporator and then under high vacuum at 60° C. In this manner, 65.71 g (87%) of pure N,N,N-triethyl-N-(2-hydroxyethyl)ammonium bis(trifluoromethanesulfonyl)amide as a colourless liquid were obtained.
$^1$H NMR (300 MHz, DMSO-d$_6$) δ/ppm: 1.19 (t, J=7.14 Hz, 9H), 3.19-3.40 (m, 8H), 3.79 (d, J=4.76 Hz, 2H), 5.25 (t, J=5.13 Hz, 1H).
$^{13}$C NMR (75 MHz, DMSO-d$_6$) δ/ppm: 7.10 (s), 52.95 (br. s.), 54.71 (s), 57.94 (br. s.), 119.69 (q, J=321.20 Hz).

c)
N,N,N-triethyl-N-(2-trimethylsiloxyethyl)ammonium bis(trifluoromethanesulfonyl)amide To a 250 ml round bottom flask containing 65 g (0.152 mol) of neat N,N,N-triethyl-N-(2-trimethylsiloxyethyl)ammonium TFSI, 24.5 g (0.152 mol) of hexamethyldisilazane (HMDS) were added at 60° C. as a gentle stream of nitrogen was passed through the apparatus to facilitate removal of forming ammonia. The reaction started 2 minutes after the addition. The mixture was stirred so that a fine emulsion of HMDS in choline TFSI formed. Intense evolution of gaseous ammonia ended after a few minutes, but the mixture was heated and stirred overnight (16 hours after the end of the intense reaction). Then, the remaining HMDS, which was in separate layer on top of the desired product, was evaporated under high vacuum. The round bottom flask was then refilled 5 times with argon and again evacuated. The product was heated to 70° C. during this manipulation. Finally the apparatus was cooled down under vacuum and refilled with argon. In this manner, 75.6 g (100%) of the title compound in the form of a colourless liquid were obtained.
$^1$H NMR (300 MHz, CHLOROFORM-d) δ/ppm: 0.11 (s, 9H), 1.28 (t, J=7.3 Hz, 9H), 3.17-3.50 (m, 8H), 3.91 (br. s., 2H)
$^{13}$C NMR (75 MHz, CHLOROFORM-d) δ/ppm: −1.20 (s), 7.23 (s), 53.72 (br. s.), 56.02 (s), 58.27 (br. s.), 119.76 (q, J=321.20 Hz).

Example 5—Preparation of N-(2-trimethylsiloxy-
ethyl)-N,N-dimethyl-N-propylammonium bis(trif-
luoromethane sulfonyl)amide (N1132-OTMS-TFSI)

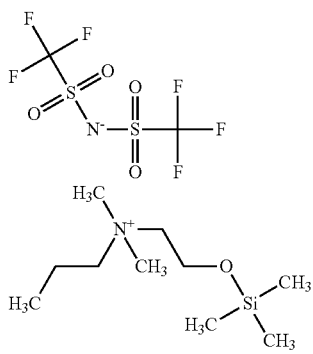

a)
N-(2-hydroxyethyl)-N,N-dimethyl-N-propylammonium
bromide

In a 1000 ml round bottom flask equipped with a magnetic stirrer were placed 135 g (1.50 mol) of 2-dimethylaminoethanol dissolved in 200 ml of MeCN. The solution cooled considerably during mixing. To this solution, a mixture of 200 g (1.64 mol) of propyl bromide, 80 ml of MeCN and 50 ml toluene was added dropwise over a period of 1 h while the temperature was not allowed to exceed 35° C. At first, an addition rate of about 5 ml/min was used, after warming was detected, this rate was reduced to 5 drops/second. The mixture was stirred over a weekend (57 h) during which a small amount of white crystalline precipitate separated. 200 ml of ethyl acetate were added to precipitate the majority of the product, which was then vacuum-filtered, washed with a small amount of ethyl acetate and dried in a vacuum oven at 60° C. The filtrate was evaporated to a small volume and additional product was precipitated with ethyl acetate. Altogether, 307 g (96%) of N-(2-hydroxyethyl)-N,N-dimethyl-N-propylammonium bromide were obtained.

$^1$H NMR (300 MHz, DMSO-$d_6$) δ/ppm: 0.87 (t, J=7.3 Hz, 3H), 1.57-1.78 (m, 2H), 3.08 (s, 6H), 3.26-3.37 (m, 2H), 3.38-3.46 (m, 2H), 3.81 (br. s., 2H), 5.26 (t, J=5.1 Hz, 1H).
$^{13}$C NMR (75 MHz, DMSO-$d_6$) δ/ppm: 10.57 (s), 15.55 (s), 50.88 (t, J=3.5 Hz), 54.88 (s), 64.61 (br. t), 65.38 (br. t).

b) N-(2-hydroxyethyl)-N,N-dimethyl-N-propylammonium bis(trifluoromethanesulfonyl)amide In a 500 ml round bottom flask, solutions of 100 g (0.472 mol) of N-(2-hydroxyethyl)-N,N-dimethyl-N-propylammonium bromide in 100 ml MQ water and 135 g (0.472 mol) of LiTFSI in 100 ml MQ water were mixed under vigorous stirring. Phase separation occurred at once, but the stirring was continued overnight (16 hours) at room temperature. Then, 120 ml of CH$_2$Cl$_2$ were added and the phases separated. The water phase was extracted with 20 ml of CH$_2$Cl$_2$ and the combined organic phases were washed 7 times with 80 ml of MQ water. A clear solution was obtained and poured into a round bottom flask. The solvent was removed first using at rotary evaporator and then under high vacuum at 60° C. In this manner, 154.67 g (80%) of pure N-(2-hydroxyethyl)-N,N-dimethyl-N-propylammonium bis(trifluoromethanesulfonyl)amide as a colourless liquid were obtained.

$^1$H NMR (300 MHz, DMSO-$d_6$) δ/ppm: 0.89 (t, J=7.3 Hz, 3H), 1.59-1.80 (m, 2H), 3.05 (s, 6H), 3.21-3.32 (m, 2H), 3.33-3.40 (m, 2H), 3.83 (br. s., 13H), 5.26 (t, J=4.9 Hz, 6H).
$^{13}$C NMR (75 MHz, DMSO-$d_6$) δ/ppm: 10.38 (s), 15.51 (s), 50.87 (br. t), 55.02 (s), 64.82 (br. t), 65.65 (br. t), 119.58 (q, J=321.8 Hz).
$^{19}$F NMR (470 MHz, DMSO-$d_6$) δ/ppm: −78.76 (s).

c) N-(2-trimethylsiloxyethyl)-N,N-dimethyl-N-propylammonium bis(trifluoromethanesulfonyl)amide To a 250 ml round bottom flask containing 154.6 g (0.38 mol) of neat N-(2-hydroxyethyl)-N,N-dimethyl-N-propylammonium bis(trifluoromethanesulfonyl)amide, 72.63 g (0.45 mol) of hexamethyldisilazane (HMDS) were added at room temperature as a gentle stream of nitrogen was passed through the apparatus to facilitate the removal of forming ammonia. The mixture was slowly heated to 60-70° C. and stirred so that a fine emulsion of HMDS in IL formed. A vigorous evolution of gaseous ammonia started as the temperature reached 60° C. and ended after a few minutes, but the mixture was heated and stirred overnight (16 hours after the end of vigorous reaction). Then, the remaining HMDS, which was in separate layer on top of the desired product, was decanted. A slightly coloured oil was obtained and diluted with 150 ml of CH$_2$—Cl$_2$. 10 g of activated charcoal were added and the mixture was heated to its boiling point for 3 minutes. The mixture was then cooled to room temperature and filtered after 1 h through a 0.22 μm PTFE filter. The solvent was removed using a rotary evaporator. 5 ml of fresh HMDS were added to the clear product. The resulting mixture was vigorously stirred and heated to 70° C. for one hour. Then, the volatile compounds were removed in vacuo and the flask was refilled 6 times with argon and again evacuated. The product was heated to 70° C. during this manipulation. Finally, the apparatus was cooled down under vacuum and refilled with argon. In this manner, 183 g (99%) of the title compound in the form of a colourless liquid were obtained.

$^1$H NMR (300 MHz, CHLOROFORM-d) δ/ppm: 0.10 (s, 9H), 0.95 (t, J=7.1 Hz, 3H), 1.65-1.83 (m, 2H), 3.08 (s, 6H), 3.21-3.31 (m, 2H), 3.40 (dt, J=4.5, 2.3 Hz, 2H), 3.94 (br. s., 2H).
$^{13}$C NMR (75 MHz, CHLOROFORM-d) δ/ppm: −4.96-1.24 (m), 9.90 (br. s.), 15.95 (br. s.), 51.56 (br. s.), 56.49 (s), 64.90 (br. s.), 67.02 (br. s), 119.68 (q, J=321.2 Hz).
$^{19}$F NMR (470 MHz, CHLOROFORM-d) δ/ppm: −78.87 (s).

Example 6—Preparation of
N-(2-trimethylsiloxyethyl)-N-methylpyrrolidinium
bis(trifluoromethanesulfonyl)amide

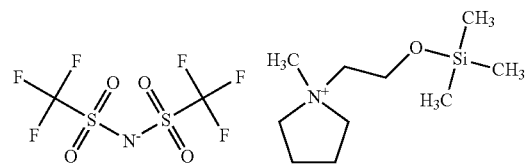

a) N-(2-hydroxyethyl)-N-methylpyrrolidinium
chloride

In a 250 ml round bottom flask equipped with a magnetic stirrer were placed 30 g (0.352 mol) of N-methylpyrrolidine dissolved in 83 g of toluene. To this solution, a mixture of 28.3 g (0.352 mol) of 2-chloroethanol in 20 g of toluene was added dropwise over period of 0.5 h. The mixture was stirred over a weekend (57 h) during which no signs of completed reaction were observed. The mixture was thus heated to 80° C. for 14 h during which phase separation occurred. The mixture was cooled to room temperature and the bottom layer solidified. Toluene was decanted and the solid was then crushed and dissolved in methanol. 5 g of activated charcoal were added. The mixture was heated to its boiling point, cooled and filtered. The filtrate was evaporated to obtain 43.34 g (75%) of the title N-(2-hydroxyethyl)-N-methylpyrrolidinium chloride.

$^1$H NMR (300 MHz, DMSO-d$_6$) δ/ppm: 1.93-2.17 (m, 4H), 3.08 (s, 3H), 3.47 (dd, J=6.04, 4.21 Hz, 2H), 3.52-3.62 (m, 4H), 3.80 (dd, J=4.39, 2.20 Hz, 2H), 5.72 (t, J=5.31 Hz, 1H).

$^{13}$C NMR (75 MHz, DMSO-d$_6$) δ/ppm: 25.64 (s), 52.57 (br. s.), 60.17 (s), 68.93 (br. s.), 69.31 (br. s.).

b) N-(2-hydroxyethyl)-N-methylpyrrolidinium bis(trifluoromethanesulfonyl)amide

In a 250 ml round bottom flask, solutions of 38 g (0.23 mol) of N-(2-hydroxyethyl)-N-methylpyrrolidinium chloride in 130 ml MQ water and 65 g (0.23 mol) of solid LiTFSI were mixed under vigorous stirring. Phase separation occurred at once, but the stirring was continued overnight (16 hours) at room temperature. Then, 80 ml of CH$_2$Cl$_2$ were added and the phases separated. The organic phase was washed 7 times with 80 ml of MQ water. A clear solution was obtained and poured into a round bottom flask. The solvent was removed first using a rotary evaporator and then under high vacuum at 65° C. In this manner, 67.46 g (70%) of pure N-(2-hydroxyethyl)-N,N-dimethyl-N-propylammonium bis(trifluoromethanesulfonyl)amide as a colourless liquid were obtained.

$^1$H NMR (300 MHz, DMSO-d$_6$) δ/ppm: 1.96-2.21 (m, 4H), 3.03 (s, 3H), 3.42 (dd, J=5.86, 4.39 Hz, 2H), 3.46-3.59 (m, 4H), 3.76-3.92 (m, 2H), 5.27 (t, J=4.76 Hz, 1H).

$^{13}$C NMR (75 MHz, DMSO-d$_6$) δ/ppm: 20.89 (s), 47.98 (t, J=3.50 Hz), 55.59 (s), 64.31 (t, J=2.80 Hz), 64.66 (t, J=2.80 Hz), 119.54 (q, J=322.00 Hz).

c) N-(2-trimethylsiloxyethyl)-N-methylpyrrolidinium bis(trifluoromethanesulfonyl)amide To a 250 ml round bottom flask containing 67.46 g (0.164 mol) of neat N-(2-hydroxyethyl)-N-methylpyrrolidinium bis(trifluoromethanesulfonyl)amide, 27 g (0.168 mol) of hexamethyldisilazane (HMDS) were added at room temperature as a gentle stream of nitrogen was passed through the apparatus to facilitate removal of forming ammonia. The mixture was slowly heated to 60-70° C. and stirred so that a fine emulsion of HMDS in IL formed. A vigorous evolution of gaseous ammonia started close to 60° C. and ended after a few minutes. The mixture was heated and stirred overnight (16 hours after the end of vigorous reaction). Then, the volatile compounds were removed in vacuo and the flask was refilled 6 times with Ar and again evacuated. The product was heated to 70° C. during this manipulation. Finally, the apparatus was cooled down under vacuum and refilled with argon. In this manner, 81 g (100%) of the title compound in form of a colourless liquid, which solidified at room temperature, were obtained. The melting point of this solid was around 40° C.

$^1$H NMR (300 MHz, CHLOROFORM-d) δ/ppm: 0.07 (s, 9H), 2.01-2.26 (m, 4H), 3.02 (s, 3H), 3.32-3.43 (m, 2H), 3.44-3.62 (m, 4H), 3.84-4.00 (m, 2H).

$^{13}$C NMR (75 MHz, CHLOROFORM-d) δ/ppm: -1.35 (s), 20.96 (s), 48.29 (br. s.), 56.65 (s), 65.11 (br. s.), 65.35 (br. s), 119.57 (q, J=323.70 Hz).

$^{19}$F NMR (470 MHz, CHLOROFORM-d) δ/ppm: -79.21 (s)

Example 7—Preparation of 1-(2-trimethylsiloxyethyl)-2,3-dimethylimidazolium bis(trifluoromethanesulfonyl)amide

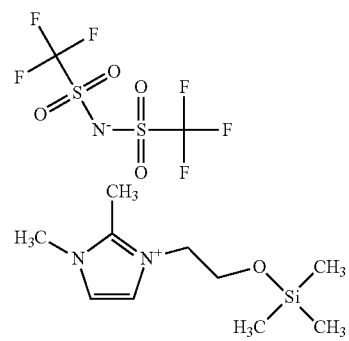

a) 1-(2-hydroxyethyl)-2,3-dimethylimidazolium chloride

In a 250 ml round bottom flask equipped with a magnetic stirrer were placed 48.07 g (0.5 mol) of 1,2-dimethylimidazole dissolved in 80 ml of toluene. To this solution, 40.26 g (0.5 mol) of 2-chloroethanol were added in one portion. The mixture was stirred over a weekend (57 h) at 70° C. during which no sign of completed reaction were observed. The mixture was heated to reflux for 24 h during which phase separation occurred. The mixture was cooled to room temperature and the lower yellow oily layer solidified. The toluene was decanted and the solid was then crushed, washed with fresh toluene and filtered. Product was dried to obtain 87.25 g (98%) of the title 1-(2-hydroxyethyl)-2,3-dimethylimidazolium chloride.

$^1$H NMR (300 MHz, DMSO-d$_6$) δ/ppm: 2.63 (s, 3H), 3.64 (q, J=5.13 Hz, 2H), 3.79 (s, 3H), 4.23 (t, J=4.94 Hz, 2H), 5.59 (t, J=5.68 Hz, 1H), 7.69-7.79 (m, 2H).

$^{13}$C NMR (75 MHz, DMSO-d$_6$) δ/ppm: 9.78 (s), 34.72 (s), 50.22 (s), 59.60 (s), 121.23 (s), 122.13 (s), 144.86 (s).

b) 1-(2-hydroxyethyl)-2,3-dimethylimidazolium bis(trifluoromethanesulfonyl)amide In a 250 ml round bottom flask, a solution of 20 g (0.113 mol) of N-(2-hydroxyethyl)-N-methylpyrrolidinium chloride in 130 ml MQ water and 36 g (0.125 mol) of solid LiTFSI were mixed under vigorous stirring. Phase separation occurred at once, but the stirring was continued overnight (16 hours) at room temperature. Then, 80 ml of CH$_2$Cl$_2$ were added and the phases separated. The organic phase was washed 4 times with 50 ml of MQ water. A clear solution was obtained and poured into a round bottom flask. The solvent was removed first using a rotary evaporator and then under high vacuum at 65° C. In this manner, 23.2 g (49%) of 1-(2-hydroxyethyl)-2,3-dimethylimidazolium bis(trifluoromethanesulfonyl)amide as a colourless liquid were obtained.

$^1$H NMR (300 MHz, DMSO-$d_6$) δ/ppm: 2.59 (s, 3H), 3.64-3.74 (m, 2H), 3.76 (s, 3H), 4.18 (t, J=4.70 Hz, 2H), 5.11 (br. s, 1H), 7.59 (s, 2H).

$^{13}$C NMR (75 MHz, DMSO-$d_6$) δ/ppm: 9.48 (s), 34.71 (s), 50.38 (s), 59.76 (s), 119.63 (q, J=321.70 Hz), 121.36 (s), 122.26 (s), 144.95 (s).

c)
1-(2-trimethylsiloxyethyl)-2,3-dimethylimidazolium bis(trifluoromethanesulfonyl)amide To a 50 ml round bottom flask, 8.42 g (0.02 mol) of neat 1-(2-hydroxyethyl)-2,3-dimethylimidazolium bis(trifluoromethanesulfonyl)amide and 3.42 g (0.02 mol) of hexamethyldisilazane (HMDS) were added at room temperature, as gentle stream of nitrogen was passed through the apparatus to facilitate the removal of forming ammonia. The mixture was slowly heated to 60-70° C. and stirred so that a fine emulsion of HMDS in IL formed. A vigorous evolution of gaseous ammonia started as the temperature reached to 80° C. and ended after a few minutes. The mixture was stirred for 4 hours at 80° C. and overnight at room temperature (16 hours after the end of the vigorous reaction). Then, the volatile compounds were removed in vacuo. The flask was refilled 6 times with argon and again evacuated. The product was heated to 70° C. during this manipulation. Finally, the apparatus was cooled down under vacuum and refilled with argon. In this manner, 9.8 g (100%) of the title compound in form of a colourless liquid were obtained.

$^1$H NMR (300 MHz, CHLOROFORM-d) δ/ppm: 0.00 (s, 9H), 2.55 (s, 3H), 3.75 (s, 3H), 3.82 (t, J=4.70 Hz, 2H), 4.15 (t, J=4.70 Hz, 3H), 7.18 (m, J=2.20 Hz, 1H), 7.24 (m, J=1.80 Hz, 1H)

$^{13}$C NMR (75 MHz, CHLOROFORM-d) δ/ppm: −2.61-0.00 (m), 9.56 (s), 35.01 (s), 50.67 (s), 60.70 (s), 119.58 (q, J=321.70 Hz), 121.22 (s), 122.13 (s), 144.50 (s).

$^{19}$F NMR (470 MHz, CHLOROFORM-d) δ/ppm: −79.19 (s)

Example 8—Preparation of 1-(2-trimethylsiloxyethyl)-3-methylimidazolium chloride

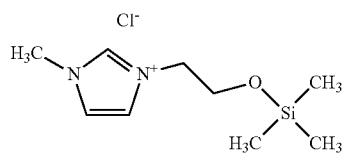

a) 1-(2-hydroxyethyl)-3-methylimidazolium chloride

In a 250 ml round bottom flask equipped with a magnetic stirrer were placed 30.3 g (0.37 mol) of 1-methylimidazole dissolved in 50 ml of MeCN. To this solution, 35 g (0.435 mol) of 2-chloroethanol were added in one portion. The mixture was stirred refluxed for 48 hours during which no sign of completed phase separation occurred. The mixture was cooled to room temperature and a small part of it (5 ml) was mixed with 30 ml ethyl acetate. A yellow oil separated, was washed with fresh ethyl acetate and dried under vacuum. Upon standing, it solidified into a crystalline solid, which was identified as 1-(2-hydroxyethyl)-3-methylimidazolium chloride.

$^1$H NMR (300 MHz, DMSO-$d_6$) δ/ppm: 3.68 (t, J=4.94 Hz, 2H), 3.87 (s, 3H), 4.25 (t, J=4.94 Hz, 2H), 5.60 (br. s., 1H), 7.79-7.84 (m, 1H), 7.85 (t, J=1.65 Hz, 1H), 9.41 (s, 1H).

$^{13}$C NMR (75 MHz, DMSO-$d_6$) δ/ppm: 35.71 (s), 51.49 (s), 59.29 (s), 122.66 (s), 123.26 (s), 136.90 (s).

b) 1-(2-trimethylsiloxyethyl)-3-methylimidazolium chloride

The remaining of the reaction mixture of the above step a) was mixed with 53 ml of HMDS at room temperature and brought to reflux under a $N_2$ purge. At the beginning, two layers formed, but after about 30 minutes, they became miscible and blended together. After 24 hours, the volatile compounds were removed using a rotary evaporator and a high vacuum. 80 g (98%) of a very viscous yellow oil were obtained.

$^1$H NMR (300 MHz, CHLOROFORM-d) δ/ppm: −0.15 (s, 9H), 3.68-3.79 (m, 2H), 3.91 (s, 3H), 4.23-4.38 (m, 2H), 7.37 (t, J=1.65 Hz, 1H), 7.60 (t, J=1.65 Hz, 1H), 10.13 (s, 1H)

$^{13}$C NMR (75 MHz, CHLOROFORM-d) δ/ppm: −1.19 (s), 36.07 (s), 51.49 (s), 60.74 (s), 122.59 (s), 122.89 (s), 137.11 (s).

Example 9—Cyclic Voltametry (CV) of N-(2-trimethylsiloxyethyl)-N,N,N-trimethylammonium bis(trifluoromethanesulfonyl)amide (N1112-OTMS-TFSI)

The compound prepared in Example 1 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 1).

Example 10—CV of N-ethyl-N-(2-trimethylsiloxyethyl)-N,N-dimethylammonium bis(trifluoromethanesulfonyl)amide (N1122-OTMS-TFSI)

Figure 2:
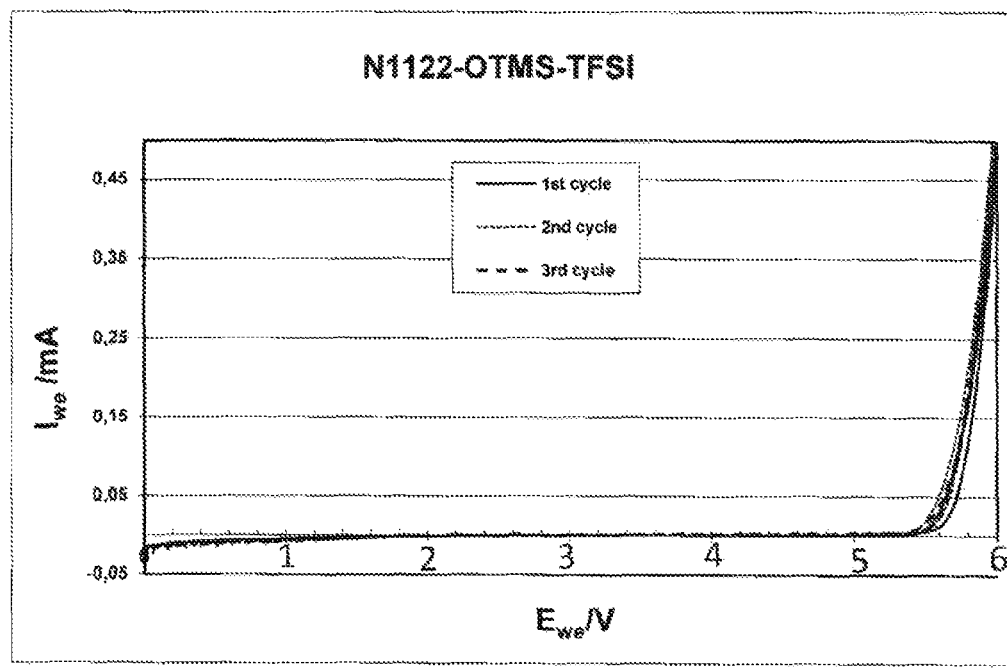
FIG. 2 shows the cyclic voltametry of N1122-OTMS-TFSI.

The compound prepared in Example 2 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 2).

Example 11—CV of 0.3 M LiTFSI in N-ethyl-N-(2-trimethylsiloxyethyl)-N,N-dimethylammonium bis(trifluoromethanesulfonyl)amide (N1122-OTMS-TFSI)

Figure 3:
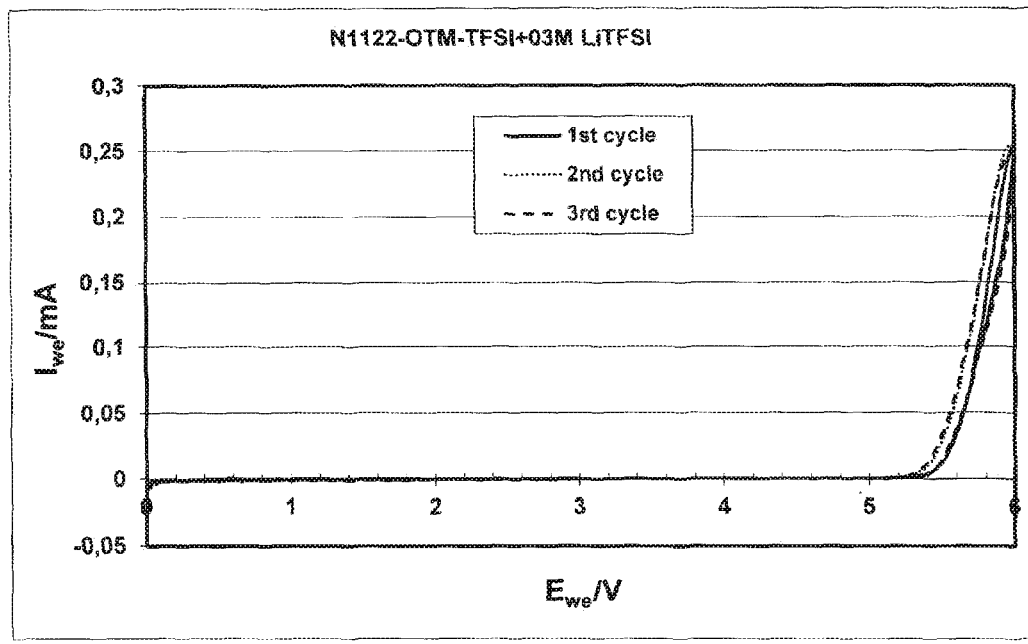
FIG. 3 shows the cyclic voltametry of N1122-OTMS-TFSI+LiTFSI.

A 0.3 molar solution of LiTFSI was prepared by mixing 1.7225 g LiTFSI in 20 ml of IL of Example 2. This solution was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 3).

Example 12—Compatibility of Electrolyte with LiFePO$_4$ Electrode

Figure 4:
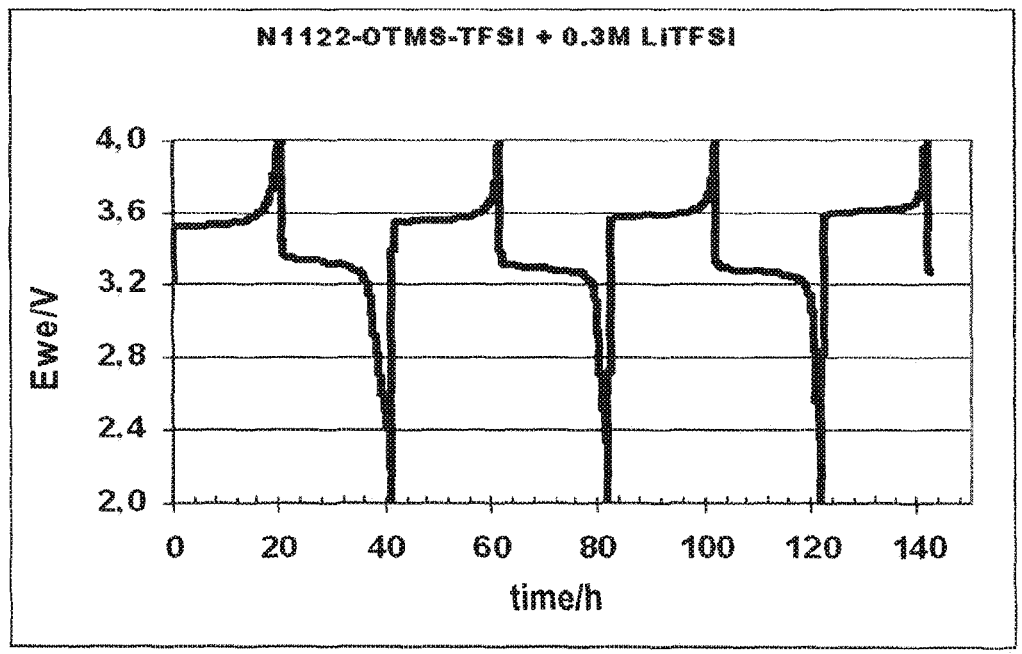
FIG. 4 shows the charge-discharge curves of $LiFePO_4$ vs Li metal in a N1122-OTMS-TFSI based electrolyte.

The electrolyte prepared in Example 11 was tested in a three-electrode electrochemical cell with a LiFePO$_4$ (LFP) electrode. The cathode material was prepared using a mixture of LiFePO$_4$, carbon black and polyvinylidene fluoride (PVDF) in a ratio 84:3:3:10% by weight in N-methylpyrrolidone (NMP). This mixture was then coated on an aluminum current collector. The electrode material was dried at 120° C. in a vacuum oven for 12 h before use. Two pieces of Li metal sheets were used as reference electrode and counter-electrode. The working electrode based on LiFePO$_4$ was cycled between 2-4 V versus Li, at a current rate C/24 (FIG. 4). The reversible capacity was found at 142 mAh/g in the third cycle of the formation.

Example 13—Compatibility of Electrolyte with LiNi$_{1/2}$Mn$_{3/2}$O$_4$ Electrode The electrolyte prepared in Example 11 was tested in a three-electrode electrochemical cell with a LiNi$_{1/2}$Mn$_{3/2}$O$_4$ electrode. The cathode material was prepared using a mixture of LiNi$_{1/2}$Mn$_{3/2}$O$_4$, carbon black and polyvinylidene fluoride (PVDF) in a ratio 84:3:3:10% by weight in NMP. The mixture was then coated on an aluminum current collector. The electrode material was dried at 120° C. in a vacuum oven for 12 h before use. Two pieces of Li metal sheets were used as reference electrode and counter-electrode. LiNi$_{1/2}$Mn$_{3/2}$O$_4$, as the working electrode, was cycled between 3-4.9 V versus Li, at a current rate C/24. Only half of the theoretical capacity with very high hysteresis of charge/discharge was observed. The plateau potential could not be observed.

Example 14—Compatibility of Electrolyte with Graphite Electrode

Figure 5:
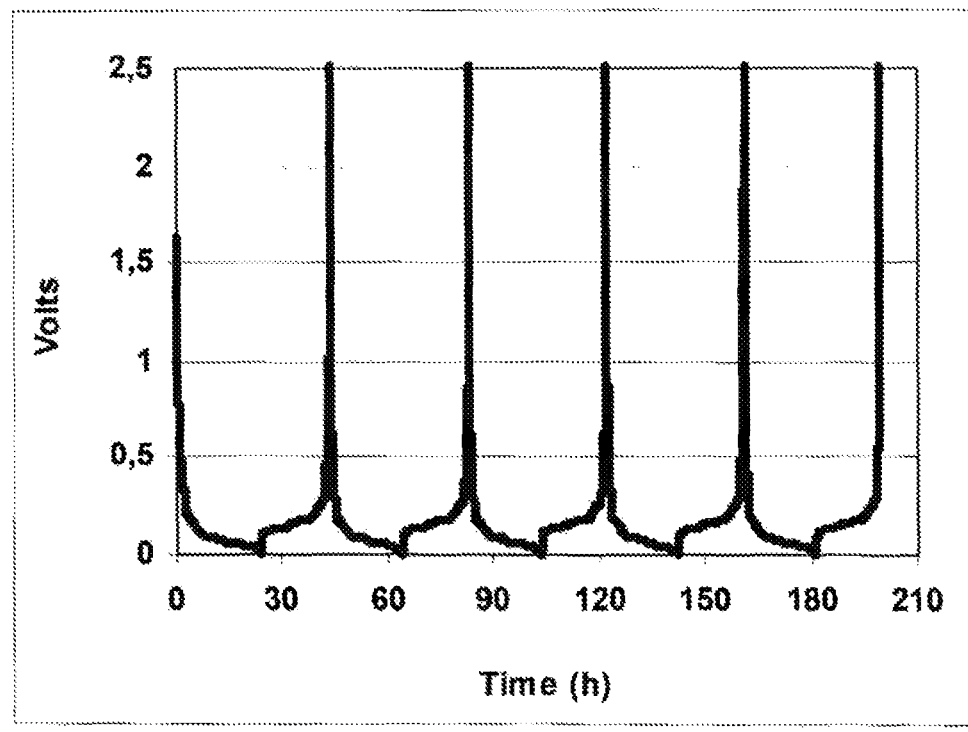
FIG. 5 shows the charge-discharge curves graphite vs Li metal in a N1122-OTMS-TFSI based electrolyte.

The electrolyte prepared in Example 11 was tested in a three-electrode electrochemical cell with graphite (OMAC, Osaka Japan) electrode. The negative electrode was prepared by mixing the graphite, carbon black and PVDF in a ratio 92:2:6% by weight in NMP and then coating the mixture on a copper current collector. The electrode material was dried at 120° C. in a vacuum oven for 12 h before use. Two pieces of Li metal sheets were used as reference electrode and counter-electrode versus Li. The graphite working electrode was cycled between 0-2 V vs. Li at a current rate C/24 (FIG. 5). A coulombic efficiency in the first cycle of 83% and a reversible capacity of 290 mAh/g were observed.

Example 15—CV of N-(2-trimethylsiloxyethyl)-N,N-dimethyl-N-propylammonium bis(trifluoromethanesulfonyl)amide (N1132-OTMS-TFSI)

Figure 6:
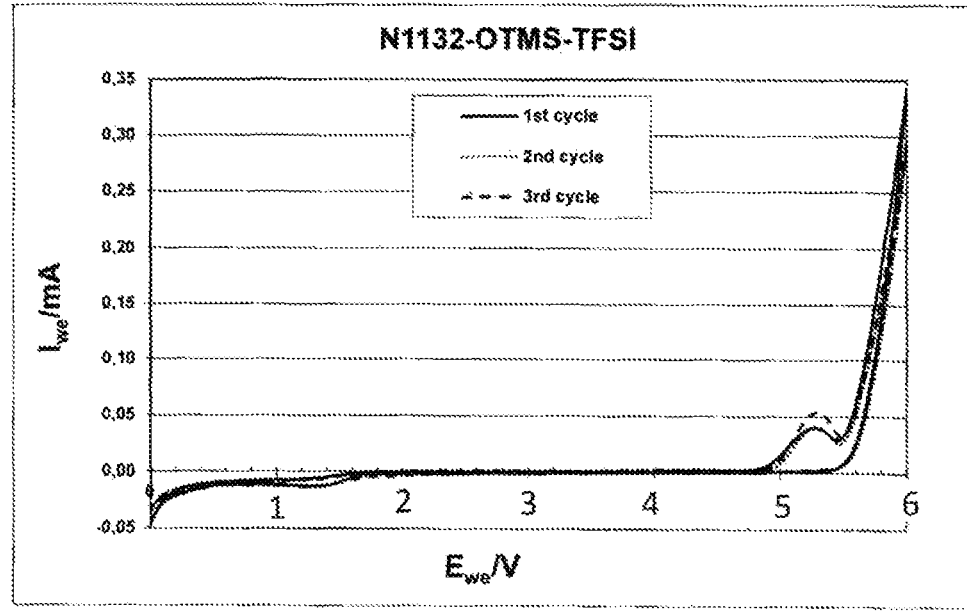
FIG. 6 shows the cyclic voltametry of N1132-OTMS-TFSI.

The compound prepared in Example 5 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 6).

Example 16—CV of 0.3 M LiTFSI in N-(2-trimethylsiloxyethyl)-N,N-dimethyl-N-propylammonium bis(trifluoromethanesulfonyl)amide (N1132-OTMS-TFSI)

Figure 7:
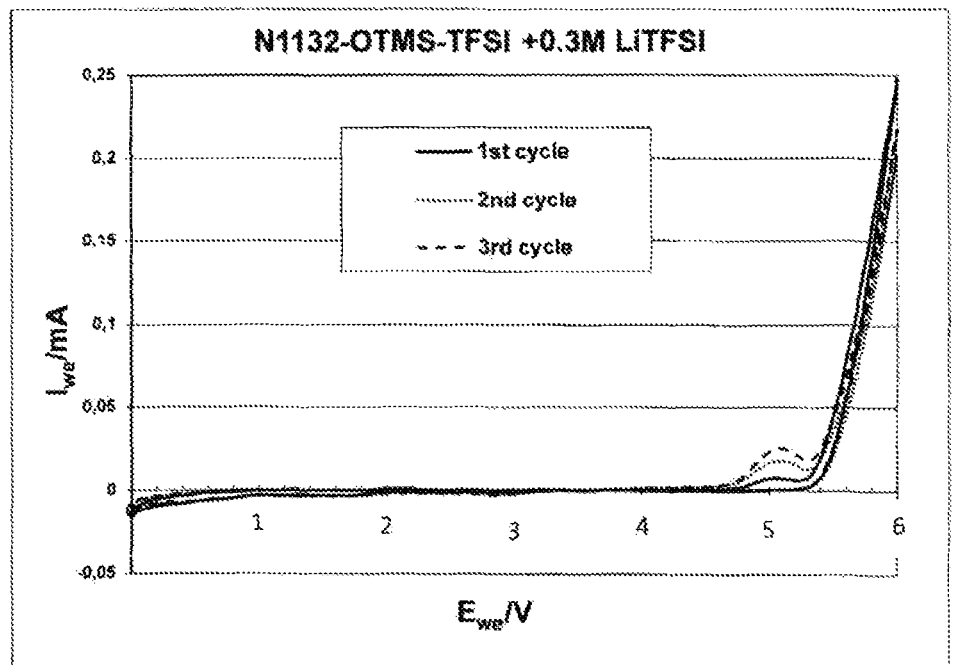
FIG. 7 shows the cyclic voltametry of N1132-OTMS-TFSI+LiTFSI.

A 0.3 molar solution of LiTFSI in the IL of Example 5 was prepared by mixing 1.7225 g LiTFSI in 20 ml of the IL. This electrolyte was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 7).

Example 17—Compatibility of Electrolyte with Active LiFePO$_4$ Electrode

Figure 8:
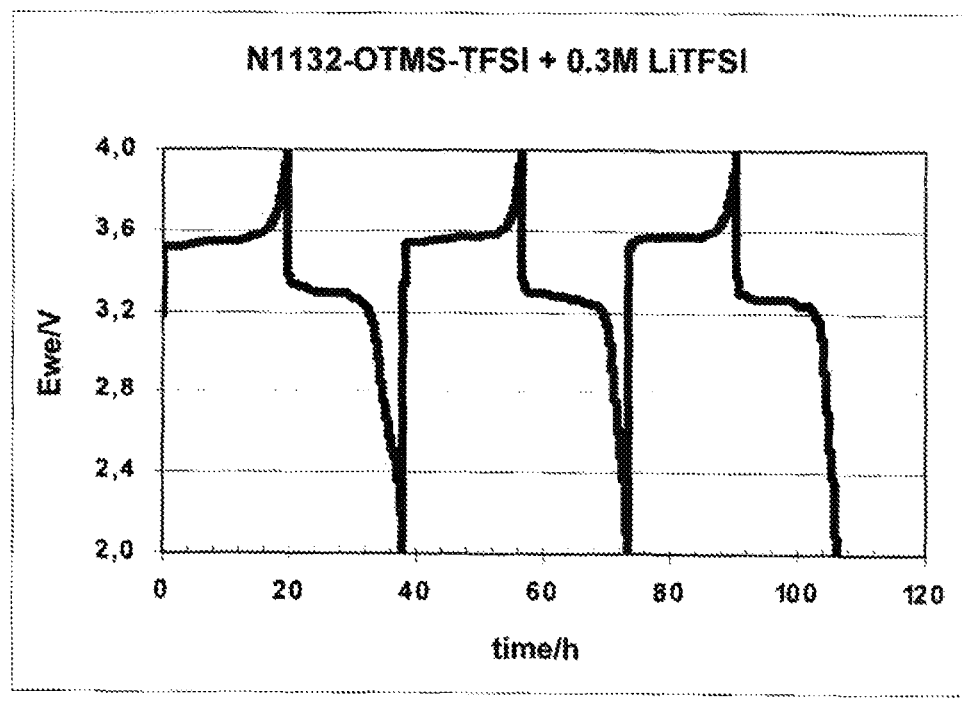
FIG. 8 shows the charge-discharge curves of $LiFePO_4$ vs Li metal in a N1132-OTMS-TFSI based electrolyte.

The electrolyte prepared in Example 16 was tested in a three-electrode electrochemical cell with a LiFePO$_4$, electrode. The cathode material was prepared as described in Example 12. Two pieces of Li metal sheets were used as reference electrode and counter electrode. The LiFePO$_4$ as working electrode was cycled between 2-4 V versus Li, graphite between 2 and 4V vs. Li at a current rate C/24 (FIG. 8). A reversible capacity of 113 mAh/g was observed.

Example 18—Compatibility of Electrolyte with Active LiNi$_{1/2}$Mn$_{3/4}$O$_4$ electrode The electrolyte prepared in Example 16 was tested in a three-electrode electrochemical cell with a LiNi$_{1/2}$Mn$_{3/2}$O$_4$ electrode. The cathode material was prepared as described in the Example 13. Two pieces of Li metal sheets were used as reference electrode and counter electrode. The working electrode, LiNi$_{1/2}$Mn$_{3/2}$O$_4$, was cycled between 3-4.9 V versus Li at current rate C/24. A capacity of 70 mAh/g was obtained with a high voltage cathode.

Example 19—Compatibility of Electrolyte with Active Graphite Electrode

The electrolyte prepared in Example 16 was tested in a three-electrode electrochemical cell with a graphite electrode. The anode material was prepared as described in Example 14. Two pieces of Li metal sheets were used as reference electrode and counter electrode and graphite was used as a working electrode. The cell was cycled between 0-2.5V versus Li at current rate C/24. A reversible capacity of 30 mAh/g was obtained.

Example 20—CV of N,N,N-triethyl-N-(2-trimethylsiloxyethyl)ammonium bis(trifluoromethanesulfonyl)amide (N2222-OTM-TFSI)

Figure 9:
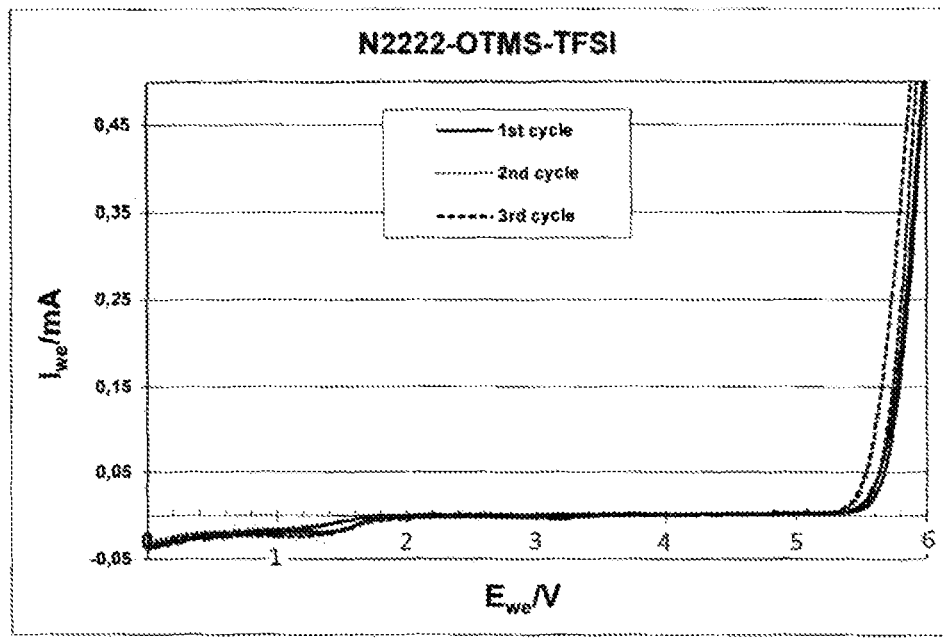
FIG. 9 shows the cyclic voltametry of N2222-OTMS-TFSI.

The compound prepared in Example 4 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at rate of 1 mV/s (FIG. 9).

Figure 10:
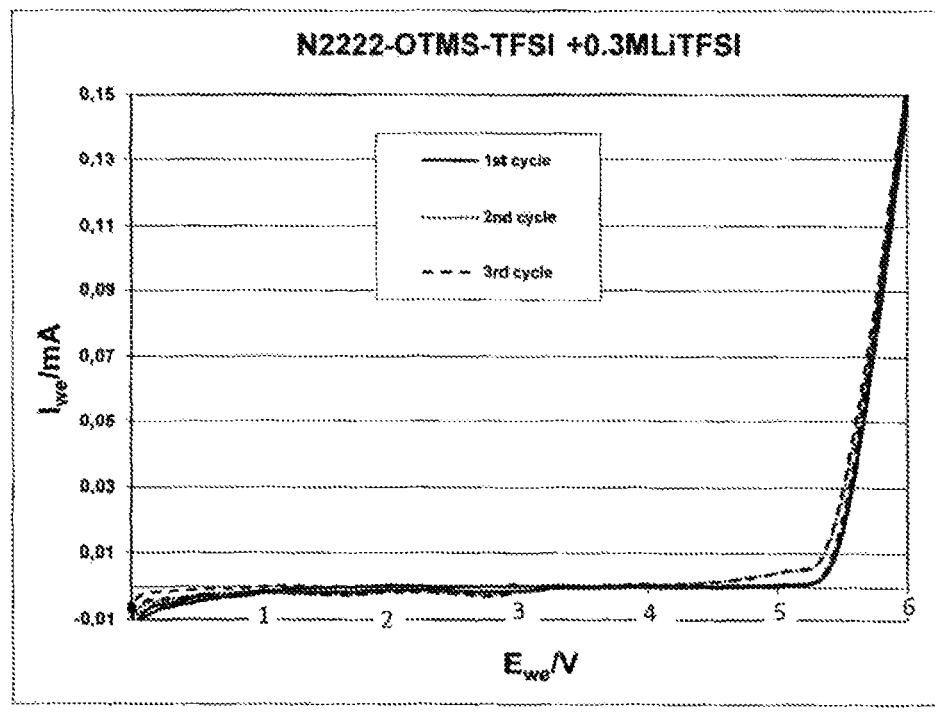
FIG. 10 shows the cyclic voltametry of N2222-OTMS-TFSI+LiTFSI.

Example 21—CV of 0.3 M LiTFSI in N,N,N-triethyl-N-(2-trimethylsiloxyethyl)ammonium bis(trifluoromethanesulfonyl)amide A 0.3 molar solution of LiTFSI in the IL prepared in Example 4 was prepared by mixing 1.7225 g LiTFSI in 20 ml of the IL. This solution was charged into an electrochemical cell. This was a three electrodes cell having a Pt wire as a working electrode, a sheet of lithium metal as a counter electrode and another sheet of lithium metal as a reference electrode. The CV curve was measured between 0-6 V vs. Li at rate of 1 mV/s (FIG. 10).

Example 22—Compatibility of Electrolyte with Active Electrodes

The electrolyte prepared in Example 21 was tested in a three-electrode electrochemical cell. The anode material was prepared as described in Example 14. Two pieces of Li metal sheets were used as reference and electrode and graphite was used as the working electrode. The cell was cycled between 0-2.5V versus Li at current rate C/24. 160 mAh/g of reversible capacity was obtained in the $3^{rd}$ cycle.

Example 23—CV of N,N-diethyl-N-(2-trimethylsiloxyethyl)-N-methylammonium bis(trifluoromethanesulfonyl)amide (N1222-OTMS-TFSI)

Figure 11:
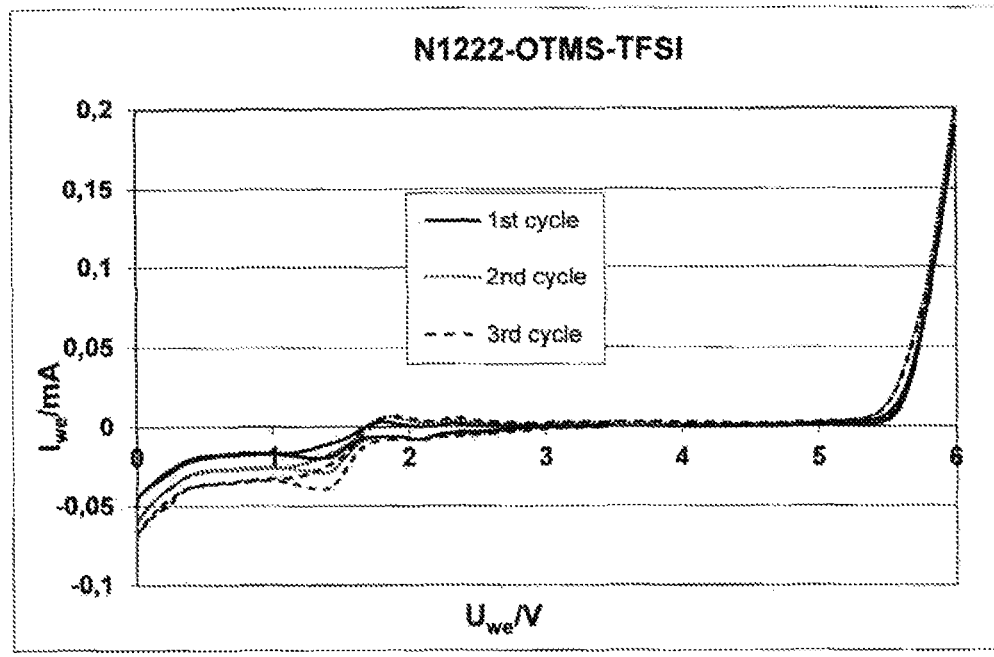
FIG. 11 shows the cyclic voltametry of N1222-OTMS-TFSI.

The compound prepared in Example 3 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at rate of 1 mV/s (FIG. 11).

Example 24—CV of 0.3 M LiTFSI in N,N-diethyl-N-(2-trimethylsiloxyethyl)-N-methylammonium bis(trifluoromethanesulfonyl)amide (N1222-OTM-TFSI+ 0.3M LiTFSI)

Figure 12:
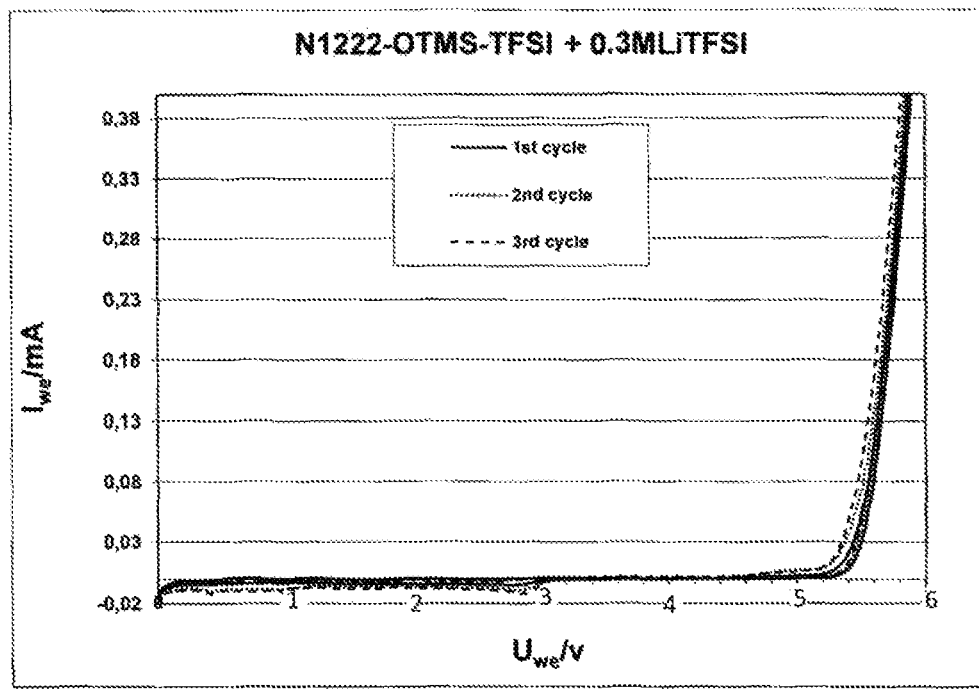
FIG. 12 shows the cyclic voltametry of N1222-OTMS-TFSI+LiTFSI.

A 0.3 molar solution of LiTFSI in the IL prepared in Example 3 was prepared by mixing 1.7225 g LiTFSI in 20 ml of the IL and charged into an electrochemical cell. This was a three electrodes cell having a Pt wire as a working electrode, a sheet of lithium metal as a counter electrode and another sheet of lithium metal as a reference electrode. The CV curve was measured between 0-6 V vs. Li at rate of 1 mV/s (FIG. 12).

Example 25—Compatibility of Electrolyte with Graphite

Figure 13:
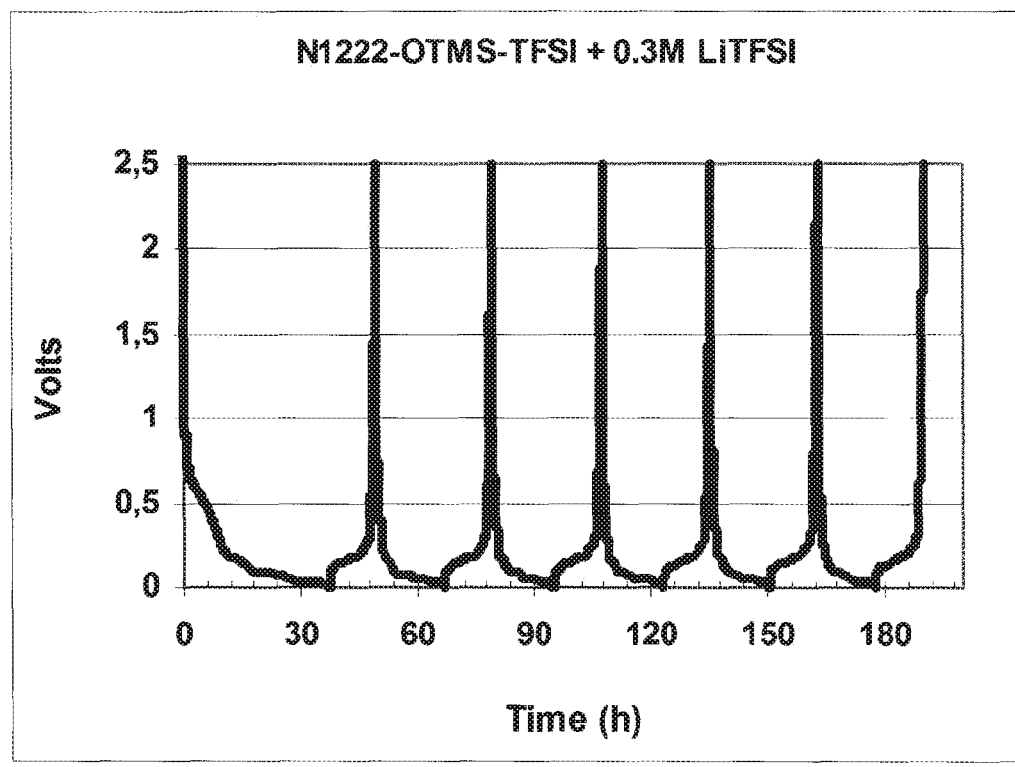
FIG. 13 shows the charge-discharge curves of graphite vs Li metal in a N1222-OTMS-TFSI based electrolyte.

The electrolyte prepared in Example 24 was tested in a three-electrode electrochemical cell with a graphite electrode. The anode material was prepared as described in Example 14. Two pieces of Li metal sheets were used as reference electrode and counter electrode and graphite was used as the working electrode. The cell was cycled between 0-2.5V versus Li at current rate C/24 (FIG. 13). The lithium intercalation in the graphite was successful with a low coulombic efficiency in the first cycle and increasing in the subsequent cycles up to 84% after 6 cycles at C/24 with a reversible capacity of 192 mAh/g.

Example 26—Compatibility of Electrolyte with SiOx

Figure 14:
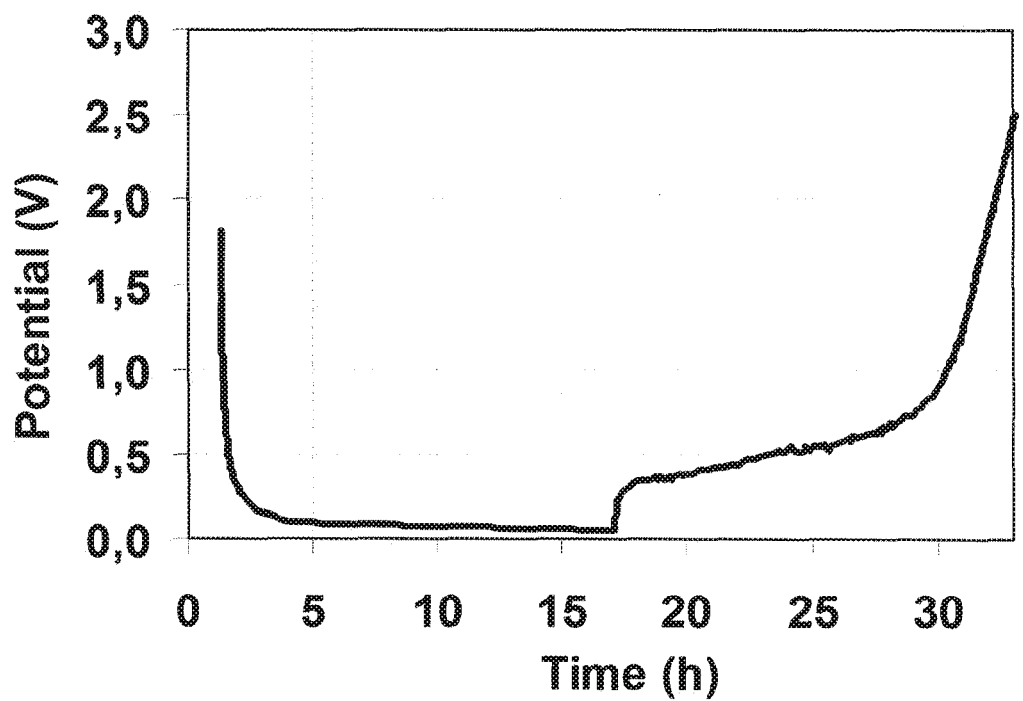
FIG. 14 shows the charge-discharge curves of SiOx vs Li metal in a N1122-OTMS-TFSI based electrolyte.

The electrolyte prepared in Example 11 was tested in a three-electrode electrochemical cell with a SiOx electrode. The negative electrode was prepared by mixing the SiOx powder, carbon black and alginate in a ratio 83:2:15% by weight in NMP and then coating this mixture on a copper current collector. The electrode material was dried at 150° C. in a vacuum oven for 12 h before use. Two pieces of Li metal sheets were used as reference and counter electrode and graphite was used as working electrode. The cell was cycled between 0.05-2.5V versus Li at current rate C/24 and 60° C. (FIG. 14). The lithium insertion in the SiOx material was successful with good coulombic efficiency in the first cycle (99%) at C/24 and with a reversible capacity of 520 mAh/g.

Example 27—Determination of Viscosities

Figure 15:
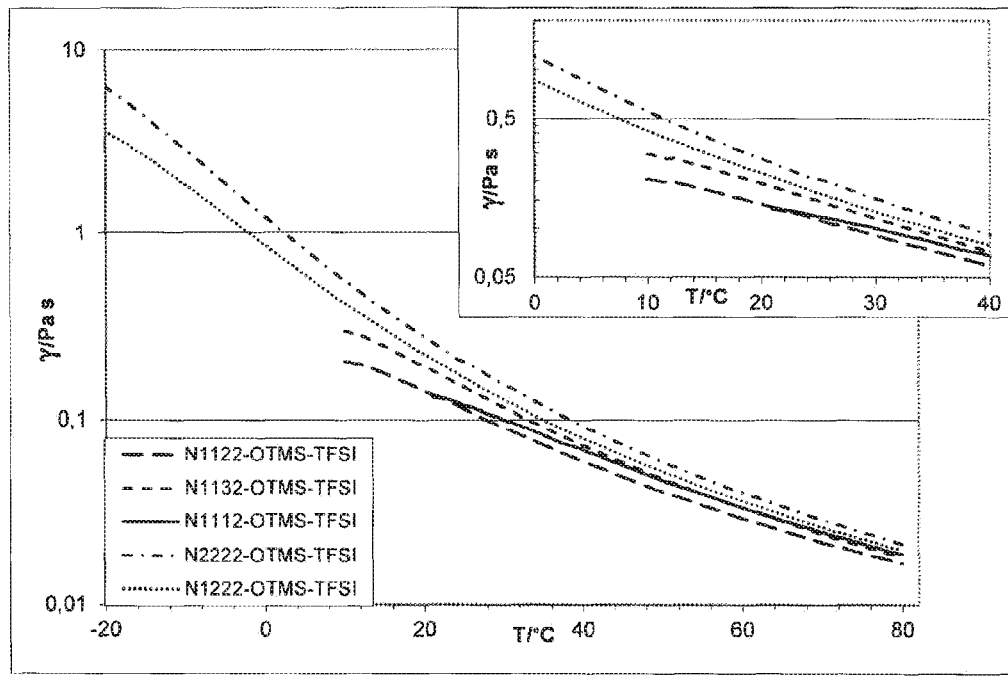
FIG. 15 shows the viscosity of the ionic compounds at different temperatures.

The viscosity of the above ionic liquids was determined using an Anton Paar Physica MCR301 instrument using PP50-SN5204 measuring equipment. At high temperature, a comparable viscosity was obtained for all the ionic liquids (FIG. 15). The viscosity increased in the following order: N1122-, N1112-, N1132-, N1222-, N2222-OTMS-TFSI.

Example 28—Determination of Conductivities

Figure 16:
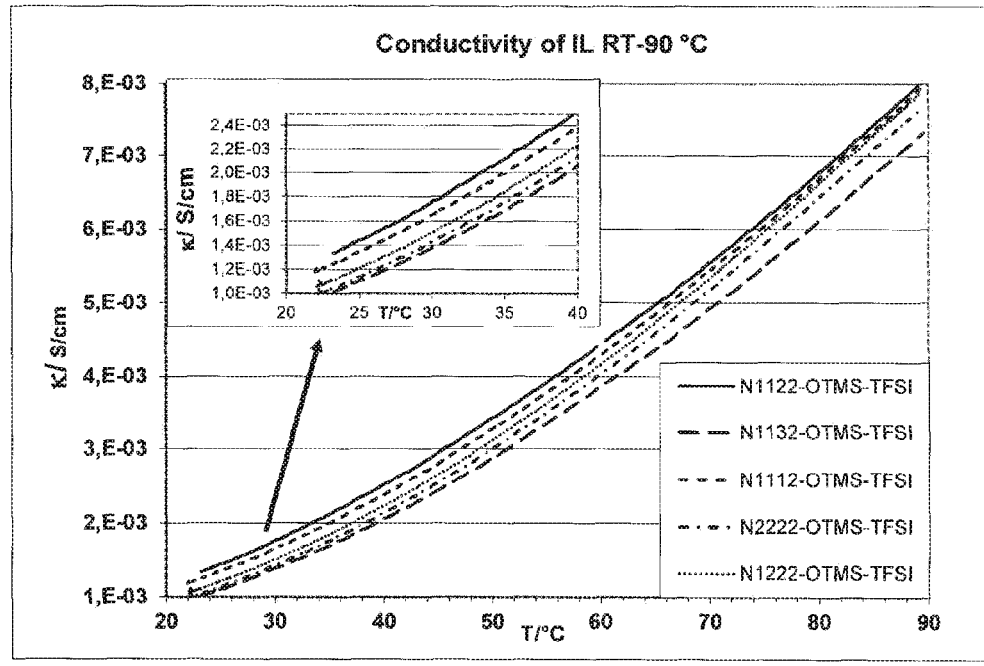
FIG. 16 shows the conductivity of the ionic compounds at different temperatures.

The conductivity of the ionic compounds/liquids was measured between room temperature and 90° C. using a MMulty Conductimeter made by Materials Mates Italia S.r.L. The conductivity measurements show conductivity of the different ionic compound or ionic liquid in the following order (FIG. 16): N1122→N1112→N2222→N1222→N1132-OTMS-TFSI. At 24° C., the highest value was $1.38\times10^{-3}$ (N1122) and lowest value was $1.05\times10^{-3}$ (N1132). At 60° C., the highest value was $4.41\times10^{-3}$ (N1122) and lowest value was $3.83\times10^{-3}$ (N1132).

Example 29—Preparation of N-ethyl-N-(2-(ethyldimethylsiloxy)ethyl)-N,N-dimethylammonium bis(trifluoromethanesulfonyl)amide (N1122-OEDMS-TFSI)

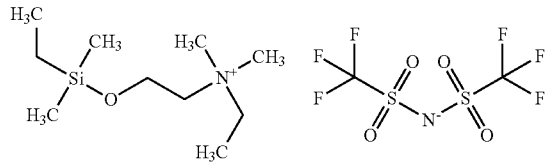

To a 250 ml round bottom flask containing 91 g (0.228 mol) of neat N-ethyl-N-2-hydroxyethyl-N,N-dimethylammonium TFSI prepared in a manner similar to that described in Example 4 a and b, 45 g (0.282 mol) of (diethylamino) ethyldimethylsilane were added at room temperature as a gentle stream of nitrogen was passed through the apparatus to facilitate removal of forming ammonia. The mixture was slowly heated to 60-70° C. and stirred so that a fine emulsion of silane in IL was formed. A vigorous evolution of gaseous diethylamine was observed as the temperature reached 60° C. This vigorous evolution lasted a few minutes. The mixture was heated and stirred for 5 hours after the end of the vigorous reaction. Then, the remaining silane, which was in a separate layer on the top of desired product, was evaporated under high vacuum. The product was dissolved in $CH_2Cl_2$ and activated charcoal was added. The mixture was heated to its boiling point, cooled to room temperature, filtered and again evaporated. Then, the round bottom flask was refilled 6 times with argon and again evacuated. The product was heated to 70° C. during this manipulation. Finally, the apparatus was cooled down under vacuum and refilled with argon. In this manner, 100 g (90%) of the title compound were obtained.

$^1$H NMR (300 MHz, CHLOROFORM-d) δ/ppm: 0.08 (s, 6H), 0.56 (q, J=8.19 Hz, 2H), 0.84-0.95 (m, 3H), 1.34 (t, J=7.32 Hz, 3H), 3.07 (s, 6H), 3.34-3.40 (m, 2H), 3.44 (q, J=7.60 Hz, 2H), 3.91-4.00 (m, 2H).

$^{13}$C NMR (75 MHz, CHLOROFORM-d) δ/ppm: −3.43 (s), 6.27 (s), 7.28 (s), 7.97 (s), 50.97 (t, J=3.45 Hz), 56.59 (s), 61.49 (br. s.), 64.58 (br. s.), 119.67 (q, J=320.70 Hz).

$^{19}$F NMR (470 MHz, CHLOROFORM-d) δ/ppm: −78.90 (s).

Example 30—Preparation of N-ethyl-N-(2-(triethylsiloxy)ethyl)-N,N-dimethylammonium bis(trifluoromethanesulfonyl)amide (N1122-OTES-TFSI)

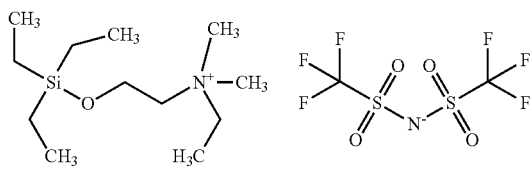

To a 250 ml round bottom flask containing 80 g (0.201 mol) of neat N-ethyl-N-2-hydroxyethyl-N,N-dimethylammonium TFSI prepared in a manner similar to Example 4a and b, 40 g (0.251 mol) of (dimethylamino)triethylsilane were added at room temperature as a gentle stream of nitrogen was passed through the apparatus to facilitate removal of forming ammonia. The mixture was slowly heated to 60-70° C. and stirred so that a fine emulsion of silane in IL was formed. A vigorous evolution of gaseous dimethylamine was observed as the temperature reached 60° C. This vigorous evolution lasted a few minutes. The mixture was heated and stirred for 4 hours after the end of the vigorous reaction. Then, the remaining silane, which was in a separate layer on the top of the desired product, was evaporated under high vacuum. The product was dissolved in $CH_2Cl_2$ and activated charcoal was added. The mixture was heated to its boiling point, cooled to room temperature, filtered, and again evaporated. Then, the round bottom flask was refilled 6 times with argon and again evacuated. The product was heated to 70° C. during this manipulation. Finally, the apparatus was cooled down under vacuum and refilled with argon. In this manner, 102 g (100%) of the title compound were obtained.

$^1$H NMR (300 MHz, CHLOROFORM-d) δ/ppm: 0.58 (q, J=8.20 Hz, 6H), 0.90 (t, J=8.20 Hz, 9H), 1.33 (t, J=7.32 Hz, 3H), 3.06 (s, 6H), 3.35-3.39 (m, 2H), 3.44 (q, J=7.02 Hz, 2H), 3.90-4.04 (m, 2H).
$^{13}$C NMR (75 MHz, CHLOROFORM-d) δ/ppm: 3.73 (s), 6.32 (s), 7.92 (s), 50.91 (t, J=3.45 Hz), 56.88 (s), 61.45 (br. s), 64.58 (br. s.), 119.65 (q, J=321.90 Hz).
$^{19}$F NMR (470 MHz, CHLOROFORM-d) δ/ppm: −78.90 (s).

Example 31—Preparation of N-ethyl-N-(2-(trimethylsiloxy)ethyl)-N,N-dimethylammonium N-fluorosulfonyl-trifluoromethansulfonylamide (N1122-OTMS-FTFSI)

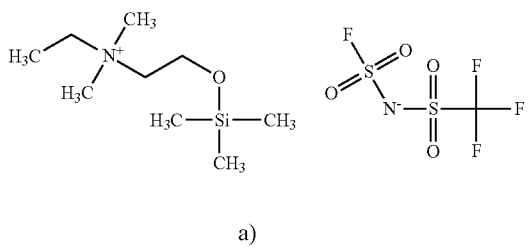

a) N-ethyl-N-2-hydroxyethyl-N,N-dimethylammonium N-fluorosulfonyl-trifluoromethansulfonylamide In a 250 ml round bottom flask, solutions of 60 g (0.304 mol) of N-ethyl-N-2-hydroxyethyl-N,N-dimethylammonium bromide (prepared in a manner similar to Example 4a) in 70 ml MQ water and 83 g (0.309 mol) of lithium N-fluorosulfonyl-trifluoromethansulfonylamide (Li-FTFSI) in 80 ml MQ water were mixed together under vigorous stirring. Phase separation occurred at once, but stirring was continued for another 4 hours at room temperature. Then, 100 ml of $CH_2Cl_2$ were added and the phases separated. The water phase was extracted with 50 ml of $CH_2Cl_2$ and the combined organic phases were washed 6 times with 100 ml of MQ water. A clear colourless solution was obtained. This solution was poured into a round bottom flask. The solvent was removed using a rotary evaporator and then under high vacuum at 60° C. In this manner, 89 g (84%) of pure N-ethyl-N-2-hydroxyethyl-N,N-dimethylammonium N-fluorosulfonyl-trifluoromethansulfonylamide were obtained.

$^1$H NMR (300 MHz, DMSO-d$_6$) δ/ppm: 1.15-1.34 (m), 3.03 (s), 3.32-3.44 (m), 3.83 (s), 5.27 (t, J=4.97 Hz).
$^{13}$C NMR (75 MHz, DMSO-d$_6$) δ/ppm: 7.87 (s), 49.98-50.75 (m), 55.09 (s), 59.44-60.37 (m), 64.02-64.60 (m), 119.74 (qd, J=321.90, 2.30 Hz).
$^{19}$F NMR (470 MHz, DMSO-d$_6$) δ/ppm: −77.98 (d, J=3.58 Hz, 3 F), 57.57 (q, J=3.97 Hz, 1 F).

b) N-ethyl-N-(2-(trimethylsiloxy)ethyl)-N,N-dimethylammonium N-fluorosulfonyl-trifluoromethansulfonylamide To a 250 ml round bottom flask containing 89 g (0.255 mol) of neat N-ethyl-N-2-hydroxyethyl-N,N-dimethylammonium FTFSI, 32 g (0.20 mol) of hexamethyldisilazane (HMDS) were added at room temperature as a gentle stream of nitrogen was passed through the apparatus to facilitate removal of forming ammonia. This mixture was slowly heated to 50° C. and stirred so that fine emulsion of HMDS in IL was formed. A vigorous evolution of gaseous ammonia was observed as the temperature reached 50° C. This vigorous evoluation lasted a few minutes. The mixture was heated and stirred for additional 4 hours after the end of the vigorous reaction. Then, the remaining HMDS, which was in a separate layer on the top of the desired product, was evaporated under high vacuum. Then, the round bottom flask was refilled 6 times with argon and again evacuated. The product was heated to 70° C. during this manipulation. Finally, the apparatus was cooled down under vacuum and refilled with argon. In this manner, 106 g (99%) of the title compound were obtained.

$^1$H NMR (300 MHz, CHLOROFORM-d) δ/ppm: 0.12 (s, 9H), 1.36 (t, J=7.02 Hz, 3H), 3.08 (s, 6H), 3.36-3.41 (m, 2H), 3.45 (q, J=7.60 Hz, 4H), 3.97 (s, 2H).
$^{13}$C NMR (75 MHz, CHLOROFORM-d) δ/ppm: −1.07 (s), 8.15 (s), 51.17 (t, J=3.45 Hz), 56.56 (s), 61.65 (br. s.), 64.75 (br. s.), 119.87 (qd, J=321.90, 2.30 Hz).
$^{19}$F NMR (470 MHz, CHLOROFORM-d) δ/ppm: −78.07 (d, J=4.17 Hz, 3 F), 57.52 (q, J=3.98 Hz, 1 F).

Example 32—Preparation of N-ethyl-N-(2-(trimethylsiloxy)ethyl)-N,N-dimethylammonium bis(fluorosulfonyl)amide (N1122-OTMS-FSI)

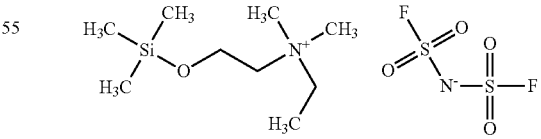

a) N-ethyl-N-2-hydroxyethyl-N,N-dimethylammonium bis(fluorosulfonyl)amide

In a 250 ml round bottom flask, solutions of 53 g (0.268 mol) of N-ethyl-N-2-hydroxyethyl-N,N-dimethylammonium bromide (prepared in a manner similar to Example 4a)

in 70 ml dry MeCN and 60 g (0.273 mol) of potassium bis(fluorosulfonyl)amide (K-FSI) in 80 ml dry MeCN were mixed under vigorous stirring. Phase separation occurred at once, but stirring was continued overnight at room temperature. Then, 100 ml of $CH_2Cl_2$ were added and KBr was filtered off. The filtrate was washed three times with 50 ml of $CH_2Cl_2$. A clear colourless solution was obtained which was poured into a round bottom flask. The solvent was removed using a rotary evaporator and then under high vacuum at 65° C. In this manner, 74 g (93%) of pure N-ethyl-N-2-hydroxyethyl-N,N-dimethylammonium bis (fluorosulfonyl)amide in the form of gelatinous crystals were obtained.

$^1$H NMR (300 MHz, DMSO-$d_6$) δ/ppm: 1.24 (tt, J=7.30, 1.80 Hz, 3H), 3.02 (s, 6H), 3.31-3.44 (m, 4H), 3.73-3.90 (m, 2H), 5.27 (t, J=4.97 Hz, 6H).

$^{13}$C NMR (75 MHz, DMSO-$d_6$) δ/ppm: 7.87 (s), 50.28 (t, J=3.40 Hz), 54.96 (s), 59.78 (t, J=2.30 Hz), 64.16 (t, J=2.30 Hz).

$^{19}$F NMR (470 MHz, DMSO-$d_6$) δ/ppm: 53.18 (s).

b) N-ethyl-N-(2-(trimethylsiloxy)ethyl)-N,N-dimethylammonium bis(fluorosulfonyl)amide To a 250 ml round bottom flask containing 74 g (0.237 mol) of N-ethyl-N-2-hydroxyethyl-N,N-dimethylammonium FSI dissolved in 80 ml of dry MeCN, 32 g (0.20 mol) of hexamethyldisilazane (HMDS) were added at room temperature as a gentle stream of nitrogen was passed through the apparatus to facilitate removal of forming ammonia. The mixture was slowly heated to 40° C. and stirred. A vigorous evolution of gaseous ammonia started immediately and lasted a few minutes. The mixture was heated and stirred for 4 hours after the end of the vigorous reaction. Then, volatiles were evaporated under high vacuum. What remained was dissolved in $CH_2Cl_2$, purified with activated charcoal, filtered and evaporated. Then, the round bottom flask was refilled 6 times with argon and again evacuated. The product was heated to 70° C. during this manipulation. Finally, the apparatus was cooled down under vacuum and refilled with argon. In this manner, 74 g (85%) of title compound as a colourless liquid were obtained.

$^1$H NMR (300 MHz, CHLOROFORM-d) δ/ppm: 0.08 (s, 9H), 1.32 (t, J=7.32 Hz, 3H), 3.03 (s, 6H), 3.30-3.35 (m, 2H), 3.39 (q, J=7.20 Hz, 2H), 3.93 (dt, J=4.24, 2.27 Hz, 2H).

$^{13}$C NMR (75 MHz, CHLOROFORM-d) δ/ppm: −1.31 (s), 7.88 (s), 50.91 (t, J=3.45 Hz), 56.25 (s), 61.36 (br. s.), 64.52 (t, J=2.30 Hz).

$^{19}$F NMR (470 MHz, CHLOROFORM-d) δ/ppm: 53.04 (s).

Example 33—Preparation of N-ethyl-N-(3-(trimethylsiloxy)propyl)-N,N-dimethylammonium bis(trifluoromethanesulfonyl)amide (N1123-OTMS-TFSI)

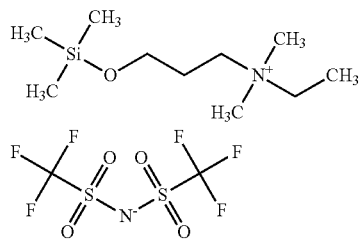

a)
N-ethyl-N-(3-hydroxypropyl)-N,N-dimethylammonium chloride

In a 300 ml 316 SS autoclave equipped with a magnetic stirrer were placed 94.5 g (1 mol) of 3-chloropropanol and 74 g (1.01 mol) of ethyldimethylamine. The mixture was stirred and heated to 140° C. for 24 h using a stirring hot plate. After cooling, the resulting waxy solid was dissolved in 350 ml MeOH, boiled with activated charcoal, cooled and filtered. The filtrate was evaporated to dryness and the product was isolated as a colourless crystalline solid. Altogether, 150 g (90%) of N-ethyl-N-(3-hydroxypropyl)-N,N-dimethylammonium chloride were obtained.

$^1$H NMR (300 MHz, DMSO-$d_6$) δ/ppm 1.21 (t, J=7.02 Hz, 3H), 1.71-1.88 (m, 2H), 3.02 (s, 6H), 3.30-3.40 (m, 4H), 3.39-3.49 (m, 2H), 5.13 (t, J=5.27 Hz, 1H).

$^{13}$C NMR (75 MHz, DMSO-$d_6$) δ/ppm: 7.79 (s), 25.29 (s), 49.47 (t, J=3.45 Hz), 57.48 (s), 58.26 (br. s.), 60.36 (br. s.).

b) N-ethyl-N-(2-hydroxypropyl)-N,N-dimethylammonium bis(trifluoromethanesulfonyl)amide In a 250 ml round bottom flask, solutions of 60 g (0.358 mol) of N-ethyl-N-(3-hydroxypropyl)-N,N-dimethylammonium chloride in 70 ml MQ water and 104 g (0.360 mol) of LiTFSI in 80 ml MQ water were mixed together under vigorous stirring. Phase separation occurred at once, but stirring was continued for another 4 hours at room temperature. Then, 100 ml of $CH_2Cl_2$ were added and the phases separated. The water phase was extracted with 50 ml of $CH_2Cl_2$ and the combined organic phases were washed 6 times with 100 ml of MQ water. A clear colourless solution was obtained. This solution was poured into a round bottom flask. The solvent was removed using a rotary evaporator and then under high vacuum at 60° C. In this manner, 111.2 g (75%) of pure N-ethyl-N-(2-hydroxypropyl)-N,N-dimethylammonium bis(trifluoromethanesulfonyl)amide as a colourless liquid were obtained.

$^1$H NMR (300 MHz, DMSO-$d_6$) δ/ppm: 1.18-1.30 (m, 3H), 1.73-1.86 (m, 2H), 2.98 (s, 6H), 3.22-3.39 (m, 4H), 3.49 (q, J=5.27 Hz, 2H), 4.78 (t, J=4.68 Hz, 1H).

$^{13}$C NMR (75 MHz, DMSO-$d_6$) δ/ppm: 7.68 (s), 25.31 (s), 49.20-49.78 (m), 57.66 (s), 58.56 (br. s.), 60.07-61.14 (m), 119.58 (q, J=321.80 Hz).

$^{19}$F NMR (470 MHz, DMSO-$d_6$) δ/ppm: −78.78 (s).

c) N-ethyl-N-(3-trimethylsiloxypropyl)-N,N-dimethylammonium bis(trifluoromethanesulfonyl)amide To a 250 ml round bottom flask containing 111 g (0.269 mol) of neat N-ethyl-N-(3-hydroxypropyl)-N,N-dimethylammonium TFSI, 43 g (0.266 mol) of hexamethyldisilazane (HMDS) were added at room temperature as a gentle stream of nitrogen was passed through the apparatus to facilitate removal of forming ammonia. The mixture was slowly heated to 60-70° C. and stirred so that a fine emulsion of HMDS in IL was formed. A vigorous evolution of gaseous ammonia was observed as the temperature reached 60° C. This evolution lasted a few minutes. The mixture was heated and stirred for 4 hours after the end of the vigorous reaction. Then, the remaining HMDS, which was in a separate layer on top of the desired product, was evaporated under high vacuum. Then, the round bottom flask was refilled 6 times with argon and again evacuated. The product was heated to 70° C. during this manipulation. Finally, the apparatus was cooled down under vacuum and refilled with argon. In this manner, 129 g (99%) of the title compound in the form of a colourless liquid were obtained.

$^1$H NMR (300 MHz, CHLOROFORM-d) δ/ppm: 0.04 (s, 9H), 1.30 (t, J=7.02 Hz, 3H), 1.78-1.97 (m, 2H), 2.96 (s, 6H), 3.23-3.37 (m, 4H), 3.60 (t, J=5.56 Hz, 2H).

$^{13}$C NMR (75 MHz, CHLOROFORM-d) δ/ppm: −1.12 (s), 7.65 (s), 25.37 (s), 50.29 (t, J=3.45 Hz), 58.16 (s), 59.61 (br. s.), 61.41 (br. s.), 119.61 (q, J=321.90 Hz).

$^{19}$F NMR (470 MHz, CHLOROFORM-d) δ/ppm: −79.22 (s).

Example 34—Preparation of N-ethyl-N-(4-(trimethylsiloxy)butyl)-N,N-dimethylammonium bis(trifluoromethanesulfonyl)amide (N1124-OTMS-TFSI)

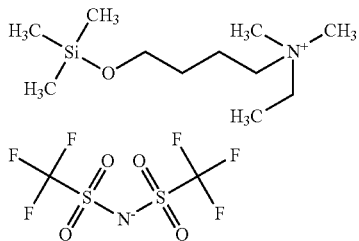

a)
N-ethyl-N-(4-hydroxybutyl)-N,N-dimethylammonium chloride

In a 300 ml 316 SS autoclave equipped with a magnetic stirrer were placed 50 g of 86% (0.391 mol) of 4-chlorobutanol and 34 g (0.469 mol) of ethyldimethylamine. The mixture was stirred and heated to 150° C. for 30 h using a stirring hot plate. After cooling, the resulting waxy solid was dissolved in water, basified with NaOH to remove unquaternised amine, and finally evaporated to dryness. Altogether, 56.8 g (approx. 70%) of N-ethyl-N-(4-hydroxybutyl)-N,N-dimethylammonium chloride as a mixture with NaCl and NaOH were obtained.

$^1$H NMR (300 MHz, DMSO-d$_6$) δ/ppm 1.09-1.25 (m, 3H), 1.27-1.46 (m, 2H), 1.64 (dt, J=16.09, 7.75 Hz, 2H), 2.99 (s, 6H), 3.20-3.45 (m, 6H), 4.40 (br. s, 1H).

$^{13}$C NMR (75 MHz, DMSO-d$_6$) δ/ppm: 7.96 (s), 18.93 (s), 30.14 (s), 49.43 (br. s.), 58.32 (br. s.), 60.15 (s), 62.53 (s).

b) N-ethyl-N-(4-hydroxybutyl)-N,N-dimethylammonium bis(trifluoromethanesulfonyl)amide In a 250 ml round bottom flask, a water solution of the mixture obtained in a) above was neutralised with HCl and mixed with a solution of 87 g (0.300 mol) of LiTFSI in 80 ml MQ water under vigorous stirring. Phase separation occurred at once, but stirring was continued for another 4 hours at room temperature. Then, 100 ml of CH$_2$Cl$_2$ were added and the phases separated. The water phase was extracted with 50 ml of CH$_2$Cl$_2$ and the combined organic phases were washed 6 times with 100 ml of MQ water. A clear colourless solution was obtained. It was poured into a round bottom flask. The solvent was removed using a rotary evaporator and then under high vacuum at 60° C. In this manner, 53.29 g of pure N-ethyl-N-(4-hydroxybutyl)-N,N-dimethylammonium bis(trifluoromethanesulfonyl)amide as a colourless liquid were obtained.

$^1$H NMR (300 MHz, DMSO-d$_6$) δ/ppm: 1.15-1.30 (m, 3H), 1.37-1.58 (m, 2H), 1.61-1.80 (m, 2H), 2.89-3.00 (m, 6H), 3.16-3.38 (m, 4H), 3.41-3.52 (m, 2H), 4.55 (s, 1H).

$^{13}$C NMR (75 MHz, DMSO-d$_6$) δ/ppm: 18.70 (s), 29.06 (s), 48.98-49.88 (m), 58.55 (br. s.), 59.91 (s), 62.45 (br. s.), 70.05 (s), 119.56 (q, J=321.90 Hz).

$^{19}$F NMR (470 MHz, DMSO-d$_6$) δ/ppm: −75.36 (s).

c) N-ethyl-N-(4-trimethylsiloxybutyl)-N,N-dimethylammonium bis(trifluoromethanesulfonyl)amide To a 250 ml round bottom flask containing 53 g (0.125 mol) of neat N-ethyl-N-(4-hydroxybutyl)-N,N-dimethylammonium TFSI, 20 g (0.125 mol) of hexamethyldisilazane (HMDS) were added at room temperature as a gentle stream of nitrogen was passed through the apparatus to facilitate removal of forming ammonia. The mixture was slowly heated to 60-70° C. and stirred so that a fine emulsion of HMDS in IL was formed. A vigorous evolution of gaseous ammonia was observed as the temperature reached 60° C. This evolution lasted a few minutes. The mixture was heated and stirred for 4 hours after the end of the vigorous reaction. Then, volatiles were evaporated under high vacuum. What remained was dissolved in CH$_2$Cl$_2$, purified with activated charcoal, filtered and evaporated. Then, the round bottom flask was refilled 6 times with argon and again evacuated. The product was heated to 70° C. during this manipulation. Finally, the apparatus was cooled down under vacuum and refilled with argon. In this manner, 47 g (74%) of the title compound as a colourless liquid were obtained.

$^1$H NMR (300 MHz, CHLOROFORM-d) δ/ppm: 0.07 (s, 9H), 1.33 (t, J=7.32 Hz, 3H), 1.46-1.64 (m, 2H), 1.67-1.86 (m, 2H), 2.98 (s, 6H), 3.15-3.28 (m, 2H), 3.34 (q, J=7.02 Hz, 2H), 3.60 (t, J=5.85 Hz, 2H).

$^{13}$C NMR (75 MHz, CHLOROFORM-d) δ/ppm: −0.83 (s), 7.83 (s), 19.26 (s), 28.49 (s), 50.13 (br. s.), 59.70 (br. s.), 61.04 (s), 63.54 (br. s), 119.69 (q, J=321.90 Hz).

$^{19}$F NMR (470 MHz, CHLOROFORM-d) δ/ppm: −79.16 (s).

Example 35—Preparation of N-ethyl-N-(6-(trimethylsiloxy)hexyl)-N,N-dimethylammonium bis(trifluoromethanesulfonyl)amide (N1126-OTMS-TFSI)

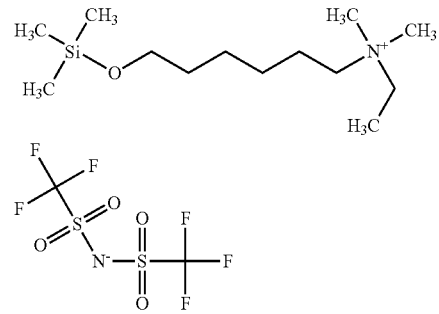

a)
N-ethyl-N-(6-hydroxyhexyl)-N,N-dimethylammonium chloride

In a 300 ml 316 SS autoclave equipped with a magnetic stirrer were placed 25 g of (0.183 mol) of 6-chlorohexanol, 16 g (0.220 mol) of ethyldimethylamine and 50 mg of KI. The mixture was stirred and heated to 100° C. for 72 h using a stirring hot plate. After cooling, the resulting waxy solid was crushed and evacuated at 80° C./1.4 mm Hg, and finally recrystallised from MeOH/acetone. Altogether, 38 g (99%) of N-ethyl-N-(6-hydroxyhexyl)-N,N-dimethylammonium chloride were obtained.

$^1$H NMR (300 MHz, DMSO-$d_6$) δ/ppm 1.21 (t, J=7.10 Hz, 3H), 1.24-1.48 (m, 6H), 1.55-1.71 (m, 2H), 3.00 (s, 6H), 3.18-3.30 (m, 2H), 3.30-3.43 (m, 4H), 4.55 (t, J=4.97 Hz, 1H).

$^{13}$C NMR (75 MHz, DMSO-$d_6$) δ/ppm: 7.82 (s), 21.66 (br. s), 25.00 (br. s), 25.67 (br. s), 32.17 (s), 49.30 (t, J=3.40 Hz), 58.29 (br. s.), 60.38 (s), 62.21 (br. s.).

b) N-ethyl-N-(6-hydroxyhexyl)-N,N-dimethylammonium bis(trifluoromethanesulfonyl)amide In a 250 ml round bottom flask, solutions of 30 g (0.143 mol) of N-ethyl-N-(6-hydroxyhexyl)-N,N-dimethylammonium chloride and 43 g (0.150 mol) of LiTFSI in 80 ml MQ water were mixed together under vigorous stirring. Phase separation occurred at once, but stirring was continued for another 4 hours at room temperature. Then, 100 ml of CH$_2$Cl$_2$ were added and the phases separated. The water phase was extracted with 50 ml of CH$_2$Cl$_2$ and the combined organic phases were washed 6 times with 100 ml of MQ water. A clear solution was obtained. This solution was poured into a round bottom flask. The solvent was removed using a rotary evaporator and then under high vacuum at 60° C. In this manner, 58.4 g (90%) of pure N-ethyl-N-(6-hydroxyhexyl)-N,N-dimethylammonium bis(trifluoromethanesulfonyl)amide as liquid were obtained.

$^1$H NMR (300 MHz, DMSO-$d_6$) δ/ppm: 1.23 (t, J=7.20 Hz, 3H), 1.27-1.51 (m, 6H), 1.55-1.76 (m, 2H), 2.96 (s, 6H), 3.14-3.25 (m, 2H), 3.31 (q, J=7.02 Hz, 2H), 3.40 (t, J=6.15 Hz, 2H), 4.36 (br. s., 1H).

$^{13}$C NMR (75 MHz, DMSO-$d_6$) δ/ppm: 7.70 (s), 21.74 (s), 25.03 (s), 25.67 (s), 32.23 (s), 48.68-49.74 (m), 58.58 (br. s), 60.55 (s), 62.53 (br. s.), 119.56 (q, J=321.90 Hz).

$^{19}$F NMR (470 MHz, DMSO-$d_6$) δ/ppm: −78.79 (s).

c) N-ethyl-N-(6-trimethylsiloxyhexyl)-N,N-dimethylammonium bis(trifluoromethanesulfonyl)amide To a 250 ml round bottom flask containing 58 g (0.129 mol) of neat N-ethyl-N-(4-hydroxybutyl)-N,N-dimethylammonium TFSI, 20 g (0.129 mol) of hexamethyldisilazane (HMDS) were added at room temperature as a gentle stream of nitrogen was passed through the apparatus to facilitate the removal of forming ammonia. The mixture was slowly heated to 60-70° C. and stirred so that a fine emulsion of HMDS in IL was formed. A vigorous evolution of gaseous ammonia was observed as the temperature reached 60° C. This evolution lasted a few minutes. The mixture was heated and stirred for 4 hours after the end of the vigorous reaction. Then, the volatiles were evaporated under high vacuum. What remained was dissolved in CH$_2$Cl$_2$, purified with activated charcoal, filtered and evaporated. Then, the round bottom flask was refilled 6 times with argon and again evacuated. The product was heated to 70° C. during this manipulation. Finally, the apparatus was cooled down under vacuum and refilled with argon. In this manner, 63 g (93%) of the title compound as a viscous liquid were obtained.

$^1$H NMR (300 MHz, CHLOROFORM-d) δ/ppm: 0.05 (s, 9H), 1.22-1.41 (m, 7H), 1.47 (d, J=7.02 Hz, 2H), 1.55-1.75 (m, 2H), 2.96 (s, 6H), 3.10-3.22 (m, 2H), 3.31 (q, J=7.00 Hz, 2H), 3.52 (t, J=6.15 Hz, 2H).

$^{13}$C NMR (75 MHz, CHLOROFORM-d) δ/ppm: −0.76 (s), 7.82 (s), 22.31 (s), 25.09 (s), 25.62 (s), 32.10 (s), 50.01 (br. s.), 59.68 (br. s), 61.99 (s), 63.83 (br. s), 119.64 (q, J=321.90 Hz).

$^{19}$F NMR (470 MHz, CHLOROFORM-d) δ/ppm: −79.16 (s).

Example 36—Preparation of N-ethyl-N-2-(2-(trimethylsiloxy)ethoxy)ethyl-N,N-dimethylammonium bis(trifluoromethanesulfonyl)amide (N1122O2-OTMS-TFSI)

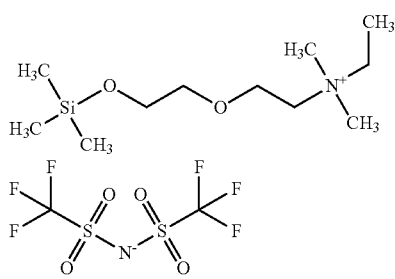

a) N-ethyl-N-2-(2-hydroxyethoxy)ethyl-N,N-dimethylammonium chloride

In a 300 ml 316 SS autoclave equipped with a magnetic stirrer were placed 50 g of (0.401 mol) of 2-chloroethyl 2-hydroxyethyl ether, 35 g (0.482 mol) of ethyldimethylamine and 50 mg of KI. The mixture was stirred and heated to 150° C. for 22 h using a stirring hot plate. After cooling, the resulting very viscous liquid (with a consistence similar to honey) was dissolved in water, basified with NaOH, evaporated and dissolved in CH$_2$Cl$_2$. Activated charcoal was then added. The mixture was stirred overnight, filtered and evaporated. Altogether, 72 g (91%) of colourless N-ethyl-N-2-(2-hydroxyethoxy)ethyl-N,N-dimethylammonium chloride were obtained.

$^1$H NMR (300 MHz, DMSO-$d_6$) δ/ppm 1.13-1.28 (m, 3H), 3.03-3.18 (m, 6H), 3.39-3.51 (m, 6H), 3.58 (d, J=4.10 Hz, 2H), 3.81 (br. s., 2H), 5.06 (br. s., 1H).

$^{13}$C NMR (75 MHz, DMSO-$d_6$) δ/ppm: 8.02 (s), 50.08 (br. s.), 59.45 (s), 59.75 (s), 61.60 (s), 63.87 (s), 72.08 (s).

b) N-ethyl-N-2-(2-hydroxyethoxy)ethyl-N,N-dimethylammonium bis(trifluoromethanesulfonyl)amide In a 250 ml round bottom flask, solutions of 47 g (0.290 mol) of N-ethyl-N-2-(2-hydroxyethoxy)ethyl-N,N-dimethylammonium chloride and 100 g (0.348 mol) of LiTFSI in 80 ml MQ water were mixed together under vigorous stirring. Phase separation occurred at once, but stirring was continued for another 4 hours at room temperature. Then, 100 ml of CH$_2$Cl$_2$ were added and the phases separated. The water phase was extracted with 50 ml of CH$_2$Cl$_2$ and the combined organic phases were washed 6 times with 100 ml of MQ water. A clear solution was obtained. It was poured into a round bottom flask. The solvent was removed using a rotary evaporator and then under high vacuum at 60° C. In this manner, 121.8 g (92%) of pure N-ethyl-N-2-(2-hydroxyethoxy)ethyl-N,N-dimethylammonium bis(trifluoromethanesulfonyl)amide as a liquid were obtained.

$^1$H NMR (300 MHz, DMSO-d$_6$) δ/ppm: 1.26 (t, J=7.32 Hz, 3H), 3.04 (s, 6H), 3.41 (q, J=7.41 Hz, 2H), 3.46-3.62 (m, 6H), 3.83 (br. s., 2H), 4.64 (t, J=4.97 Hz, 1H).
$^{13}$C NMR (75 MHz, DMSO-d$_6$) δ/ppm: 7.81 (s), 50.36 (br. s), 60.15 (br. s), 62.16 (br. s.), 64.01 (s), 72.39 (s), 119.68 (q, J=321.90 Hz).
$^{19}$F NMR (470 MHz, DMSO-d$_6$) δ/ppm: −79.10 (s).

c) N-ethyl-N-2-(2-(trimethylsiloxy)ethoxy)ethyl-N,N-dimethylammonium bis(trifluoromethanesulfonyl)amide To a 250 ml round bottom flask containing 121.8 g (0.275 mol) of neat N-ethyl-N-2-(2-hydroxyethoxy)ethyl-N,N-dimethylammonium TFSI, 44 g (0.273 mol) of hexamethyldisilazane (HMDS) were added at room temperature as a gentle stream of nitrogen was passed through the apparatus to facilitate the removal of forming ammonia. The mixture was slowly heated to 60-70° C. and stirred so that a fine emulsion of HMDS in IL was formed. A vigorous evolution of gaseous ammonia was observed as the temperature reached 60° C. The evoluation lasted a few minutes. The mixture was heated and stirred for 4 hours after the end of the vigorous reaction. Then, volatiles were evaporated under high vacuum. What remained was dissolved in CH$_2$Cl$_2$, purified with activated charcoal, filtered and evaporated. Then, the round bottom flask was refilled 6 times with argon and again evacuated. The product was heated to 70° C. during this manipulation. Finally, the apparatus was cooled down under vacuum and refilled with argon. In this manner, 140 g (99%) of the title compound as a viscous liquid were obtained.
$^1$H NMR (300 MHz, CHLOROFORM-d) δ/ppm: 0.06 (s, 9H), 1.33 (t, J=7.02 Hz, 3H), 3.03-3.11 (m, 6H), 3.37-3.49 (m, 4H), 3.49-3.56 (m, 2H), 3.62-3.71 (m, 2H), 3.85 (br. s., 2H).
$^{13}$C NMR (75 MHz, CHLOROFORM-d) δ/ppm: −0.88 (s), 7.97 (s), 50.96 (br. s.), 61.30 (s), 61.42 (br. s), 62.72 (br. s.), 64.41 (s), 72.45 (s), 119.64 (q, J=321.90 Hz).
$^{19}$F NMR (470 MHz, CHLOROFORM-d) δ/ppm: −79.18 (s).

Example 37—Preparation of 3-methyl-1-(2-(trimethylsiloxy)ethyl)imidazolium bis(trifluoromethanesulfonyl)amide (Im12-OTMS-TFSI)

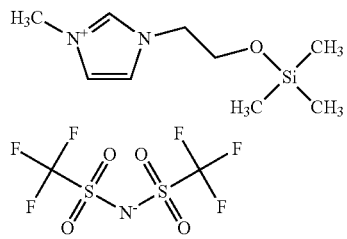

a) 1-(2-hydroxyethyl)-3-methylimidazolium bromide

In a 250 ml round bottom flask equipped with a magnetic stirrer were placed 49 g (0.597 mol) of 1-methylimidazole. These were dissolved in 60 ml of MeCN. To this solution, 76 g (0.610 mol) of 2-bromoethanol were added dropwise in 15 min. The mixture was stirred refluxed for 48 hours during which no sign of completed phase separation was observed. The mixture was heated to reflux for 2 h and cooled to room temperature. The solvents were evaporated and the resulting solid was purified by pouring its methanolic solution into a 1:1 mixture of ethyl acetate (AcOEt) and acetone. The resulting white powder was filtered and washed with fresh ethyl acetate and dried under vacuum. 125 g (95%) of 1-(2-hydroxyethyl)-3-methylimidazolium bromide were obtained.
$^1$H NMR (300 MHz, DMSO-d$_6$) δ/ppm: 3.70 (q, J=5.13 Hz, 2H), 3.88 (s, 3H), 4.24 (t, J=4.94 Hz, 2H), 5.15 (t, J=5.31 Hz, 1H), 7.76 (d, J=1.46 Hz, 1H), 7.79 (t, J=1.65 Hz, 1H), 9.23 (s, 1H).
$^{13}$C NMR (75 MHz, DMSO-d$_6$) δ/ppm: 35.73 (s), 51.53 (s), 59.26 (s), 122.61 (s), 123.28 (s), 136.76 (s)

b) 1-(2-hydroxyethyl)-3-methylimidazolium bis(trifluoromethanesulfonyl)amide

In a 250 ml round bottom flask, a water solution of 59 g (0.285 mol) of 1-(2-hydroxyethyl)-3-methylimidazolium bromide and a solution of 82.3 g (0.287 mol) of LiTFSI in 80 ml MQ water were mixed together under vigorous stirring. Phase separation occurred at once, but stirring was continued for another 4 hours at room temperature. Then, 100 ml of CH$_2$Cl$_2$ were added and the phases separated. The water phase was extracted with 50 ml of CH$_2$Cl$_2$ and the combined organic phases were washed 6 times with 100 ml of MQ water. A clear solution was obtained. It was poured into a round bottom flask. The solvent was removed using a rotary evaporator and then under high vacuum at 60° C. In this manner, 69 g (60%) of pure 1-(2-hydroxyethyl)-3-methylimidazolium bis(trifluoromethanesulfonyl)amide as colourless liquid were obtained.
$^1$H NMR (300 MHz, DMSO-d$_6$) δ/ppm: 3.74 (q, J=4.88 Hz, 2H), 3.86 (s, 3H), 4.16-4.25 (m, 2H), 5.18 (t, J=5.13 Hz, 1H), 7.63 (t, J=1.65 Hz, 1H), 7.68 (t, J=1.83 Hz, 1H), 9.05 (s, 1H).
$^{13}$C NMR (75 MHz, DMSO-d$_6$) δ/ppm $^{13}$C NMR (75 MHz, DMSO-d$_6$) δ ppm 35.73 (s, 9 C), 51.85 (s, 12 C), 59.49 (s, 12 C), 119.68 (q, J=321.80 Hz, 8 C), 122.77 (s, 12 C), 123.43 (s, 12 C), 137.01 (s, 8 C).

c) 3-methyl-1-(2-(trimethylsiloxy)ethyl)imidazolium bis(trifluoromethanesulfonyl)amide To a 250 ml round bottom flask containing 68 g (0.167 mol) of neat 1-(2-hydroxyethyl)-3-methylimidazolium TFSI, 25.8 g (0.160 mol) of hexamethyldisilazane (HMDS) were added at room temperature as a gentle stream of nitrogen was passed through the apparatus to facilitate removal of forming ammonia. The mixture was slowly heated to 50-60° C. and stirred so that a fine emulsion of HMDS in IL was formed. A vigorous evolution of gaseous ammonia was observed as the temperature reached 60° C. The evoluation lasted a few minutes. The mixture was heated and stirred for 4 hours after the end of the vigorous reaction. Then, the volatiles were evaporated under high vacuum. What remained was dissolved in CH$_2$Cl$_2$, purified with activated charcoal, filtered and evaporated. Then, the round bottom flask was refilled 6 times with argon and again evacuated. The product was heated to 70° C. during this manipulation. Finally, the apparatus was cooled down under vacuum and refilled with argon. In this manner, 70 g (88%) of the title compound as a viscous liquid were obtained ¹H NMR (300 MHz, CHLOROFORM-d) δ/ppm: 0.03 (s, 9H), 3.79-3.86 (m, 2H), 3.89 (s, 3H), 4.17-4.29 (m, 2H), 7.31 (t, J=1.83 Hz, 1H), 7.37 (t, J=1.65 Hz, 1H), 8.59 (br. s, 1H).
¹³C NMR (75 MHz, CHLOROFORM-d) δ/ppm: −1.21 (s), 36.03 (s), 52.01 (s), 60.46 (s), 119.63 (q, J=320.70 Hz), 123.06 (s), 123.15 (s), 135.97 (s).

Example 38—CV of N-ethyl-N-(2-(ethyldimethylsiloxy)ethyl)-N,N-dimethylammonium bis(trifluoromethanesulfonyl)amide (N1122-OEDMS-TFSI)

Figure 17:
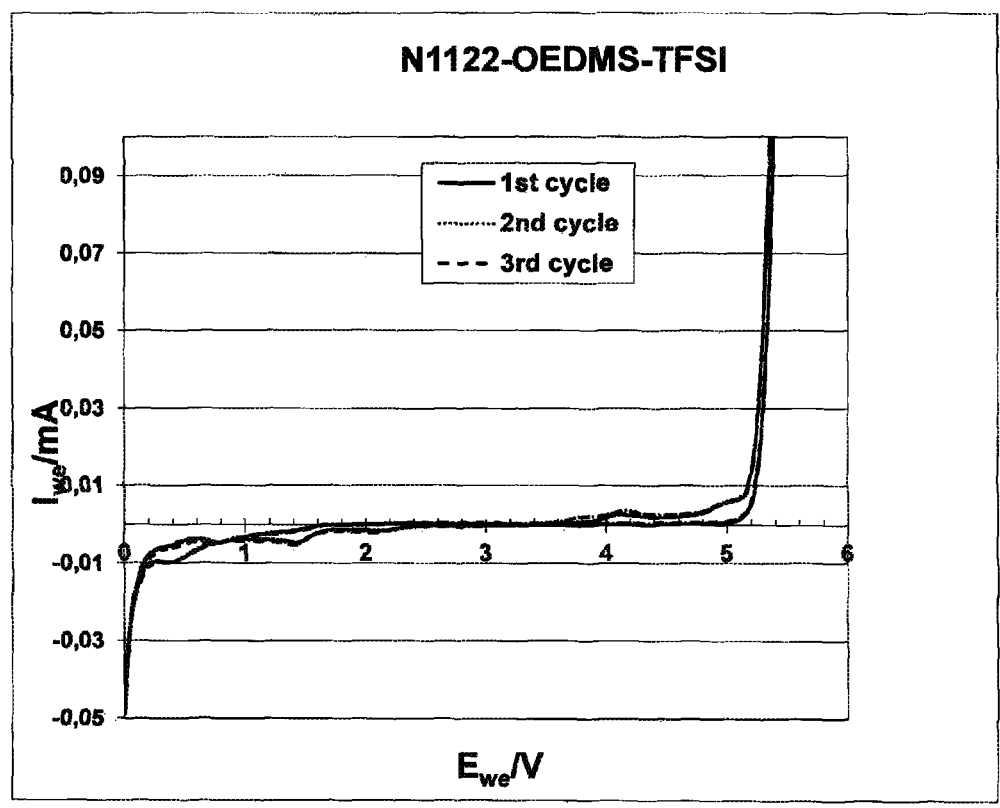
FIG. 17 shows the cyclic voltametry of N1122-OEDMS-TFSI.

The compound prepared in Example 29 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 17).

Example 39—CV of N-ethyl-N-(2-(triethylsiloxy)ethyl)-N,N-dimethylammonium bis(trifluoromethanesulfonyl)amide (N1122-OTES-TFSI)

Figure 18:
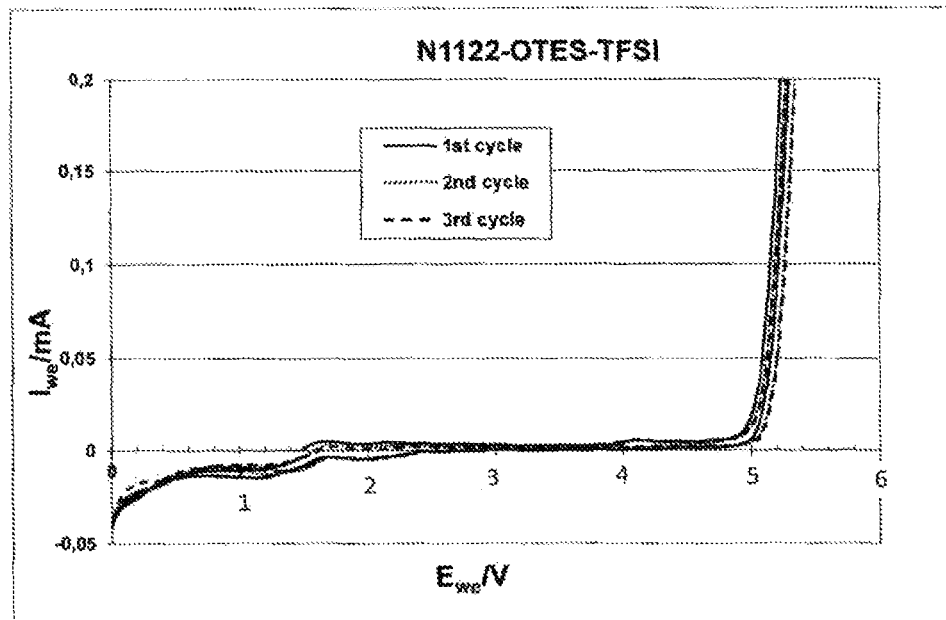
FIG. 18 shows the cyclic voltametry of N1122-OTES-TFSI.

The compound prepared in Example 30 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 18).

Example 40—CV of N-ethyl-N-(2-(trimethylsiloxy)ethyl)-N,N-dimethylammonium N-fluorosulfonyl-trifluoromethansulfonylamide (N1122-OTMS-FTFSI)

Figure 19:
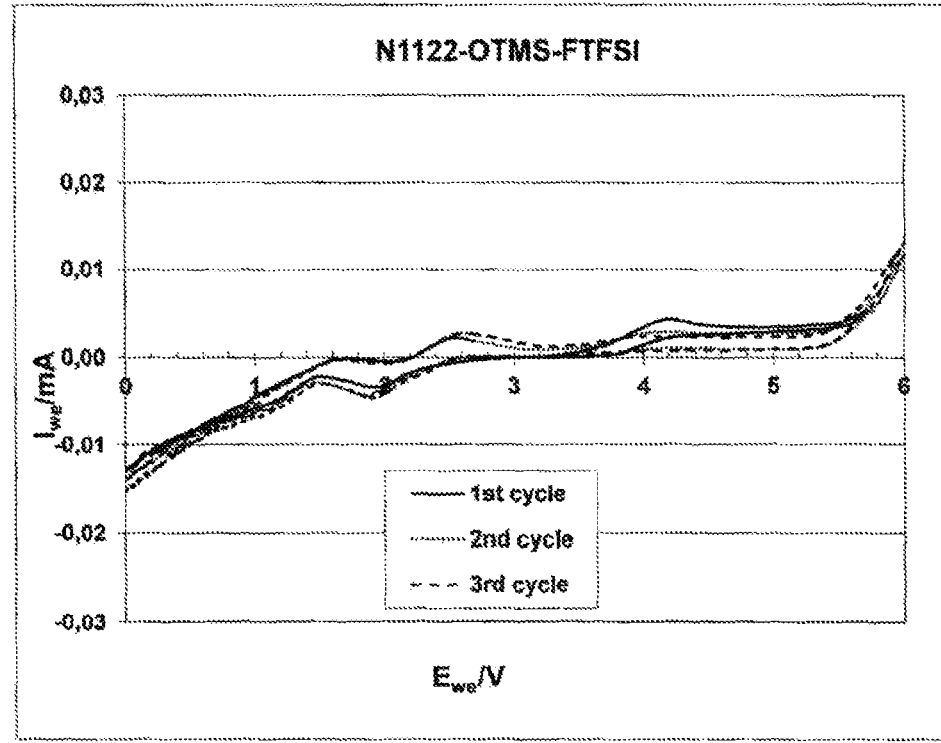
FIG. 19 shows the cyclic voltametry of N1122-OTMS-FTFSI.

The compound prepared in Example 31 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 19).

Example 41—CV of N-ethyl-N-(2-(trimethylsiloxy)ethyl)-N,N-dimethylammonium bis(fluorosulfonyl)amide (N1122-OTMS-FSI)

Figure 20:
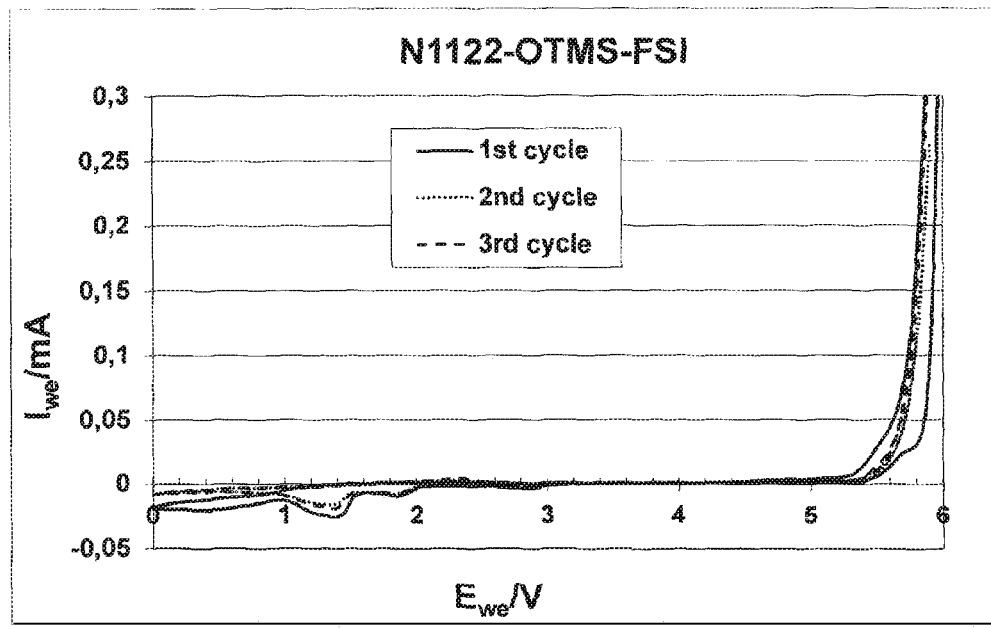
FIG. 20 shows the cyclic voltametry of N1122-OTMS-FSI.

The compound prepared in Example 32 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 20).

Example 42—CV of N-ethyl-N-(3-(trimethylsiloxy)propyl)-N,N-dimethylammonium bis(trifluoromethanesulfonyl)amide (N1123-OTMS-TFSI)

Figure 21:
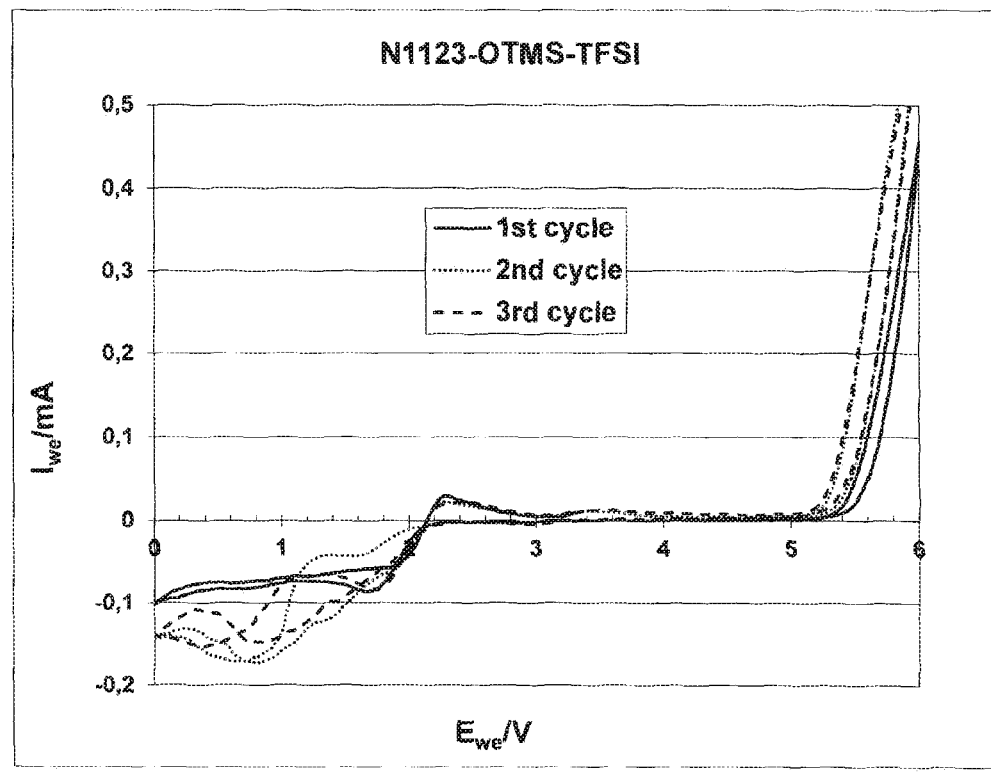
FIG. 21 shows the cyclic voltametry of N1123-OTMS-TFSI.

The compound prepared in Example 33 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 21).

Example 43—CV of N-ethyl-N-(4-(trimethylsiloxy)butyl)-N,N-dimethylammonium bis(trifluoromethanesulfonyl)amide (N1124-OTMS-TFSI)

Figure 22:
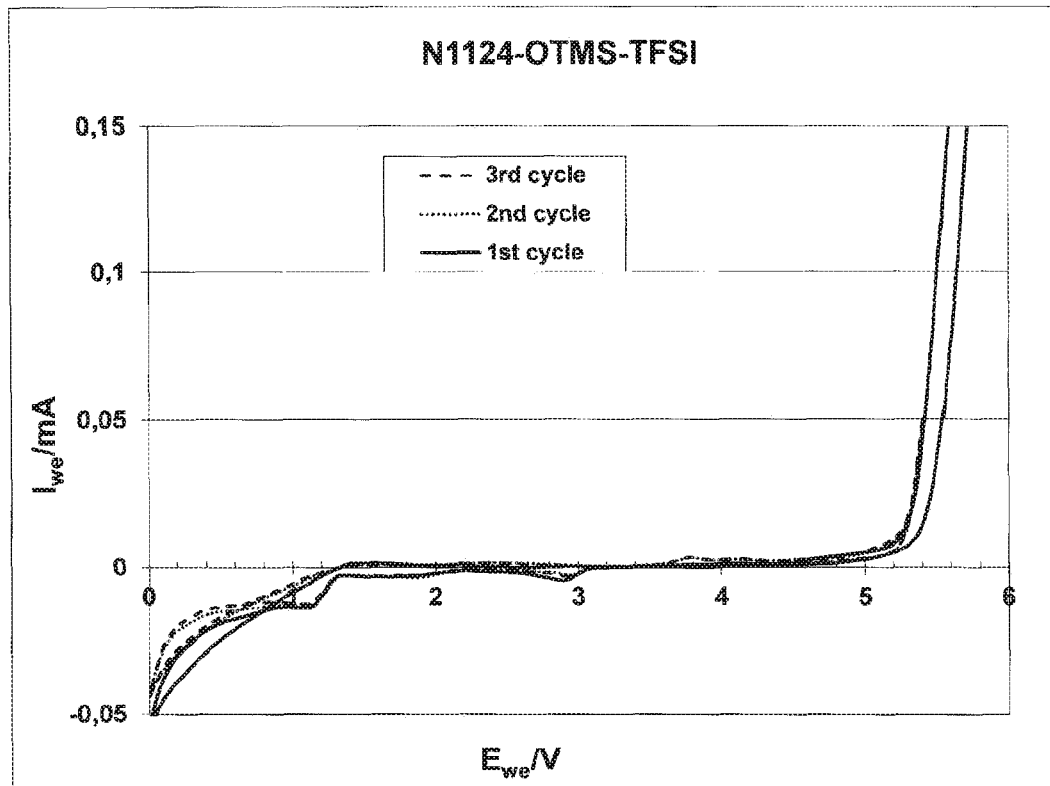
FIG. 22 shows the cyclic voltametry of N1124-OTMS-TFSI.

The compound prepared in Example 34 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 22).

Example 44—CV of N-ethyl-N-(6-(trimethylsiloxy)hexyl)-N,N-dimethylammonium bis(trifluoromethanesulfonyl)amide (N1126-OTMS-TFSI)

Figure 23:
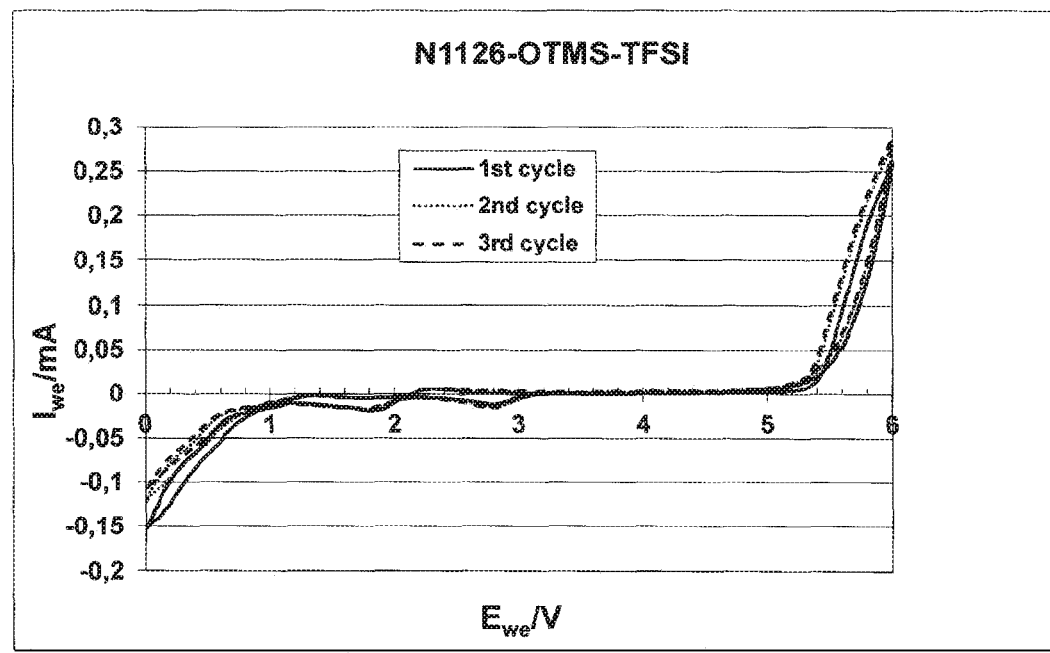
FIG. 23 shows the cyclic voltametry of N1126-OTMS-TFSI.

The compound prepared in Example 35 was charged into electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 23).

Example 45—CV of N-ethyl-N-2-(2-(trimethylsiloxy)ethoxy)ethyl-N,N-dimethylammonium bis(trifluoromethanesulfonyl)amide (N1122O2-OTMS-TFSI)

Figure 24:
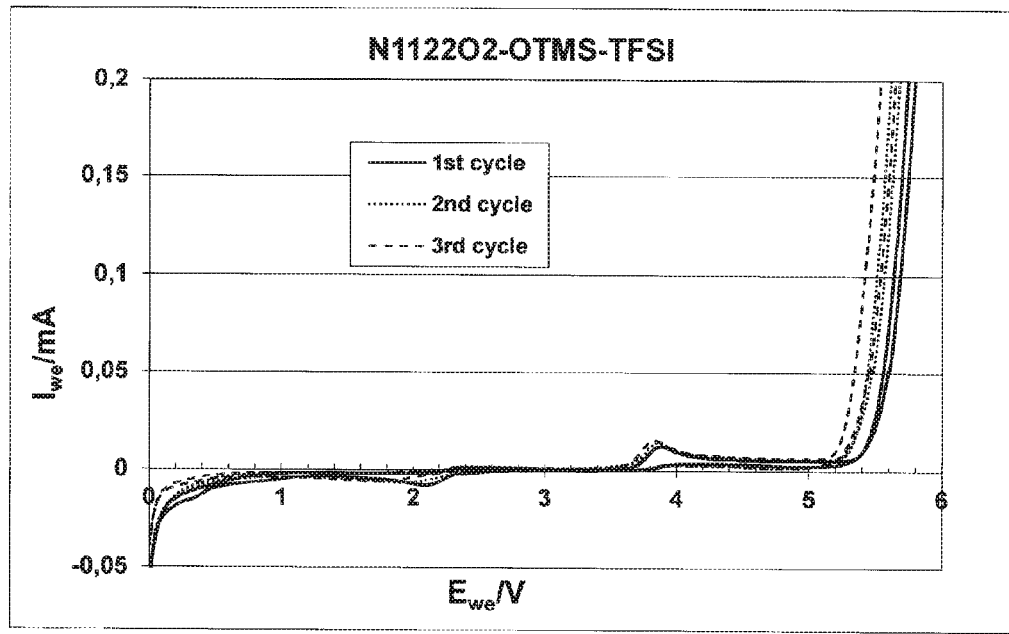
FIG. 24 shows the cyclic voltametry of N1122O2-OTMS-TFSI.

The compound prepared in Example 36 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 24).

Example 46—CV of 3-methyl-1-(2-(trimethylsiloxy)ethyl)imidazolium bis(trifluoromethanesulfonyl)amide (Im12-OTMS-TFSI)

Figure 25:
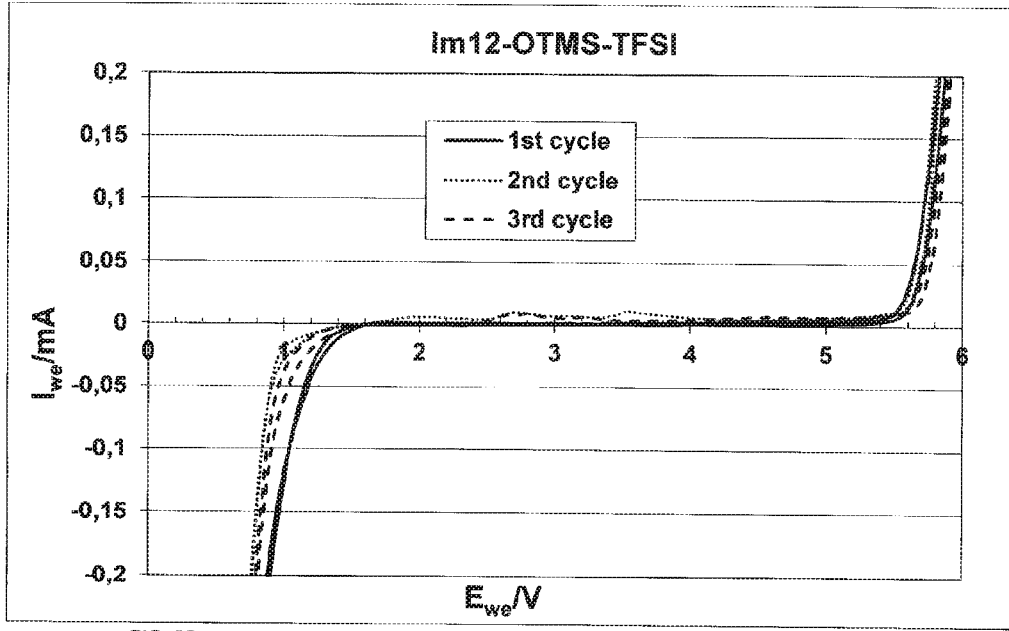
FIG. 25 shows the cyclic voltametry of Im12-OTMS-TFSI.

The compound prepared in Example 37 was charged into an electrochemical cell. This was a three electrodes cell having a Pt wire as a working electrode, lithium metal (as a sheet) as a counter electrode and another sheet of lithium metal as a reference electrode. The CV curve was measured between 0-6 V vs. Li at a rate of 1 mV/s (FIG. 25).

Example 47—Compatibility of Electrolyte with Graphite

Figure 26:
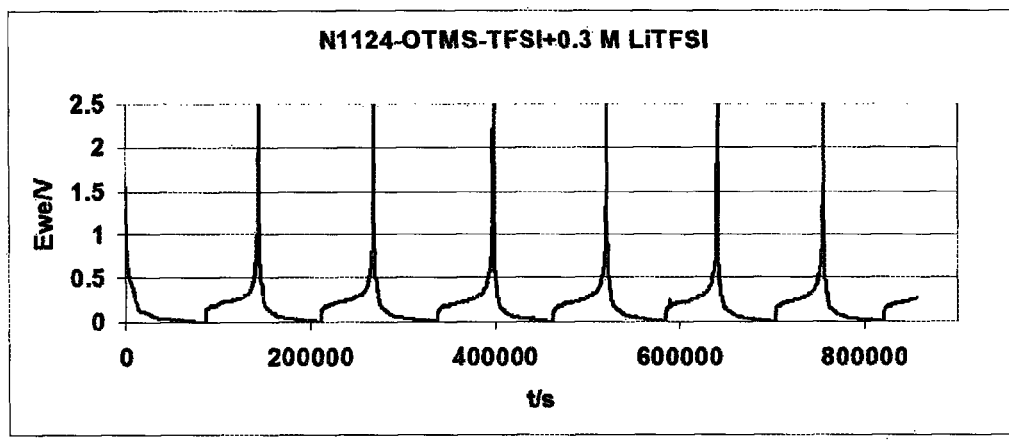
FIG. 26 shows the charge-discharge curves of graphite vs Li metal in a N1124-OTMS-TFSI based electrolyte.

A 0.3 molar solution of LiTFSI in the ionic liquid (IL) prepared in Example 34, was prepared by mixing 1.7225 g LiTFSI in 20 ml of the IL. This solution was charged into a three-electrode electrochemical cell with a graphite electrode. The anode material was prepared as described in Example 14. Two pieces of Li metal sheets were used as reference and counter electrodes and graphite was used as a working electrode. This cell was cycled between 0-2.5V versus Li at a current rate C/24 (FIG. 26). The lithium was successfully intercalated in the graphite with low coulombic efficiency in the first cycle. This improved in the second cycle to reach 89% with a reversible capacity of 253 mAh/g.

Example 48—Compatibility of Electrolyte with Graphite

Figure 27:
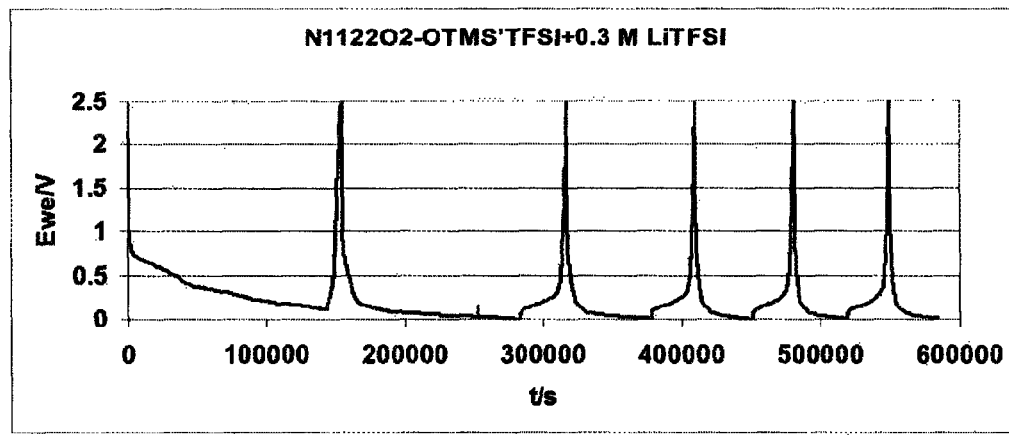
FIG. 27 shows the charge-discharge curves of graphite vs Li metal in a N1122O2-OTMS-TFSI based electrolyte.

A 0.3 molar solution of LiTFSI in the ionic liquid (IL) prepared in Example 36, was prepared by mixing 1.7225 g LiTFSI in 20 ml of the IL. This solution was charged into a three-electrode electrochemical cell with a graphite electrode. The anode material was prepared as described in Example 14. Two pieces of Li metal sheets were used as reference and counter electrodes and graphite was used as a working electrode. The cell was cycled between 0-2.5V versus Li at a current rate C/24 (FIG. 27). The lithium intercalation in the graphite was quite successful, but only in the third cycle after a solid electrolyte interface layer was well formed. The coulumbic efficiency reached 78% in the 5th cycle with a reversible capacity of 130 mAh/g.

Example 49—Comparative Example

Preparation of N-ethyl-N-(2-methoxyethyl)-N,N-dimethylammonium bis(trifluoromethane sulfonyl) amide (N1122-O1-TFSI)

a)
N-ethyl-N-(2-methoxyethyl)-N,N-dimethylammonium bromide

In a 500 ml round bottom flask equipped with a magnetic stirrer were placed 36.6 g (0.500 mol) of ethyldimethylamine dissolved in 100 ml of MeCN and MeOH (1:1). To this solution, 48 g (0.508 mol) of methyl 2-chloroethyl ether was added drop wise. Then, the mixture was refluxed for 96 h. The mixture was then evaporated and recrystallized from acetone. Altogether, 66.2 g (86%) of N-ethyl-N-(2-methoxyethyl)-N,N-dimethylammonium chloride were obtained.

b) N-ethyl-N-(2-methoxyethyl)-N,N-dimethylammonium bis(trifluoromethanesulfonyl)amide In a 250 ml round bottom flask, solutions of 66 g (0.430 mol) of N-ethyl-N-(2-methoxyethyl)-N,N-dimethylammonium chloride in 70 ml MQ water and 125 g (0.435 mol) of LiTFSI in 80 ml MQ water were mixed together under vigorous stirring. Phase separation occurred at once, but stirring was continued for another 4 hours at room temperature. Then, 150 ml of $CH_2Cl_2$ were added and the phases separated. The water phase was extracted with 50 ml of $CH_2Cl_2$ and the combined organic phases were washed 6 times with 100 ml of MQ water. A solution of the ionic compound in dichloromethane was obtained and purified by addition of activated charcoal and subsequent filtration. The solvent was removed using a rotary evaporator and then under high vacuum at 60° C. In this manner, 150 g (85%) of pure N-ethyl-N-(2-methoxyethyl)-N,N-dimethylammonium bis(trifluoromethanesulfonyl)amide as a colourless liquid were obtained.

$^1$H NMR (300 MHz, DMSO-d$_6$) δ/ppm: 1.24 (t, J=7.10, 7.10 Hz, 3H), 3.02 (s, 6H), 3.30 (s, 3H), 3.38 (q, J=7.10 Hz, 2H), 3.45-3.52 (m, 2H), 3.73 (br. s., 2H).

$^{13}$C NMR (75 MHz, DMSO-d$_6$) δ/ppm: 7.80 (s), 50.11 (br. s.), 57.84 (s), 59.77 (br. s.), 61.87 (br. s.), 65.36 (s), 119.54 (q, J=321.80 Hz).

$^{19}$F NMR (470 MHz, CHLOROFORM-d) δ/ppm: −78.79 (s).

Example 50: Comparative Example: Compatibility of Electrolyte with Graphite

Figure 28:
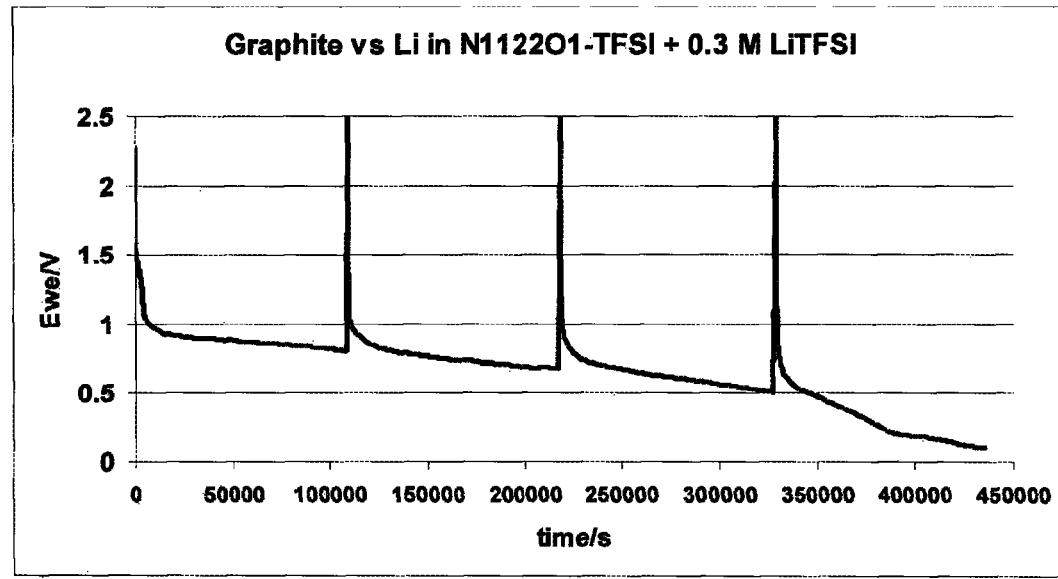
FIG. 28 shows the charge-discharge curves of graphite vs Li metal in a N1122O1-TFSI based electrolyte (comparative example with silyloxy group).

A 0.3 molar solution of LiTFSI in the ionic liquid (IL) prepared in Example 49, was prepared by mixing 1.7225 g LiTFSI in 20 ml of the IL. This solution was charged into a three-electrodes electrochemical cell with a graphite electrode. The anode material was prepared as described in Example 14. Two pieces of Li metal sheets were used as reference and counter electrodes and graphite was used as a working electrode. The cell was prepared to be cycled between 0-2.5V versus Li at a current rate C/24 (FIG. 28). The potential reached a plateau at approx 0.8 V in the first cycle and did not drop down to 0 V in 30 h of reduction, what is indicative of a decomposition reaction. Consequently, no reversible capacity was obtained. Therefore, this electrolyte cannot be used for low reductive voltages, such as graphite anode based batteries.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:
U.S. Pat. No. 6,365,301,
U.S. Pat. No. 6,365,068,
US 2008/0266642,
WO 2009/013046,
US 2009/0045373,
JP 2010-095473A,
1. Wasserscheid, P. and T. Welton, Eds. (2008). Ionic liquids in synthesis Weinheim, Wiley-VCH, pp. 148-155,
2. Ue, M.; Murakami, A.; Omata, K.; Nakamura, S., On the Anodic Stability of Organic Liquid Electrolytes. Book of Abstracts of 41st Battery Symposium in Japan 2000, 292-293.
3. N. Koura, et al. Chem Lett, 12 (2001), pp. 1320-1321 and Abs. 360, IMLB meeting, The Electrochemical Society, Inc: Nara, Japan; 2004
4. Holzapfel et al. Chem Commun, 4 (2004), pp. 2098-2099 and Carbon, 43 (2005), pp. 1488-1498,
5. Journal of Power Sources 162 (2006) 658-662] using 1-ethyl-3-methylimidazolium (EMIm)-FSI and EMIm-TFSIc,
6. Journal of Power Sources 175 (2008) 866-873,
7. Matsumoto, H., Kubota, K., Tsuxuki, S., & Sakaebe, H. (2011). *Charge and Discharge Property of Carbon Negative Electrode in Fluorosulfonyl(trifluoromethylsulfonyl) amide ionic liquids*. Paper presented at the 52$^{nd}$ Japan Battery Symposia, Funabori, Tokyo,
8. Zhang, Z.; Dong, J.; West, R.; Amine, K., Oligo(ethylene glycol)-functionalized disiloxanes as electrolytes for lithium-ion batteries. Journal of Power Sources 2010, 195 (18), 6062-6068, and
9. Lukevics, E.; Liberts, L.; Voronkov, M. G., Organosilicon Derivatives of Aminoalcohols. Russian Chemical Reviews 1970, 39 (11), 953-963.

The invention claimed is:

1. A lithium or lithium-ion battery electrolyte consisting of a conducting lithium salt dissolved in at least one ionic liquid of formula (I), and optionally up to 15 wt %, based on the total weight of the electrolyte, of one or more unsaturated carbonate,
the ionic liquid of formula (I) being:

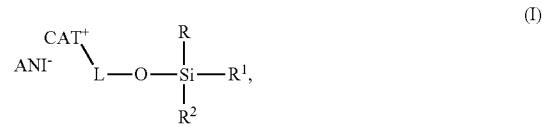

wherein:
CAT$^+$ represents a cation containing a positively singled charged atom, which is nitrogen, phosphorus or sulfur;
R, R$^1$ and R$^2$ are independently C$_1$-C$_8$ alkyl, alkenyl or alkynyl groups, L represents a linker and is a $C_1$-$C_{12}$ alkylene, alkenylene, or alkynylene group, optionally comprising one or more ether function, and optionally substituted with one or more halogen atoms, and $ANI^-$ represents an anion.

2. The electrolyte of claim 1, wherein L together with the oxygen atom to which it is attached form one or more alkyleneoxy group.

3. The electrolyte of claim 1, wherein the positively charged atom is nitrogen.

4. The electrolyte of claim 1, wherein the cation is of formula (IIIa), (IIIb), or (IIIc):

(IIIa)

(IIIb)

(IIIc)

wherein:
X is —$CH_2$—$CH_2$—$CH_2$—,
—$CH_2$—$C(=O)$—$CH_2$—$CH_2$—,
—$CH_2$—$CH_2$—$C(=O)$—$CH_2$—,
—N(alkyl)-$CH_2$—$CH_2$—$CH_2$—,
—$CH_2$—$CH_2$—$CH_2$—N(alkyl)-,
—$CH_2$—N(alkyl)-$CH_2$—$CH_2$—,
—$CH_2$—$CH_2$—N(alkyl)-$CH_2$—,
—$CH_2$—$CH_2$—$CH_2$—$CH_2$—$CH_2$—,
—$CH_2$—$CH_2$—$CH_2$—$CH_2$—$CH_2$—$CH_2$—,
—$CH_2$—$CH_2$—O—$CH_2$—$CH_2$—,
—$CH_2$—O—$CH_2$—$CH_2$—$CH_2$—,
—$CH_2$—$CH_2$—$CH_2$—O—$CH_2$—,
—$CH_2$—$CH_2$—N(alkyl)-$CH_2$—$CH_2$—,
—$CH_2$—N(alkyl)-$CH_2$—$CH_2$—$CH_2$—,
—$CH_2$—$CH_2$—$CH_2$—N(alkyl)-$CH_2$—,
—N(alkyl)-$CH_2$—$CH_2$—$CH_2$—$CH_2$—, or
—$CH_2$—$CH_2$—$CH_2$—$CH_2$—N(alkyl)-; and
$R^6$ is a $C_1$-$C_{16}$ alkyl, alkenyl, or alkynyl group.

5. The electrolyte of claim 1, wherein the cation is of formula (IVa), (IVb), or (IVc):

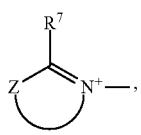
(IVa)

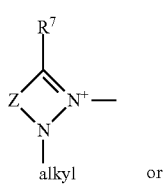
(IVb)

(IVc)

wherein:
for IVa, Z is —CH=CH—, —$CH_2$—$CH_2$—$CH_2$—,
—CH=CH—CH=CH—$CH_2$—,
—N=CH—CH=CH—, —CH=N—CH=CH—,
—N(alkyl)-CH=CH—,
—$CH_2$—CH=CH—O—, =CH—$CH_2$—$CH_2$—O—,
—O—$CH_2$—CH=CH—, —O—CH=CH—$CH_2$—,
—CH=CH—O—$CH_2$—, =CH—$CH_2$—O—$CH_2$—,
—$CH_2$—O—CH=CH—, =CH—O—$CH_2$—$CH_2$—, or
—N(alkyl)-N=CH—,
for IVb, Z is —CH=CH—, and
for IVc, Z is —N(alkyl)-CH=CH—; and
$R^7$ is hydrogen or alkyl.

6. The electrolyte of claim 1, wherein the cation is of formula (IIa), (IIb) or (IIc):

(IIa)

(IIb)

(IIc)

wherein $R^3$, $R^4$ and $R^5$ are independently $C_1$-$C_{16}$ alkyl, alkenyl, or alkynyl groups.

7. The electrolyte of claim 6, wherein the cation is a formula (IIa).

8. The electrolyte of claim 1, wherein the anion is:
a halide,
perchlorate,
hexafluorophosphate,
tris(pentafluoroethyl)trifluorophosphate,
tetrafluoroborate,
trifluoromethyltrifluoroborate,
pentafluoroethyltrifluoroborate,
heptafluoropropyltrifluoroborate,
nonafluorobutyltrifluoroborate,
trifluoromethanesulfonate,
trifluoroacetate,
bis(fluorosulfonyl)amide,
or a sulfonylamide of formula (V):

$$A\text{-}N^-\text{—}SO_2\text{—}B \qquad (V),$$

wherein A is F—$SO_2$—, $CF_3$—$SO_2$—, $C_2F_5$—$SO_2$—, $C_3F_7$—$SO_2$—, $C_4F_9$—$SO_2$—, or $CF_3$—$C(=O)$—;
and B is —F, —$CF_3$, —$C_2F_5$, —$C_3F_7$, —$C_4F_9$; N is Nitrogen; and S is Sulfur.

9. The electrolyte of claim 8, wherein the sulfonylamide of formula (V) is:
bis(trifluoromethanesulfonyl)amide,
bis(pentafluoroethylsulfonyl)amide,
bis(heptafluoropropylsulfonyl)amide,
bis(nonafluorobutylsulfonyl)amide,
N-trifluoroacetyl-fluorosulfonylamide,
N-trifluoroacetyl-trifluoromethanesulfonylamide,
N-trifluoroacetyl-pentafluoroethylsulfonyl amide,
N-trifluoroacetyl-heptafluoropropylsulfonylamide,
N-trifluoroacetyl-nonafluorobutylsulfonylamide,
N-fluorosulfonyl-trifluoromethanesulfonylamide,
N-fluorosulfonyl-pentafluoroethylsulfonylamide,
N-fluorosulfonyl-heptafluoropropylsulfonylamide,
N-fluorosulfonyl-nonafluorobutylsulfonylamide,
N-trifluoromethanesulfonyl-pentafluoroethylsulfonyl amide,
N-trifluoromethanesulfonyl-heptafluoropropylsulfonyl-amide, or
N-trifluoromethanesulfonyl-nonafluorobutylsulfonylamide.

10. The electrolyte of claim 1, wherein the one or more unsaturated carbonate are absent.

11. The electrolyte of claim 1, wherein the one or more unsaturated carbonate are present.

12. The electrolyte of claim 11, wherein the one or more unsaturated carbonate is vinylene carbonate.

13. The electrolyte of claim 1, wherein the ionic liquid comprises:

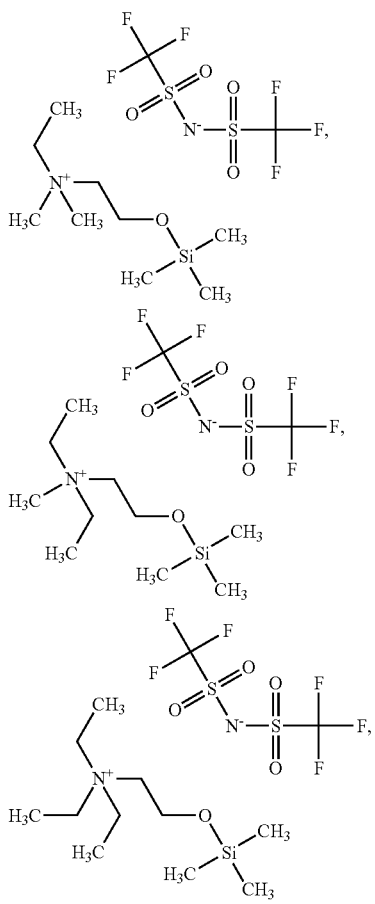

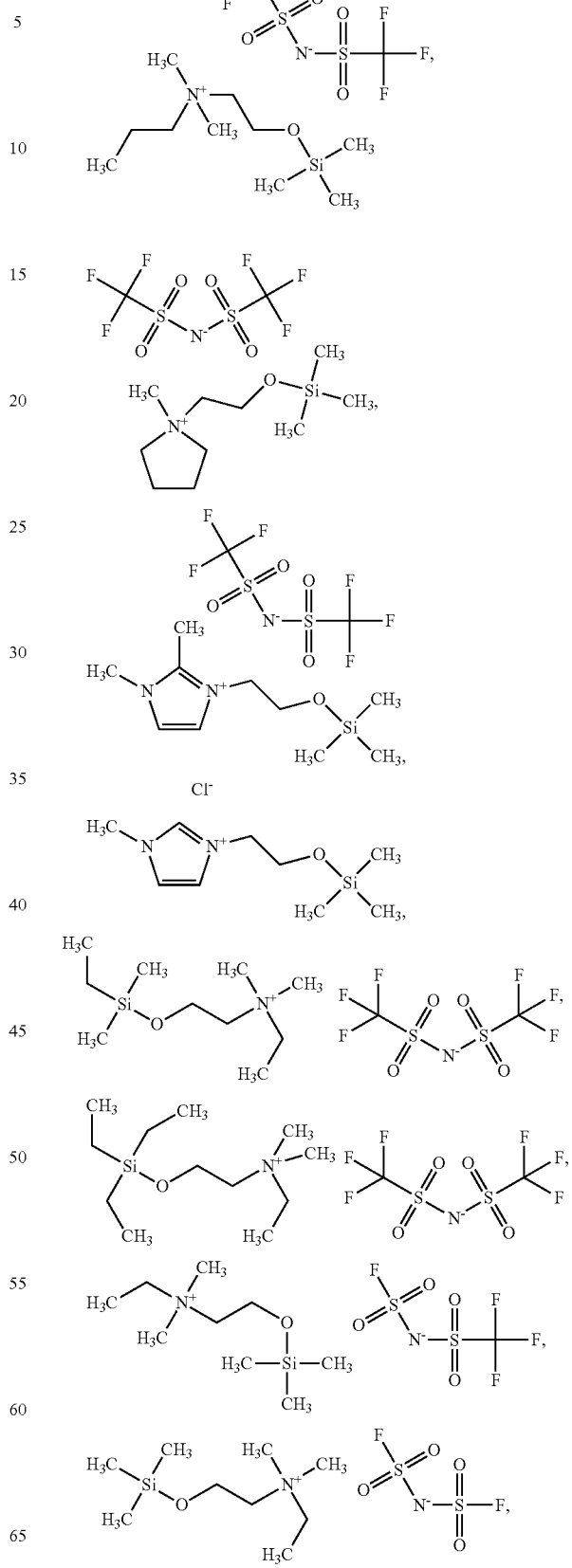

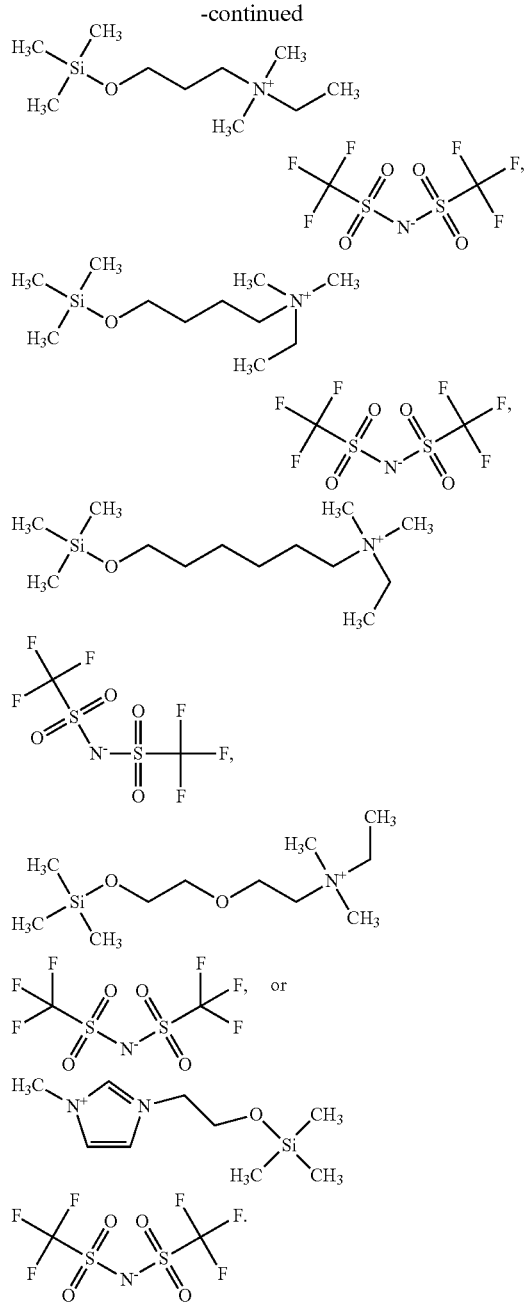
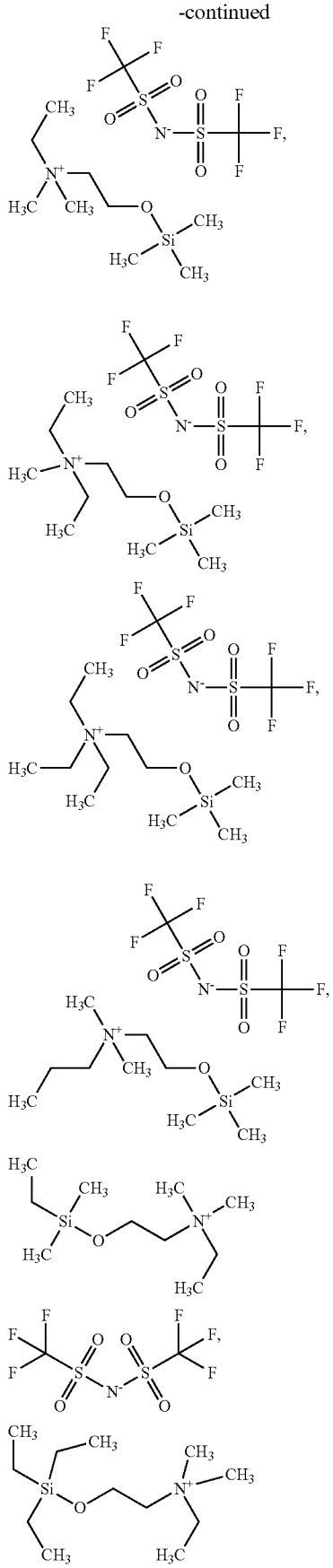
14. The electrolyte of claim 1, wherein the ionic liquid comprises:
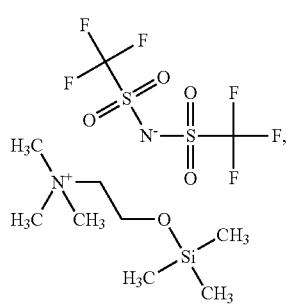

-continued

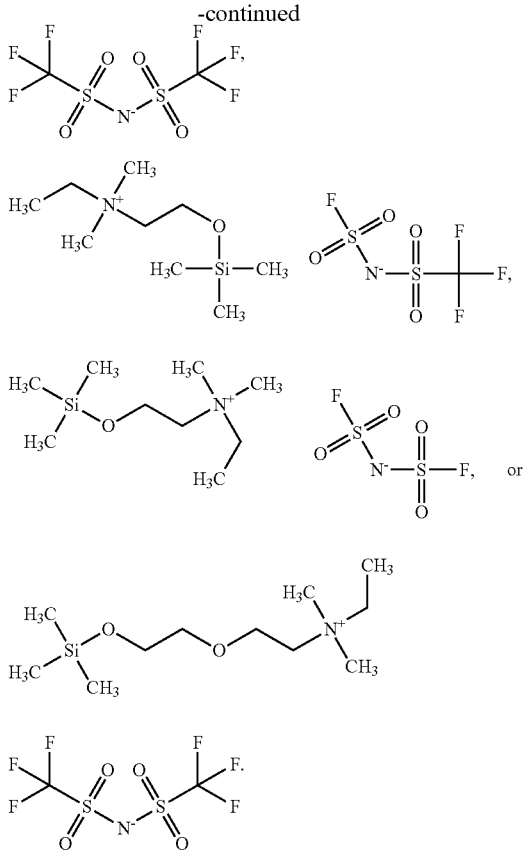

15. The electrolyte of claim 1, wherein CAT$^+$ represents a cation of formula (IIa):

$$R^4-\overset{R^3}{\underset{R^5}{N^+}}-,\qquad(IIa)$$

wherein $R^3$, $R^4$ and $R^5$ are independently $C_1$-$C_6$ alkyl groups;
R, $R^1$ and $R^2$ are independently $C_1$-$C_4$ alkyl groups;
L together with the oxygen atom to which it is attached form one or two ethyleneoxy groups; and
ANI$^-$ represents a sulfonylamide anion of formula (V):

$$\text{A-N}^--SO_2-B \qquad (V),$$

wherein A is F—SO$_2$—, CF$_3$—SO$_2$—, C$_2$F$_5$—SO$_2$—, C$_3$F$_7$—SO$_2$—, C$_4$F$_9$—SO$_2$—; and B is —F, —CF$_3$, —C$_2$F$_5$, —C$_3$F$_7$, —C$_4$F$_9$.

16. The electrolyte of claim 15, wherein $R^3$, $R^4$ and $R^5$ are independently $C_1$-$C_3$ alkyl groups.

17. The electrolyte of claim 15, wherein R, $R^1$ and $R^2$ are independently $C_1$-$C_2$ alkyl groups.

18. The electrolyte of claim 15, wherein the anion is bis(fluorosulfonyl)amide, bis(trifluoromethanesulfonyl)amide, or N-fluorosulfonyl-trifluoro-methanesulfonylamide.

19. An electrochemical cell comprising an anode, a cathode, and an electrolyte as defined in claim 1.

20. The electrochemical cell of claim 19, wherein the anode is a graphite electrode.

\* \* \* \* \*